US009290561B2

(12) United States Patent
Weimer et al.

(10) Patent No.: US 9,290,561 B2
(45) Date of Patent: Mar. 22, 2016

(54) FACTOR VIII, VON WILLEBRAND FACTOR OR COMPLEXES THEREOF WITH PROLONGED IN VIVO HALF-LIFE

(71) Applicants: Thomas Weimer, Gladenbach (DE); Stefan Schulte, Marburg (DE); Hubert Metzner, Marburg (DE); Ulrich Kronthaler, Deisenhofen (DE); Holger Lind, Marburg (DE); Wiegand Lang, Colbe (DE)

(72) Inventors: Thomas Weimer, Gladenbach (DE); Stefan Schulte, Marburg (DE); Hubert Metzner, Marburg (DE); Ulrich Kronthaler, Deisenhofen (DE); Holger Lind, Marburg (DE); Wiegand Lang, Colbe (DE)

(73) Assignee: CSL Behring GmbH, Marburg (DE)

( * ) Notice: Subject to any disclaimer, the term of this patent is extended or adjusted under 35 U.S.C. 154(b) by 0 days.

(21) Appl. No.: 14/028,869

(22) Filed: Sep. 17, 2013

(65) Prior Publication Data

US 2014/0072561 A1   Mar. 13, 2014

Related U.S. Application Data

(63) Continuation of application No. 13/000,938, filed as application No. PCT/EP2009/004549 on Jun. 24, 2009, now Pat. No. 8,575,104.

(30) Foreign Application Priority Data

Jun. 24, 2008 (EP) ..................... 08011429

(51) Int. Cl.
| A61K 38/37 | (2006.01) |
| A61K 38/36 | (2006.01) |
| A61K 38/38 | (2006.01) |
| A61K 38/16 | (2006.01) |
| A61K 35/14 | (2015.01) |
| C07K 1/00 | (2006.01) |
| C07K 14/76 | (2006.01) |
| C07K 14/755 | (2006.01) |
| A61K 38/00 | (2006.01) |

(52) U.S. Cl.
CPC .............. *C07K 14/76* (2013.01); *C07K 14/755* (2013.01); *A61K 38/00* (2013.01); *C07K 2319/31* (2013.01)

(58) Field of Classification Search
None
See application file for complete search history.

(56) References Cited

U.S. PATENT DOCUMENTS

| 4,970,300 A | 11/1990 | Fulton et al. |
| 5,364,771 A | 11/1994 | Lollar et al. |
| 5,408,039 A | 4/1995 | Burnouf-Radosevich et al. |
| 5,854,403 A | 12/1998 | Fischer et al. |
| 5,876,969 A | 3/1999 | Fleer et al. |
| 6,228,613 B1 | 5/2001 | Fischer et al. |
| 6,403,077 B1 | 6/2002 | Strom et al. |
| 7,482,013 B2 | 1/2009 | Ballance et al. |
| 2004/0087778 A1 | 5/2004 | Feige et al. |

FOREIGN PATENT DOCUMENTS

| EA | 006209 B1 | 10/2005 |
| EP | 0503991 B1 | 9/1998 |
| EP | 0784632 B1 | 1/1999 |
| EP | 1502921 A1 | 2/2005 |
| EP | 1867660 A1 | 6/2006 |
| WO | WO-94/15625 A1 | 7/1994 |
| WO | WO-97/03193 A1 | 1/1997 |
| WO | WO-97/11957 A1 | 4/1997 |
| WO | WO-97/24445 | 7/1997 |
| WO | WO 97/34930 A1 | 9/1997 |
| WO | WO-97/40145 A1 | 10/1997 |
| WO | WO-99/55306 A1 | 11/1999 |
| WO | WO-01/79271 A1 | 10/2001 |
| WO | WO-02/060951 A2 | 8/2002 |
| WO | WO-02/103024 A2 | 12/2002 |
| WO | WO-03/076567 A2 | 9/2003 |
| WO | WO-03/087355 A1 | 10/2003 |
| WO | WO-03/093313 A2 | 11/2003 |
| WO | WO-2004/052401 A2 | 6/2004 |
| WO | WO-2004/052401 A3 | 6/2004 |
| WO | WO-2004/075923 A2 | 9/2004 |
| WO | WO-2004/075923 A3 | 9/2004 |
| WO | WO-2004/101740 A2 | 11/2004 |
| WO | WO-2004/101740 A3 | 11/2004 |
| WO | WO-2005/000892 A2 | 1/2005 |
| WO | WO-2005/000892 A3 | 1/2005 |

(Continued)

OTHER PUBLICATIONS

Examination Report for Australian Patent Application No. 2013202564 dated Jun. 5, 2014 (4 pages).

(Continued)

*Primary Examiner* — Shulamith H Shafer
(74) *Attorney, Agent, or Firm* — Finnegan, Henderson, Farabow, Garrett & Dunner LLP

(57) ABSTRACT

The present invention relates to modified nucleic acid sequences coding for coagulation factor VIII (FVIII) and for von Willebrand factor (VWF) as well as complexes thereof and their derivatives, recombinant expression vectors containing such nucleic acid sequences, host cells transformed with such recombinant expression vectors, recombinant polypeptides and derivatives coded for by said nucleic acid sequences which recombinant polypeptides and derivatives do have biological activities together with prolonged in vivo half-life and/or improved in vivo recovery compared to the unmodified wild-type protein. The invention also relates to corresponding FVIII sequences that result in improved expression yield. The present invention further relates to processes for the manufacture of such recombinant proteins and their derivatives. The invention also relates to a transfer vector for use in human gene therapy, which comprises such modified nucleic acid sequences.

31 Claims, 5 Drawing Sheets

(56) References Cited

FOREIGN PATENT DOCUMENTS

| WO | WO-2005/001025 A2 | 1/2005 |
|---|---|---|
| WO | WO-2005/001025 A3 | 1/2005 |
| WO | WO-2005/024044 A2 | 3/2005 |
| WO | WO-2005/024044 A3 | 3/2005 |
| WO | WO-2005/063808 A1 | 7/2005 |
| WO | WO-2006/000448 A2 | 1/2006 |
| WO | WO-2006/000448 A3 | 1/2006 |
| WO | WO-2006/053299 A2 | 5/2006 |
| WO | WO-2006/053299 A3 | 5/2006 |
| WO | WO-2006/071801 A2 | 7/2006 |
| WO | WO-2006/071801 A3 | 7/2006 |
| WO | WO-2006/108590 A1 | 10/2006 |
| WO | WO-2007/090584 A1 | 8/2007 |
| WO | WO-2007/126808 A1 | 11/2007 |
| WO | WO-2007/144173 A1 | 12/2007 |
| WO | WO 2009/156137 | 12/2009 |
| WO | WO 2013/083858 A1 | 6/2013 |
| WO | WO 2013/106787 A1 | 7/2013 |

OTHER PUBLICATIONS

Notice of Preliminary Rejection for Korean Patent Application No. 10-2011-7001530 dated Oct. 24, 2014 (14 pages).

Russian office action for Russian Patent Application No. 2011102366 dated Aug. 26, 2013, 6 pages.

English translation of Decision to Grant Russian Application No. 2011102366 (5 pages).

Björkman et al., "Pharmacokinetics of Coagulation Factors: Clinical Relevance for Patients with Haemophilia," *Clin. Pharmacokinet* 40(11):815-832 (2001).

Gensana et al., "Influence of von Willebrand Factor on the Reactivity of Human Factor VIII Inhibitors with Factor VIII," *Haemophilia* 7:369-374 (2001).

Goudemand, J., "Inhibitor Development in Haemophilia A: the Role of von Willebrand Factor/Factor VIII Concentrates," *Haemophilia* 13(Suppl. 5):47-51 (2007).

Kaveri et al., "Factor VIII Inhibitors: Role of von Willebrand Factor on the Uptake of Factor VIII by Dendritic Cells," *Hemophilia* 13(Suppl. 5):61-64 (2007).

Nogami et al., "A Novel Mechanism of Factor VIII Protection by von Willebrand Factor from Activated Protein C-Catalyzed Inactivation," *Blood* 99(11):3993-3998 (2002).

Aledort L.M., "Comparative thrombotic event incidence after infusion of recombinant factor VIIa versus factor VIII inhibitor bypass activity," Journal of Thrombosis and Haemostasis, 2:1700-08 (2004).

Amano K. et al., "Mutation at either Arg336 or Arg562 in factor VIII is insufficient for complete resistance to activated protein C (APC)-mediated inactivation: Implications for the APC resistance test," Thromb Haemost., 79:557-63 (1998).

Ananyeva N.M. et al., "Catabolism of the coagulation factor VIII: Can we prolong lifetime of fVIII in circulation?," TCM, 11:251-57 (2001).

Baronciani L. et al., "Molecular characterization of a multiethnic group of 21 patients with type 3 von Willebrand disease," Thromb Haemost., 84:536-40 (2000).

Beattie W.G. et al., "Structure and evolution of human α-fetoprotein deduced from partial sequence of cloned cDNA," Gene, 20:415-22 (1982).

Bettini R. et al. review of Kibbe A.H. "Handbook of Pharmaceutical Excipients," Third Edition (Pharmaceutical Pres, London, 2000).

Chuang V.T.G. et al., "Pharmaceutical strategies utilizing recombinant human serum albumin," Pharmaceutical Research, 19:569-77 (2002).

Collins C.J. et al., "Molecular cloning of the human gene for von Willebrand factor and identification of the transcription initiation site," Proc. Natl. Acad. Sci., 84:4393-97 (1987).

Colman et al., Hemostasis and Thrombosis: basic principles and clinical practice, 5$^{th}$ Edition, pp. 710-713 (2006).

Cooke N.E. et al., "Serum vitamin D-binding protein is a third member of the albumin and alpha fetoprotein gene family," J. Clin. Invest., 76:2420-24 (1985).

Denis C. et al., "A mouse model of severe von Willebrand disease: Defects in hemostasis and thrombosis," Proc. Natl. Acad. Sci., 95:9524-29 (1998).

Dumont J.A. et al., "Monomeric Fc fusions," Biodrugs, 20:151-60 (2006).

Duttaroy, Alokesh, et al., "Development of a long-acting insulin analog using albumin fusion technology," Diabetes, 54:251-258 (2005).

Enayat M.S. et al., "Aberrant dimerization of von Willebrand factor as the result of mutations in the carboxy-terminal region: identification of 3 mutations in members of 3 different families with type 2A (phenotype IID) von Willebrand disease," Blood, 98:674-80 (2001).

Fay P.J. et al., "Characterization of the interaction between the A2 subunit and A1/A3-C1-C2 dimer in human factor VIII$_a$," J. Biol. Chem., 267:13246-50 (1992).

Fay P.J. et al., "Human factor VIII$_a$ subunit structure," J. Biol. Chem.., 266:8957-62 (1991).

Federici A.B. et al., "A sensitive ristocetin co-factor activity assay with recombinant glycoprotein Ib for the diagnosis of patients with low von Willebrand factor levels," Haematologica, 89:77-85 (2004).

Fischer B.E. et al., "Effect of multimerization of human and recombinant von Willebrand factor on platelet aggregation, binding to collagen and binding of coagulation factor VIII," Thrombosis Research, 84:55-66 (1996).

Fischer B. et al., "Structural analysis of recombinant von Willebrand factor: identification of hetero- and homo-dimers," FEBS Letters, 351:345-48 (1994).

Gale A.J. et al., "Intrinsic stability and functional properties of disulfide bond-stabilized coagulation factor VIIIa variants," Journal of Thrombosis and Haemostasis, 4:1315-22 (2006).

Gao, Zhihui, et al., "Development, characterization, and evaluation of a fusion protein of a novel gulcagon-like peptide-1 (GLP-1) analog and human serum albumin in Pichia pastoris," Biosci. Biotechnol. Biochem., 73(3):688-694 (2009).

Hommais et al., "Impaired dimerization of von Willebrand factor subunit due to mutation A280ID in the CK domain results in a recessive type 2A subtype IID von Willebrand disease," Thromb. Hemost, 95: pp. 776-81 (2006).

Huang, Yan-Shan, et al., "Preparation and characterization of a potent, long-lasting recombinant human serum albumin-interferon-α2b fusion protein expressed in Pichia pastoris," European J. Pharm. Biopharm., 67:301-308 (2007).

Kallas A. et al., "The von Willebrand factor collagen-binding activity assay: clinical application," Ann Hematol, 80:466-71 (2001).

Kang, Woo Kyu, et al., "A biologically active angiogenesis inhibitor, human serum albumin-TIMP-2 fusion protein, secreted from *Saccharomyces cerevisiae*," Protein Expression and Purification, 53:331-338 (2007).

Kaufman R.J. et al., "Effect of von Willebrand factor coexpression on the synthesis and secretion of factor VII in Chinese hamster ovary cells," Molecular and Cellular Biology, 9:1233-42 (1989).

Lee G., review of Frokjaer S. et al., "Pharmaceutical formulation development of peptides and proteins" (Taylor & Francis, Andover UK, 2000).

Leyte A. et al., "The interaction between human blood-coagulation factor VIII and von Willebrand factor," Biochem. J., 257:679-83 (1989).

Lichenstein H.S. et al., "Afamin is a new member of the albumin, α-fetoprotein, and vitamin D-binding protein gene family," J. Biol. Chem., 269:18149-54 (1994).

Lollar P., "Characterization of factor VII B-cell inhibitory epitopes," Thrombosis and Haemostasis, 82:50508 (1999).

Metzner, Hubert J., et al., "Genetic fusion to albumin improves the pharmacokinetic properties of factor IX," Thromb. Haemost., 102:634-644 (2009).

Melder, Robert J., et al., "Pharmacokinetics and in vitro and in vivo anti-tumor response of an interleukin-2-human serum albumin fusion protein in mice," Cancer Immunol. Immunother., 54:535-547 (2005).

(56) References Cited

OTHER PUBLICATIONS

Metzner H.J., "Characterization of factor VII/von Willebrand factor concentrates using a modified method of von Willebrand factor multimer analysis," Haemophilia, 4:25-32 (1998).
Miao H.Z. et al., "Bioengineering of coagulation factor VIII for improved secretion," Blood, 103:3412-19 (2004).
Office Action for U.S. Appl. No. 13/212,879 dated Nov. 8, 2012.
Oh S.-H. et al., "Synthesis of recombinant blood coagulation factor VIII (FVIII) heavy and light chains and reconstitution of active form of FVIII," Experimental and Molecular Medicine, 31:95-100 (1999).
Pfistershamer K. et al., "Recombinant factor VIII and factor VIII-von Willebrand factor complex do not present danger signals for human dendritic cells," Thromb. Haemost., 96:309-16 (2006).
Pipe S.W., "Coagulation factors with improved properties for hemophilia gene therapy," Seminars in Thrombosis and Hemostasis, 30:227-37 (2004).
Reply to Communication from European Patent Office dated Feb. 3, 2011, filed on Feb. 17, 2011, for European Patent Application No. 09768986.3.
Rizza C.R. et al., "Coagulation assay of VIIC and IXC," Chapter 2 in the Hemophilias (Bloom ed., Churchill Livingston, NY, 1992).
Rosen S., "Assay of factor VII:C with chromogenic substrate," Scand J Haematol., 33:139-45 (1984).
Saenko E.L. et al., "Strategies towards a longer acting factor VIII," Haemophilia, 12:42-51 (2006).
Saenko E.L. et al., "Molecular defects in coagulation factor VIII and their impact on Factor VIII function," Vox Sanguinis, 83:89-96 (2002).
Schneppenheim R. et al., "Expression and characterization of von Willebrand factor dimerization defects in different types of von Willebrand disease," Blood, 97:2059-66 (2001).
Schneppenheim R. et al., "Defective dimerization of von Willebrand factor subunits due to a Cys→Arg mutation in type IID von Willebrand disease," Proc. Natl. Acad. Sci., 93:3581-86 (1996).
Seffernick et al., "Melamine Deaminase and Atrazine Chlorohydrolase: 98 Percent Identical but Functionally Different," Journal of Bacteriology, 183(8): p. 2405-2410 (2001).
Sheffield, William P., et al., "Effects of genetic fusion of factor IX to albumin on in vivo clearance in mice and rabbits," British Journal of Haematology, 126:565-573 (2004).
Soukharev S. et al., "Expression of factor VIII in recombinant and transgenic systems," Blood Cells Molecules and Diseases, 28:234-48 (2002).
Sucker C. et al., "Determination of von Willebrand factor activity: evaluation of the HaemosIL™ assay in comparison with established procedures," Clinical and Applied Thrombosis/Hemostasis, 12:305-10 (2006).
Swaroop M. et al., "Mutagenesis of a potential immunoglobulin-binding protein-binding site enhances secretion of coagulation factor VIII," J. Biol. Chem., 272:24121-24 (1997).
Tatewaki W. et al., "Multimeric composition of plasma von Willebrand factor in chronic myelocytic leukaemia," Thrombosis Research, 52:23-32 (1988).
Tjernberg P. et al., "Homozygous C2362F von Willebrand factor induces intracellular retention of mutant von Willebrand factor resulting in autosomal recessive severe von Willebrand disease," British Journal of Haematology, 133:409-18 (2006).
Vehar G.A. et al., "Structure of human factor VII," Nature 312:337-42 (1984).
Wakabayashi H. et al., "A Glu113Ala mutation within a factor VIII $Ca^{2+}$-binding site enhances cofactor interactions in factor Xase," Biochemistry, 44:10298-304 (2005).
Weimer T. et al., "Prolonged in-vivo half-life of factor VIIa by fusion to albumin," Thromb Haemost, 99:659-67 (2008).
Wells, James A., "Additivity of Mutational Effects in Proteins," Biochemistry, 29(37), pp. 8509-8517 (1990).
Wood W.I. et al., "Expression of active human factor VII from recombinant DNA clones," Nature, 312:330-37 (1984).
Zhou et al., "Sequence and structure relationships within von Willebrand factor," Blood, 120: pp. 449-458 (2012).
Search Report in PCT/EP2009/004549 mailed Aug. 7, 2009.
Search Report in EP 0801142911-2403 dated Dec. 29, 2008.
Australian Patent Application No. 2009262476 by CSL Behring GmbH: Examination Report No. 1, dated Jan. 3, 2014.
Japanese Patent Application No. 2011-515200 by CSL Behring GmbH: Notice of the Reason of Rejection, dated Feb. 4, 2014, with English translation.
Gale et al., "Structural Basis for Hemophilia A Caused by Mutations in the C Domains of Blood Coagulation Factor VIII." *Thomb Haemost.* 83(1):78-85 (2000).
Lenting et al., "The Life Cycle of Coagulation Factor VIII in View of Its Structure and Function." *Blood.* 92(11): 3983-3996 (1998).
Liu et al., "Hemophilic factor VIII C1- and C2-domain missense mutations and their modeling to the 1.5-angstrom human C2-domain crystal structure." *Blood.* 96(3): 979-987 (2000).
Spiegel et al., "Structure of a factor VIII C2 domain-immunoglobulin G4κ Fab complex: identification of an inhibitory antibody epitope on the surface of factor VIII." *Blood.* 98(1): 13-19 (2001).

Figure 1: Antigen and activity levels of wild-type FVIII (457) and FVIII-C-terminal (1434) albumin fusion polypeptides
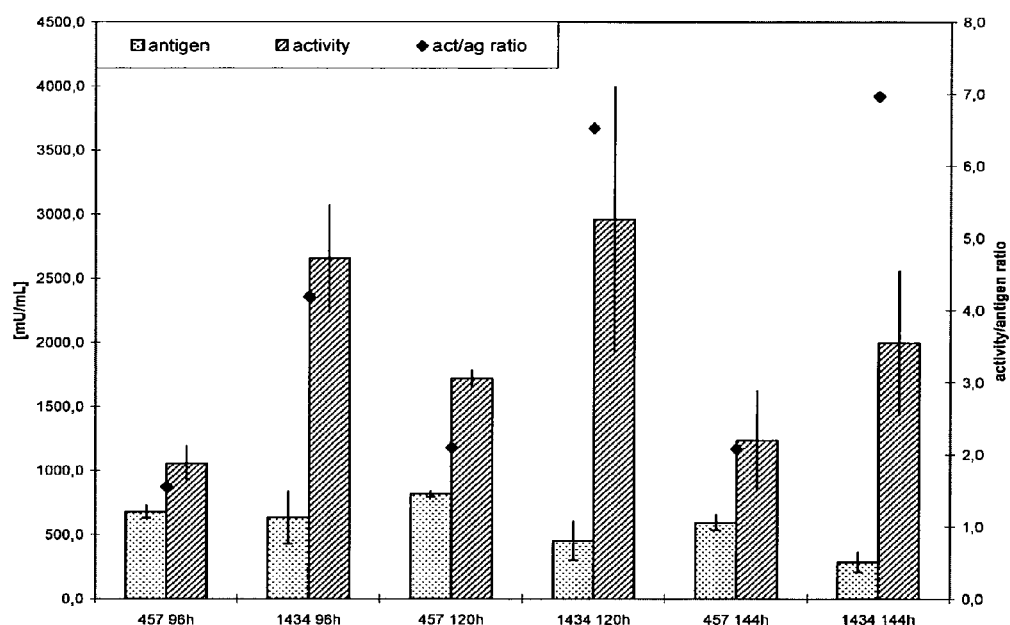

Figure 2: Comparison of human FVIII:Ag pharmacokinetics in VWF ko mice following i.v. injection of 100 U (FVIII:Ag)/kg FVIII wildtype and FVIII-FP 1656 VWF (mean; n=4/timepoint)
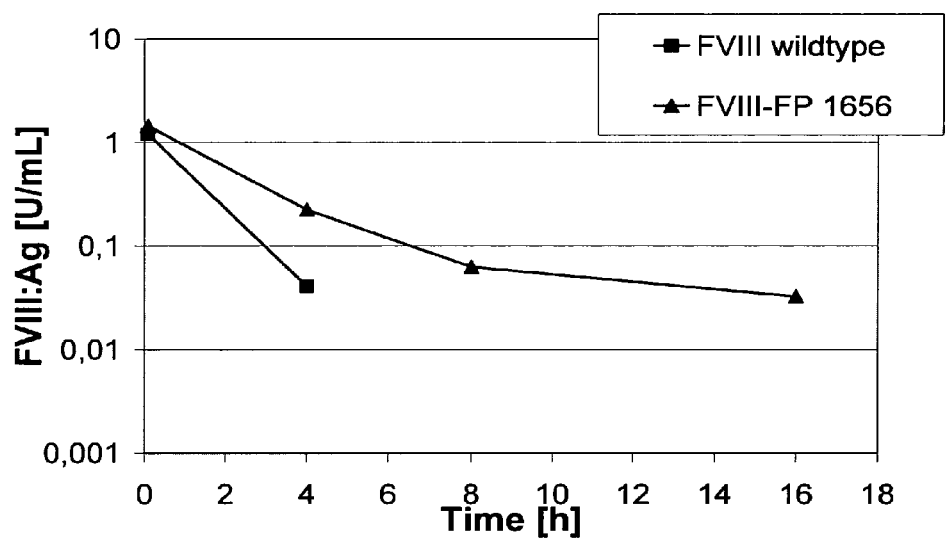

Figure 3: VWF:RCo/VWF:Ag ratios of cell culture supernatants containing wt rVWF (1570/797), rVWF-FP (1572/797) containing C-terminally linked albumin, or a mixed expression cell culture containing a mixture of wt rVWF (1570/797) and rVWF-FP (1572/797) transfected in a ratio of 5:1. Values of about 0,8 were obtained in every case that are close to 1 which is the theoretical ratio of NHP according to the unit definitions.

| Sample | VWF:RCo/VWF:Ag (U/U) |
|---|---|
| wt rVWF (1570/797) | 0,79 |
| rVWF-albumin (1572/797) | 0,90 |
| wt rVWF/rVWF-albumin (1570/1572/797) in 5:1 ratio | 0,76 |

Figure 4: SDS-Agarose gel electrophoresis of wild-type rVWF (1570/797) (B) and rVWF-FP (1572/797), both expressed in HEK cells (A). Bands were detected using either antibodies to VWF or to albumin (HSA).
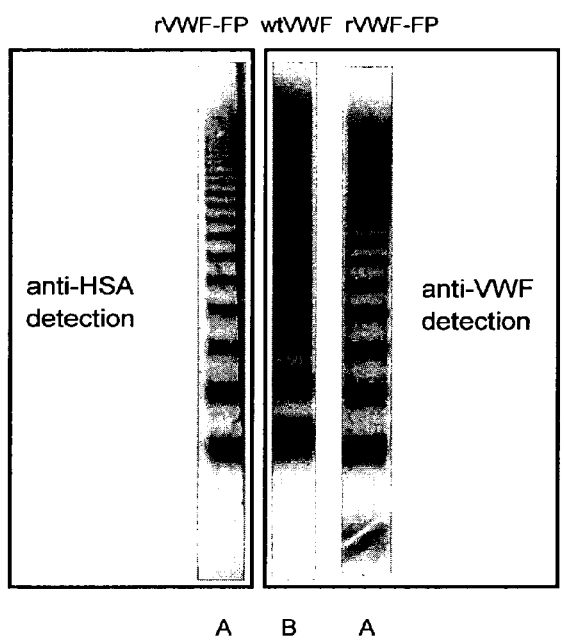
A = rVWF-FP (Expressed in presence of furin)
B = wt VWF (Expressed in presence of furin)

Figure 5: PK analysis of rVWF wt and rVWF-FP in rats based on VWF:Ag determination.
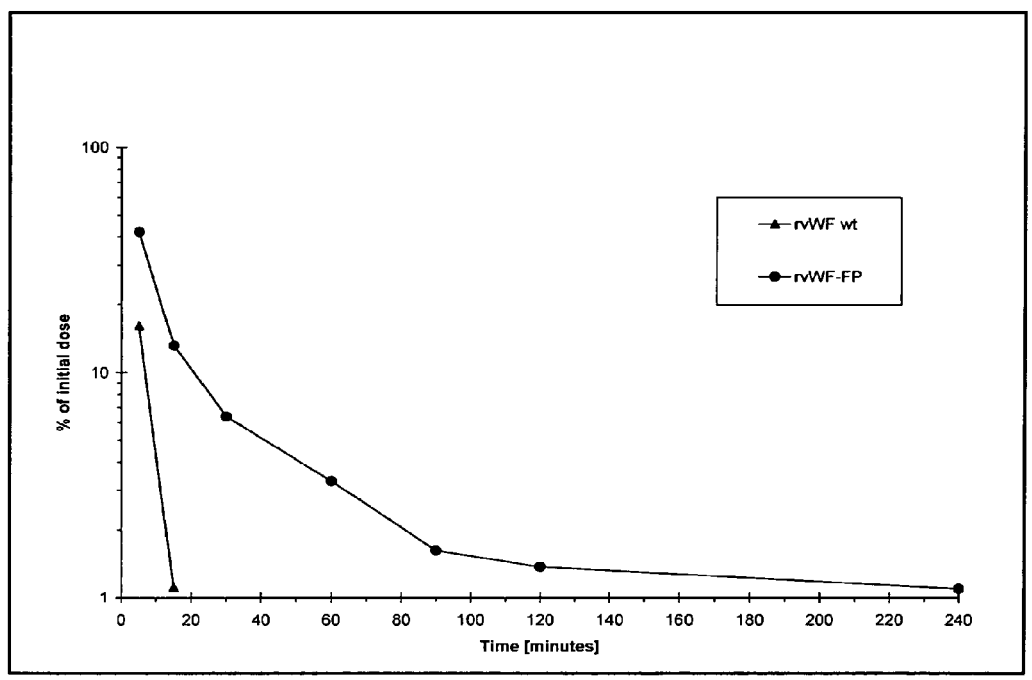

FACTOR VIII, VON WILLEBRAND FACTOR OR COMPLEXES THEREOF WITH PROLONGED IN VIVO HALF-LIFE

CROSS REFERENCE TO RELATED APPLICATIONS

This application is a continuation of U.S. application Ser. No. 13/000,938, filed Dec. 22, 2010, which is a national stage filing under 35 U.S.C. §371 of International Application No. PCT/EP2009/004549, filed on Jun. 24, 2009, and claims the benefit of priority of European Application No. 08011429.1, filed on Jun. 24, 2008. All of these applications are incorporated herein by reference in their entirety.

FIELD OF THE INVENTION

The present invention relates to modified nucleic acid sequences coding for coagulation factor VIII (FVIII) and for von Willebrand factor (VWF) as well as complexes thereof and their derivatives, recombinant expression vectors containing such nucleic acid sequences, host cells transformed with such recombinant expression vectors, recombinant polypeptides and derivatives coded for by said nucleic acid sequences which recombinant polypeptides and derivatives do have biological activities together with prolonged in vivo half-life and/or improved in vivo recovery compared to the unmodified wild-type protein. The invention also relates to corresponding FVIII sequences that result in improved expression yield. The present invention further relates to processes for the manufacture of such recombinant proteins and their derivatives. The invention also relates to a transfer vector for use in human gene therapy, which comprises such modified nucleic acid sequences.

BACKGROUND OF THE INVENTION:

There are various bleeding disorders caused by deficiencies of blood coagulation factors. The most common disorders are hemophilia A and B, resulting from deficiencies of blood coagulation factor VIII and IX, respectively. Another known bleeding disorder is von Willebrand's disease.

In plasma FVIII exists mostly as a noncovalent complex with VWF and its coagulant function is to accelerate factor IXa dependent conversion of factor X to Xa Due to the complex formation of FVIII and VWF it was assumed for a long time that FVIII and VWF functions are two functions of the same molecule. Only in the seventies it became clear that FVIII and VWF are separate molecules that form a complex under physiologic conditions. In the eighties then the dissociation constant of about 0.2 nmol/L was determined (Leyte et al., Biochem J 1989, 257: 679-683) and the DNA sequence of both molecules was studied.

Classic hemophilia or hemophilia A is an inherited bleeding disorder. It results from a chromosome X-linked deficiency of blood coagulation FVIII, and affects almost exclusively males with an incidence of between one and two individuals per 10.000. The X-chromosome defect is transmitted by female carriers who are not themselves hemophiliacs. The clinical manifestation of hemophilia A is an increased bleeding tendency. Before treatment with FVIII concentrates was introduced the mean life span for a person with severe hemophilia was less than 20 years. The use of concentrates of FVIII from plasma has considerably improved the situation for the hemophilia A patients increasing the mean life span extensively, giving most of them the possibility to live a more or less normal life. However, there have been certain problems with the plasma derived concentrates and their use, the most serious of which have been the transmission of viruses. So far, viruses causing hepatitis B, non-A non-B hepatitis and AIDS have hit the population seriously. Since then different virus inactivation methods and new highly purified FVIII concentrates have recently been developed which established a very high safety standard also for plasma derived FVIII.

The cloning of the cDNA for FVIII (Wood et al. 1984. Nature 312:330-336; Vehar et al. 1984. Nature 312:337-342) made it possible to express FVIII recombinantly leading to the development of several recombinant FVIII products, which were approved by the regulatory authorities between 1992 and 2003. The fact that the central B domain of the FVIII polypeptide chain residing between amino acids Arg-740 and Glu-1649 does not seem to be necessary for full biological activity has also led to the development of a B domain deleted FVIII.

The mature FVIII molecule consists of 2332 amino acids which can be grouped into three homologous A domains, two homologous C domains and a B Domain which are arranged in the order: A1-A2-B-A3-C1-C2. The complete amino acid sequence of mature human FVIII is shown in SEQ ID NO:15. During its secretion into plasma FVIII is processed intracellularly into a series of metal-ion linked heterodimers as single chain FVIII is cleaved at the B-A3 boundary and at different sites within the B-domain. This processing leads to heterogeneous heavy chain molecules consisting of the A1, the A2 and various parts of the B-domain which have a molecular size ranging from 90 kDa to 200 kDa. The heavy chains are bound via a metal ion to the light chains, which consist of the A3, the C1 and the C2 domain (Saenko et al. 2002. Vox Sang. 83:89-96). In plasma this heterodimeric FVIII binds with high affinity to von Willebrand Factor (VWF), which protects it from premature catabolism. The half-life of non-activated FVIII bound to VWF is about 12 hours in plasma.

Coagulation FVIII is activated via proteolytic cleavage by FXa and thrombin at amino acids Arg372 and Arg740 within the heavy chain and at Arg1689 in the light chain resulting in the release of von Willebrand Factor and generating the activated FVIII heterotrimer which will form the tenase complex on phospholipid surfaces with FIXa and FX provided that $Ca^{2+}$ is present. The heterotrimer consists of the A1 domain, a 50 kDa fragment, the A2 domain, a 43 kDa fragment and the light chain (A3-C1-C2), a 73 kDa fragment. Thus the active form of FVIII (FVIIIa) consists of an A1-subunit associated through the divalent metal ion linkage to a thrombin-cleaved A3-C1-C2 light chain and a free A2 subunit relatively loosely associated with the A1 and the A3 domain.

To avoid excessive coagulation, FVIIIa must be inactivated soon after activation. The inactivation of FVIIIa via activated Protein C (APC) by cleavage at Arg336 and Arg562 is not considered to be the major rate-limiting step. It is rather the dissociation of the non covalently attached A2 subunit from the heterotrimer which is thought to be the rate limiting step in FVIIIa inactivation after thrombin activation (Fay et al. 1991. J. Biol. Chem. 266 8957, Fay & Smudzin 1992. J. Biol. Chem; 267:13246-50). This is a rapid process, which explains the short half-life of FVIIIa in plasma, which is only 2.1 minutes (Saenko et al. 2002. Vox Sang. 83:89-96).

In severe hemophilia A patients undergoing prophylactic treatment FVIII has to be administered intravenously (i.v.) about 3 times per week due to the short plasma half-life of FVIII of about 12 to 14 hours. Each i.v. administration is cumbersome, associated with pain and entails the risk of an infection especially as this is mostly done at home by the patients themselves or by the parents of children being diagnosed for hemophilia A.

It would thus be highly desirable to create a FVIII with increased functional half-life allowing the manufacturing of pharmaceutical compositions containing FVIII, which have to be administered less frequently.

Several attempts have been made to prolong the half-life of non-activated FVIII either by reducing its interaction with cellular receptors (WO 03/093313A2, WO 021060951A2), by covalently attaching polymers to FVIII (WO 94/15625, WO 97/11957 and U.S. Pat. No. 4,970,300), by encapsulation of FVIII (WO 99/55306), by introduction of novel metal binding sites (WO 97/03193), by covalently attaching the A2 domain to the A3 domain either by peptidic (WO 97/40145 and WO 03/087355) or disulfide linkage (WO 02/103024A2) or by covalently attaching the A1 domain to the A2 domain (WO2006/108590).

Another approach to enhance the functional half-life of FVIII or VWF is by PEGylation of FVIII (WO 2007/126808, WO 2006/053299, WO 2004/075923) or by PEGylation of VWF (WO 2006/071801) which pegylated VWF by having an increased half-life would indirectly also enhance the half-life of FVIII present in plasma.

As none of the above described approaches has yet resulted in an approved FVIII pharmaceutical and as introducing mutations into the FVIII wild-type sequence or introducing chemical modifications entails at least a theoretical risk of creating immunogenic FVIII variants there is an ongoing need to develop modified coagulation factor VIII molecules which exhibit prolonged half-life.

In view of a potential thrombogenic risk it is more desirable to prolong the half-life of the non-activated form of FVIII than that of FVIIIa.

VWF, which is missing, functionally defect or only available in reduced quantity in different forms of von Willebrand disease (VWD), is a multimeric adhesive glycoprotein present in the plasma of mammals, which has multiple physiological functions. During primary hemostasis VWF acts as a mediator between specific receptors on the platelet surface and components of the extracellular matrix such as collagen. Moreover, VWF serves as a carrier and stabilizing protein for procoagulant FVIII. VWF is synthesized in endothelial cells and megakaryocytes as a 2813 amino acid precursor molecule. The amino acid sequence and the cDNA sequence of wild-type VWF are disclosed in Collins et al. 1987, Proc Natl. Acad. Sci. USA 84:4393-4397. The precursor polypeptide, pre-pro-VWF, consists of a 22-residue signal peptide, a 741-residue pro-peptide and the 2050-residue polypeptide found in mature plasma VWF (Fischer et al., FEBS Lett. 351: 345-348, 1994). After cleavage of the signal peptide in the endoplasmatic reticulum a C-terminal disulfide bridge is formed between two monomers of VWF. During further transport through the secretory pathway 12 N-linked and 10 O-linked carbohydrate side chains are added. More important, VWF dimers are multimerized via N-terminal disulfide bridges and the propeptide of 741 amino acids length is cleaved off by the enzyme PACE/furin in the late Golgi apparatus. The propeptide as well as the high-molecular-weight multimers of VWF (VWF-HMWM) are stored in the Weibel-Pallade bodies of endothelial cells or in the α-Granules of platelets.

Once secreted into plasma the protease ADAMTS13 cleaves VWF within the A1 domain of VWF. Plasma VWF therefore consists of a whole range of multimers ranging from single dimers of 500 kDa to multimers consisting of up to more than 20 dimers of a molecular weight of over 10,000 kDa. The VWF-HMWM hereby having the strongest hemostatic activity, which can be measured in ristocetin cofactor activity (VWF:RCo). The higher the ratio of VWF:RCo/VWF antigen, the higher the relative amount of high molecular weight multimers.

Defects in VWF are causal to von Willebrand disease (VWD), which is characterized by a more or less pronounced bleeding phenotype. VWD type 3 is the most severe form in which VWF is completely missing, VWD type 1 relates to a quantitative loss of VWF and its phenotype can be very mild. VWD type 2 relates to qualitative defects of VWF and can be as severe as VWD type 3. VWD type 2 has many sub forms some of them being associated with the loss or the decrease of high molecular weight multimers. Von VWD type 2a is characterized by a loss of both intermediate and large multimers. VWD type 2B is characterized by a loss of highest-molecular-weight multimers. VWD is the most frequent inherited bleeding disorder in humans and can be treated by replacement therapy with concentrates containing VWF of plasmatic or recombinant origin. VWF can be prepared from human plasma as for example described in EP 05503991. EP 0784632 describes a method for isolating recombinant VWF.

In plasma FVIII binds with high affinity to von VWF, which protects it from premature catabolism and thus, plays in addition to its role in primary hemostasis a crucial role to regulate plasma levels of FVIII and as a consequence is also a central factor to control secondary hemostasis. The half-life of non-activated FVIII bound to VWF is about 12 to 14 hours in plasma. In von Willebrand disease type 3, where no or almost no VWF is present, the half-life of FVIII is only about 6 hours, leading to symptoms of mild to moderate hemophilia A in such patients due to decreased concentrations of FVIII. The stabilizing effect of VWF on FVIII has also been used to aid recombinant expression of FVIII in CHO cells (Kaufman et al. 1989, Mol Cell Biol).

Until today the standard treatment of Hemophilia A and VWD involves frequent intravenous infusions of preparations of FVIII and VWF concentrates or of concentrates comprising a complex of FVIII and VWF derived from the plasmas of human donors or in case of FVIII that of pharmaceutical preparations based on recombinant FVIII. While these replacement therapies are generally effective, e.g. in severe hemophilia A patients undergoing prophylactic treatment FVIII has to be administered intravenously (i.v.) about 3 times per week due to the short plasma half life of FVIII of about 12 hours. Already above levels of 1% of the FVIII activity in non-hemophiliacs, e.g. by a raise of FVIII levels by 0,01 U/ml, severe hemophilia A is turned into moderate hemophilia A. In prophylactic therapy dosing regimes are designed such that the trough levels of FVIII activity do not fall below levels of 2-3% of the FVIII activity in non-hemophiliacs. Each i.v. administration is cumbersome, associated with pain and entails the risk of an infection especially as this is mostly done in home treatment by the patients themselves or by the parents of children being diagnosed for hemophilia A. In addition the frequent i.v. injections inevitably result in scar formation, interfering with future infusions. As prophylactic treatment in severe hemophilia is started early in life, with children often being less than 2 years old, it is even more difficult to inject FVIII 3 times per week into the veins of such small patients. For a limited period, implantation of port systems may offer an alternative. Despite the fact that repeated infections may occur and ports can cause inconvenience during physical exercise, they are nevertheless typically considered as favorable as compared to intravenous injections.

The in vivo half-life of human VWF in the human circulation is approximately 12 to 20 hours. In prophylactic treatment of VWD e.g. of type 3 it would also be highly desirable to find ways to prolong the functional half-life of VWF.

Another approach to enhance the functional half-life of VWF is by PEGylation (WO 2006/071801) which pegylated VWF by having an increased half-life would indirectly also enhance the half-life of FVIII present in plasma.

However the chemical conjugation of PEG or other molecules to therapeutic proteins always entails the risk, that the specific activity is reduced due to shielding of important interaction sites with other proteins, chemical conjugation adds an additional step in the manufacture of such proteins decreasing final yields and making manufacture more expensive. Also the long term effects on human health are not known as currently known PEGylated therapeutic proteins do not need to be administrated lifelong as it would be the case for a VWF to be administered in prophylaxis of von Willebrand disease or in for a FVIII to be administered in hemophilia A.

It would thus be highly desirable to obtain a long-lived VWF which is not chemically modified.

In the prior art fusions of coagulation factors to albumin (WO 01/79271), alpha-fetoprotein (WO 2005/024044) and immunoglobulin (WO 2004/101740) as half-life enhancing polypeptides have been described. These were taught to be attached to the carboxy- or the amino-terminus or to both termini of the respective therapeutic protein moiety, occasionally linked by peptidic linkers, preferably by linkers consisting of glycine and serine.

Ballance et al. (WO 01/79271) described N- or C-terminal fusion polypeptides of a multitude of different therapeutic polypeptides fused to human serum albumin. Long lists of potential fusion partners are described without disclosing experimental data for almost any of these polypeptides whether or not the respective albumin fusion proteins actually retain biological activity and have improved properties. Among said list of therapeutic polypeptides also FVIII and VWF are mentioned.

A C-terminal fusion would not have been seriously considered by the man skilled in the art as the C2 domain of FVIII at the very C-terminal part of FVIII between amino acid 2303 and 2332 of FVIII comprises a platelet membrane binding site which is essential for FVIII function. This is why there are many amino acid mutations known in this region which lead to hemophilia A. It was thus surprising that a relatively large heterologous polypeptide like albumin can be fused to the C-terminal part of FVIII without preventing FVIII function by preventing platelet binding. In addition, the C2 domain also contains a binding site for VWF. This site together with the amino acid sequence 1649-1689 is responsible for the high affinity binding of FVIII to VWF. Therefore, a man skilled in the art would also not have expected that a FVIII with a C-terminal albumin fusion would retain its binding to VWF.

It was surprisingly found that in contrast to the prediction by Ballance et al. an albumin fusion to the N-terminus of FVIII was not secreted into the culture medium. Therefore and because of the reasons detailed above it was now even more surprisingly found that a FVIII fused at its C-terminal part to albumin is secreted into the culture medium and retains its biological function including binding to membranes of activated platelets and to VWF.

It was also surprising to find that the modified FVIII of the invention shows an increase of in vivo recovery by about 20% compared to the wild type FVIII.

A man skilled in the art would also not have considered fusing human albumin to the N- or the C-terminus of VWF. In an N-terminal fusion the albumin part would be cleaved off during propeptide processing. Or if the propeptide would be omitted the multimerization would not take place. As detailed above the C-terminus of VWF is essential for the initial dimerization and secretion as shown by Schneppenheim et al. (Schneppenheim R. et al. 1996. Defective dimerization of VWF subunits due to a Cys to Arg mutation in VWD type IID. Proc Natl Acad Sci USA 93:3581-3586; Schneppenheim R. et al. 2001. Expression and characterization of VWF dimerization defects in different types of VWD. Blood 97:2059-2066.), Baronciani et al. (Baronciani L.et al. 2000. Molecular characterization of a multiethnic group of 21 patients with VWD type 3. Thromb. Haemost 84:536-540), Enayat et al. (Enayat MS et al. 2001. Aberrant dimerization of VWF as the result of mutations in the carboxy-terminal region: identification of 3 mutations in members of 3 different families with type 2A (phenotype IID) VWD. Blood 98:674-680) and Tjernberg et al. 2006. Homozygous C2362F VWF induces intracellular retention of mutant VWF resulting in autosomal recessive severe VWD. Br J Haematol. 133:409-418). Therefore the man skilled in the art would not consider fusing a large protein like human albumin to the C- or N-terminus of VWF as he would expect that normal dimerization or multimerization of VWF would be impaired. As the higher multimers of VWF are the ones most active in primary hemostasis the man skilled in the art would have looked for other ways to prolong the functional half-life of VWF.

It was now surprisingly found that fusing heterologous polypeptides such as albumin to the C-terminal part of VWF, not only permits expression and secretion of VWF chimeric proteins from mammalian cells but also results in modified VWF molecules that retain significant VWF activity and form high molecular weight multimers. In addition, such modified VWF molecules exhibit prolonged in vivo half-life and/or improved in vivo recovery.

DESCRIPTION OF THE INVENTION

It is an objective of this invention to provide a modified FVIII or a modified VWF as well as complexes of modified FVIII with non-modified VWF, complexes of non-modified FVIII with modified VWF and also complexes of modified FVIII with modified VWF with enhanced in vivo half-life.

The term "modified FVIII" or "modified VWF" in the sense of the invention means FVIII or VWF polypeptides which are fused to half-life enhancing polypeptides, encompassing also natural alleles, variants, deletions and insertions of FVIII or VWF.

It is another objective of this invention to provide a modified FVIII or a modified VWF as well as complexes of modified FVIII with non-modified VWF, complexes of non-modified FVIII with modified VWF and also complexes of modified FVIII with modified VWF with improved in vivo recovery.

Another objective of the invention is that this modified FVIII or modified VWF as well as complexes of modified FVIII with non-modified VWF, non-modified FVIII with modified VWF and also complexes of modified FVIII with modified VWF can be expressed by mammalian cells and retain their respective biological activities.

In summary, surprisingly the modified FVIII or modified VWF as well as complexes of modified FVIII with non-modified VWF, complexes of non-modified FVIII with modified VWF and also complexes of modified FVIII with modified VWF of the invention have retained biological activity, increased in vivo half-life and in vivo recovery.

An additional potential benefit of those embodiments of the present invention in which the FVIII is modified and in which the A2 domain remains only non covalently attached to the A3 domain after activation is that only the half-life of the non-activated form of FVIII is increased, whereas the half-life of the activated form of FVIII remains essentially the same, which might result in a decreased risk of thrombogenicity as compared to FVIII variants which lead to a stabilization of the activated form of FVIII.

The modified FVIII or modified VWF as well as complexes of modified FVIII with non-modified VWF, complexes of non-modified FVIII with modified VWF and also complexes of modified FVIII with modified VWF molecules of the invention can be generated by fusing a half-life enhancing protein (HLEP) moiety to the C-terminal part of FVIII or to the C-terminal part of VWF.

HLEPs in the sense of the present invention are selected from a group consisting of members of the albumin family, which includes albumin, afamin, alpha-fetoprotein and the vitamin D binding protein, as well as portions of an immunoglobulin constant region and polypeptides capable of binding under physiological conditions to members of the albumin family as well as to portions of an immunoglobulin constant region. The most preferred HLEP is human albumin.

The present invention therefore relates to a modified FVIII or modified VWF as well as complexes of modified FVIII with non-modified VWF, complexes of non-modified FVIII with modified VWF and also complexes of modified FVIII with modified VWF having at the C-terminal part of the modified FVIII and/or VWF a fusion to a HLEP, characterized in that the modified FVIII or modified VWF as well as the complex of modified FVIII with non-modified VWF, the complex of non-modified FVIII with modified VWF or the complex of modified FVIII with modified VWF has prolonged functional half-life compared to the functional half-life of the wild-type FVIII or wild-type VWF or the complex of wild-type VWF and wild-type FVIII.

The present invention also relates to C-terminal fusions to more than one HLEP wherein the HLEP, which is fused several times, may be the same HLEP or may be a combination of different HLEPs.

The present invention also relates to a modified FVIII having at the C-terminal part a fusion to a HLEP, characterized in that the modified FVIII or modified VWF or the complex of modified FVIII with non-modified VWF, the complex of non-modified FVIII with modified VWF or the complex of modified FVIII with modified VWF has improved in vivo recovery compared to the in vivo recovery of the wild-type FVIII or wild-type VWF or the complex of wild-type VWF and wild-type FVIII.

Another embodiment of the invention are modified FVIII polypeptides having at the C-terminal part a fusion to a HLEP, characterized in that the modified FVIII is secreted into a fermentation medium at a higher yield as a wild-type FVIII.

Another aspect of the invention are polynucleotides or combinations of polynucleotides encoding the modified FVIII and/or the modified VWF.

The invention further relates to plasmids or vectors comprising a polynucleotide described herein, to host cells comprising a polynucleotide or a plasmid or vector described herein.

Another aspect of the invention is a method of producing a modified FVIII or a modified VWF or a complex of modified FVIII with non-modified VWF, a complex of non-modified FVIII with modified VWF or a complex of modified FVIII with modified VWF, comprising:
  (a) culturing host cells of the invention under conditions such that the modified coagulation factor is expressed; and
  (b) optionally recovering the modified coagulation factor from the host cells or from the culture medium.

The invention further pertains to pharmaceutical compositions comprising a modified FVIII or a modified VWF or a complex of modified FVIII with non-modified VWF or a complex of non-modified FVIII with modified VWF or a complex of modified FVIII with modified VWF, a polynucleotide, or a plasmid or vector described herein.

Yet another aspect of the invention is the use of a modified FVIII or a modified VWF or a complex of modified FVIII with non-modified VWF or a complex of non-modified FVIII with modified VWF or a complex of modified FVIII with modified VWF, one or more polynucleotides, or one or more plasmids or vectors, or of host cells according to this invention for the manufacture of a medicament for the treatment or prevention of a blood coagulation disorder.

DETAILED DESCRIPTION OF THE INVENTION

The invention pertains to a complex comprising FVIII and von VWF or one of its individual polypeptidic components wherein at least one polypeptidic component of said complex is fused at the C-terminal part of its primary translation product to the N-terminal part of a half-life enhancing polypeptide (HLEP)

The invention also pertains to a modified FVIII or a modified VWF or a complex comprising modified FVIII and non-modified VWF or a complex comprising non-modified FVIII and modified VWF or a complex comprising modified FVIII and modified VWF wherein the modified FVIII is fused at a C-terminal part of the primary translation polypeptide of FVIII to the N-terminal part of a HLEP or the modified VWF is fused at a C-terminal part of the primary translation polypeptide of VWF to the N-terminal part acid of a HLEP.

In preferred embodiments the invention pertains to a modified FVIII or a modified VWF or a complex comprising modified FVIII and non-modified VWF or a complex comprising non-modified FVIII and modified VWF or a complex comprising modified FVIII and modified VWF, wherein
  a. the modified FVIII has a prolonged functional half-life compared to the functional half-life of wild-type FVIII or
  b. the modified VWF has a prolonged functional half-life compared to the functional half-life of wild-type VWF or
  c. the complex comprising modified FVIII and non-modified VWF has a prolonged functional half-life compared to the functional half-life of the corresponding complex comprising wild-type FVIII and wild-type VWF or
  d. the complex comprising non-modified FVIII and modified VWF has a prolonged functional half-life compared to the functional half-life of the corresponding complex comprising wild-type FVIII and wild-type VWF or
  e. the complex of modified FVIII with modified VWF has a prolonged functional half-life compared to the functional half-life of the corresponding complex comprising wild-type FVIII and wild-type VWF.

A preferred embodiment of the invention is a modified polypeptide or a complex comprising said modified polypeptide or a complex comprising said modified polypeptides as described above, wherein the modified polypeptide has a functional half-life increased by at least 25% as compared to the functional half-life of the corresponding wild-type polypeptide or the complex comprising said modified polypeptide or a complex comprising said modified polypeptides has a functional half-life increased by at least 25% as compared to the corresponding complex of wild-type FVIII and wild-type VWF.

Another embodiment of the invention is a modified FVIII or a modified VWF or a complex comprising modified FVIII and non-modified VWF or a complex comprising non-modified FVIII and modified VWF or a complex comprising modified FVIII and modified VWF, wherein
  a. the modified FVIII has a prolonged antigen half-life compared to the antigen half-life of wild-type FVIII or
  b. the modified VWF has a prolonged antigen half-life compared to the antigen half-life of wild-type VWF or
  c. the complex comprising modified FVIII and non-modified VWF has a prolonged antigen half-life compared to the antigen half-life of the corresponding complex comprising wild-type FVIII and wild-type VWF or
  d. the complex comprising non-modified FVIII and modified VWF has a prolonged antigen half-life compared to the antigen half-life of the corresponding complex of wild-type FVIII and wild-type VWF or
  e. the complex comprising modified FVIII and modified VWF has a prolonged antigen half-life compared to the antigen half-life of the corresponding complex of wild-type FVIII and wild-type VWF.

A preferred embodiment of the invention is a modified polypeptide or a complex comprising said modified polypeptide or a complex comprising said modified polypeptides as described above, wherein the modified polypeptide has an antigen half-life increased by at least 25% as compared to the antigen half-life of the corresponding wild-type polypeptide or the complex comprising said modified polypeptide or a complex comprising said modified polypeptides has an antigen half-life increased by at least 25% as compared to the corresponding complex of wild-type FVIII and wild-type VWF.

Still another embodiment of the invention is a modified FVIII or a modified VWF or a complex comprising modified FVIII and non-modified VWF or a complex comprising non-modified FVIII and modified VWF or a complex comprising modified FVIII and modified VWF, wherein
  a. the modified FVIII has an increased in vivo recovery compared to the in vivo recovery of wild-type FVIII or
  b. the modified VWF has an increased in vivo recovery compared to the in vivo recovery of wild-type VWF or
  c. the complex comprising modified FVIII and non-modified VWF has an increased in vivo recovery compared to the in vivo recovery of the corresponding complex comprising wild-type FVIII and wild-type VWF or
  d. the complex comprising non-modified FVIII and modified VWF has an increased in vivo recovery compared to the in vivo recovery of the corresponding complex comprising wild-type FVIII and wild-type VWF or
  e. the complex comprising modified FVIII and modified VWF has an increased in vivo recovery compared to the in vivo recovery of the corresponding complex comprising wild-type FVIII and wild-type VWF.

Another preferred embodiment of the invention is a modified polypeptide or a complex comprising said modified polypeptide or a complex comprising said modified polypeptides as described above, wherein the modified polypeptide has an in vivo recovery increased by at least 10% as compared to the in vivo recovery of the corresponding wild-type polypeptide or the complex comprising said modified polypeptide or a complex comprising said modified polypeptides has an in vivo recovery increased by at least 10% as compared to the corresponding complex of wild-type FVIII and wild-type VWF.

Another preferred embodiment of the invention is
  a) a modified polypeptide or a complex comprising said modified polypeptide or a complex comprising said modified polypeptides as described above, wherein at least one polypeptidic component of said complex is fused at the C-terminal amino acid of its primary translation product to the N-terminal part of a HLEP or
  b) a modified polypeptide or a complex comprising said modified polypeptide or a complex comprising said modified polypeptides as described above, wherein at least one polypeptidic component of said complex is fused at the C-terminal part of its primary translation product to the N-terminal amino acid of a HLEP or
  c) a modified polypeptide or a complex comprising said modified polypeptide or a complex comprising said modified polypeptides as described above, wherein at least one polypeptidic component of said complex is fused at the C-terminal amino acid of its primary translation product to the N-terminal amino acid of a HLEP.

Another preferred embodiment of the invention is a modified polypeptide or a complex comprising said modified polypeptide or a complex comprising said modified polypeptides as described above, wherein the modified polypeptide has at least 10% of the biological activity of wild-type polypeptide or the complex comprising the modified polypeptide or a complex comprising said modified polypeptides has at least 10% of the biological activity of the corresponding complex of wild-type FVIII and wild-type VWF.

Also comprised in the present invention is a method of preparing a modified FVIII or a modified VWF having increased functional half-life, comprising fusing the N-terminal part of a half-life-enhancing polypeptide to a C-terminal part of the primary translation polypeptide of the FVIII or to a C-terminal part of the primary translation polypeptide of the VWF as well as a method of preparing a complex comprising modified FVIII and non-modified VWF or a complex comprising non-modified FVIII and modified VWF or a complex comprising modified FVIII and modified VWF by mixing a modified FVIII prepared by the method described above with wild-type VWF or by mixing wild-type FVIII with a modified VWF prepared by the method described above or by mixing a modified FVIII and a modified VWF prepared by the method described above.

Also encompassed in the invention is the use of
  a. a modified FVIII as prepared by the method described above and wild-type VWF or
  b. a wild-type FVIII and a modified VWF prepared by the method described above or
  c. a modified FVIII a as prepared by the method described above and a modified VWF as prepared by the method described above
for the manufacture of a combined pharmaceutical preparation for simultaneous, separate or sequential use in the therapy of bleeding disorders, preferentially in the therapy of hemophilia A and/or von Willebrand disease.

The "functional half-life" according to the present invention is the half-life of the biological activity of the modified FVIII or the modified VWF or a complex of modified FVIII with non-modified VWF or a complex of the non-modified FVIII with modified VWF or a complex of modified FVIII with modified VWF once it has been administered to a mammal and can be measured in vitro in blood samples taken at different time intervals from said mammal after the modified FVIII or the modified VWF or the complex of modified FVIII with non-modified VWF or the complex of non-modified FVIII with modified VWF or the complex of modified FVIII with modified VWF has been administered.

The phrases "fusing" or "fused" refer to the addition of amino acids to the C-terminal part of FVIII and/or to the C-terminal part of VWF. When referring herein to a "fusion to the C-terminal amino acid of FVIII" or to a "fusion to the C-terminal amino acid of VWF" this means a fusion exactly to the C-terminal amino acid of FVIII at amino acid 2332 of the mature wild-type FVIII cDNA sequence or exactly to the C-terminal amino acid of VWF at amino acid 2050 of wild-type mature VWF. Mature FVIII or mature VWF meaning the respective polypeptide after cleavage of the propeptide. However the invention also encompasses a "fusion to the C-terminal part of FVIII" or a "fusion to the C-terminal part of VWF" in the sense of this invention may also include a fusion to a FVIII and/or VWF molecule respectively in which one or more amino acid position up to n amino acids from the C-terminal amino acid of FVIII and/or of VWF are deleted. The figure n is an integer that should not be greater than 5%, preferably not greater than 1% of the total number of amino acids of the FVIII and/or VWF. Usually, n is 20, preferably 15, more preferably 10, still more preferably 5 or less (e.g. 1, 2, 3, 4 or 5).

In one embodiment, the modified FVIII has the following structure:

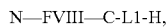  N—FVIII—C-L1-H, [formula 1]

wherein
N is an N-terminal part of FVIII,
L1 is a chemical bond or a linker sequence
H is a HLEP, and
C is a C-terminal part of FVIII In another embodiment the modified VWF has the following structure:

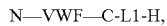  N—VWF—C-L1-H, [formula 2]

wherein
N is an N-terminal part of VWF,
L1 is a chemical bond or a linker sequence
H is a HLEP, and
C is a C-terminal part of VWF L1 may be a chemical bond or a linker sequence consisting of one or more amino acids, e.g. of 1 to 20, 1 to 15, 1 to 10, 1 to 5 or 1 to 3 (e.g. 1, 2 or 3) amino acids and which may be equal or different from each other. Usually, the linker sequences are not present at the corresponding position in the wild-type coagulation factor. Examples of suitable amino acids present in L1 include Gly and Ser.

Preferred HLEP sequences are described infra. Likewise encompassed by the invention are fusions to the exact "N-terminal amino acid" of the respective HLEP, or fusions to the "N-terminal part" of the respective HLEP, which includes N-terminal deletions of one or more amino acids of the HLEP.

The modified FVIII or the modified VWF or the complex of the modified FVIII with the non-modified VWF, the complex of the non-modified FVIII with the modified VWF or the complex of the modified FVIII with modified VWF of the invention may comprise more than one HLEP sequence, e.g. two or three HLEP sequences. These multiple HLEP sequences may be fused to the C-terminal part of FVIII and/or to the C-terminal part of VWF in tandem, e.g. as successive repeats.

FVIII may be processed proteolytically at various stages. For example, as mentioned supra, during its secretion into plasma single chain FVIII is cleaved intracellularly at the B-A3 boundary and at different sites within the B-domain. The heavy chain is bound via a metal ion to the light chain having the domain structure A3-C1-C2. FVIII is activated via proteolytic cleavage at amino acids Arg372 and Arg740 within the heavy chain and at Arg1689 in the light chain generating the activated FVIII heterotrimer consisting of the A1 domain, the A2 domain, and the light chain (A3-C1-C2), a 73 kDa fragment. Thus the active form of FVIII (FVIIIa) consists of an A1-subunit associated through the divalent metal ion linkage to a thrombin-cleaved A3-C1-C2 light chain and a free A2 subunit relatively loosely associated with the A1 and the A3 domain.

Accordingly, the present invention encompasses also modified FVIII that is not present as a single chain polypeptide but consists of several polypeptides (e.g. one or two or three) that are associated with each other via non-covalent linkages.

Preferably N—FVIII—C comprises the full length sequence of FVIII. Also encompassed are N-terminal, C-terminal or internal deletions of FVIII as long as the biological activity of FVIII is retained. The biological activity is retained in the sense of the invention if the FVIII with deletions retains at least 10%, preferably at least 25%, more preferably at least 50%, most preferably at least 75% of the biological activity of wild-type FVIII. The biological activity of FVIII can be determined by the artisan as described below.

A suitable test to determine the biological activity of FVIII is for example the one stage or the two stage coagulation assay (Rizza et al. 1982. Coagulation assay of FVIII:C and FIXa in Bloom ed. The Hemophilias. NY Churchchill Livingston 1992) or the chromogenic substrate FVIII:C assay (S. Rosen, 1984. Scand J Haematol 33: 139-145, suppl.). The content of these references is incorporated herein by reference. The cDNA sequence and the amino acid sequence of the mature wild-type form of human blood coagulation FVIII are shown in SEQ ID NO:14 and SEQ ID NO:15, respectively. The reference to an amino acid position of a specific sequence means the position of said amino acid in the FVIII wild-type protein and does not exclude the presence of mutations, e.g. deletions, insertions and/or substitutions at other positions in the sequence referred to. For example, a mutation in "Glu2004" referring to SEQ ID NO:15 does not exclude that in the modified homologue one or more amino acids at positions 1 through 2332 of SEQ ID NO:15 are missing.

The terms "blood coagulation Factor VIII", "Factor VIII" and "FVIII" are used interchangeably herein. "Blood coagulation Factor VIII" includes wild-type blood coagulation FVIII as well as derivatives of wild-type blood coagulation FVIII having the procoagulant activity of wild-type blood coagulation FVIII. Derivatives may have deletions, insertions and/or additions compared with the amino acid sequence of wild-type FVIII. The term FVIII includes proteolytically processed forms of FVIII, e.g. the form before activation, comprising heavy chain and light chain.

The term "FVIII" includes any FVIII variants or mutants having at least 25%, more preferably at least 50%, most preferably at least 75% of the biological activity of wild-type factor VIII.

As non-limiting examples, FVIII molecules include FVIII mutants preventing or reducing APC cleavage (Amano 1998. Thromb. Haemost. 79:557-563), FVIII mutants further stabilizing the A2 domain (WO 97/40145), FVIII mutants resulting in increased expression (Swaroop et al. 1997. JBC 272: 24121-24124), FVIII mutants reducing its immunogenicity (Lollar 1999. Thromb. Haemost. 82:505-508), FVIII reconstituted from differently expressed heavy and light chains (Oh et al. 1999. Exp. Mol. Med. 31:95-100), FVIII mutants reducing binding to receptors leading to catabolism of FVIII like HSPG (heparan sulfate proteoglycans) and/or LRP (low density lipoprotein receptor related protein) (Ananyeva et al. 2001. TCM, 11:251-257), disulfide bond-stabilized FVIII variants (Gale et al., 2006. J. Thromb. Hemost. 4:1315-1322), FVIII mutants with improved secretion properties (Miao et al., 2004. Blood 103:3412-3419), FVIII mutants with increased cofactor specific activity (Wakabayashi et al., 2005. Biochemistry 44:10298-304), FVIII mutants with improved biosynthesis and secretion, reduced ER chaperone interaction, improved ER-Golgi transport, increased activation or resistance to inactivation and improved half-life (summarized by Pipe 2004. Sem. Thromb. Hemost. 30:227-237). All of these FVIII mutants and variants are incorporated herein by reference in their entirety.

VWF may be processed proteolytically at various stages. For example, as mentioned supra, the protease ADAMTS13 cleaves VWF within the A2 domain of VWF. Accordingly, the present invention encompasses also modified VWF which has been cleaved proteolytically e.g. by ADAMTS13. Such cleavage would result in multimeric chains of VWF which comprise at their ends at least one or at most two monomers of VWF which have been cleaved by ADAMTS 13.

Preferably N—VWF—C comprises the full length sequence of VWF. Also encompassed are N-terminal, C-terminal or internal deletions of VWF as long as the biological activity of VWF is retained. The biological activity is retained in the sense of the invention if the VWF with deletions retains at least 10%, preferably at least 25%, more preferably at least 50%, most preferably at least 75% of the biological activity of wild-type VWF. The biological activity of wild-type VWF can be determined by the artisan using methods for ristocetin co-factor activity (Federici AB et al. 2004. Haematologica 89:77-85), binding of VWF to GP Iba of the platelet glycoprotein complex lb-V-IX (Sucker et al. 2006. Clin Appl Thromb Hemost. 12:305-310), or a collagen binding assay (Kailas & Talpsep. 2001. Annals of Hematology 80:466-471).

"FVIII" and/or "VWF" within the above definition also include natural allelic variations that may exist and occur from one individual to another. "FVIII" and/or "VWF" within the above definition further includes variants of FVIII and or VWF. Such variants differ in one or more amino acid residues from the wild-type sequence. Examples of such differences may include as conservative amino acid substitutions, i.e. substitutions within groups of amino acids with similar characteristics, e.g. (1) small amino acids, (2) acidic amino acids, (3) polar amino acids, (4) basic amino acids, (5) hydrophobic amino acids, and (6) aromatic amino acids. Examples of such conservative substitutions are shown in the following table.

TABLE 1

| | | | |
|---|---|---|---|
| (1) Alanine | Glycine | | |
| (2) Aspartic acid | Glutamic acid | | |
| (3) Asparagine | Glutamine | Serine | Threonine |
| (4) Arginine | Histidine | Lysine | |
| (5) Isoleucine | Leucine | Methionine | Valine |
| (6) Phenylalanine | Tyrosine | Tryptophane | |

One or more HLEPs may fused to the C-terminal part of FVIII preferably as not to interfere with the binding capabilities of FVIII for example to VWF, platelets or FIX.

One or more HLEPs may be fused to the C-terminal part of VWF preferably as not to interfere with the binding capabilities of VWF for example to FVIII, platelets, heparin or collagen.

Once FVIII is endogenously activated during coagulation in vivo, it may be no longer desirable to maintain the increased functional half-life of the now activated FVIII as this might lead to thrombotic complications what is already the case for a wild-type activated coagulation factor as FVIIa (Aledort 2004. J Thromb Haemost 2:1700-1708) and what may be more relevant if the activated factor would have an increased functional half-life. It is therefore another objective of the present invention to provide long-lived FVIII molecules, which after endogenous activation in vivo or after availability of a cofactor do have a functional half-life comparable to that of unmodified FVIII. This can by way of non-limiting example be achieved by introducing a cleavage site for example for a coagulation factor between the C-terminal part of FVIII and the HLEP. With such FVIII-HLEP connecting sequences the activation of the FVIII chimeric protein of the invention will lead to a concomitant complete separation of FVIIIa from the HLEP moiety. Accordingly, in one embodiment, the functional half-life of the endogenously activated modified FVIII is substantially the same as that of the activated wild-type FVIII (e.g. ±15%, preferably ±10%).

In yet another embodiment of the invention, however, one or more of the proteolytical cleavage sites, preferably the thrombin cleavage sites at Arg740 and/or Arg372, are mutated or deleted in order to prevent cleavage and result in an insertion protein which displays improved properties like enhanced functional half-life even as an activated molecule.

In another embodiment of the invention the FVIII proteins of the invention may be expressed as two separate chains (see infra).

The modified FVIII according to this invention may be a single chain polypeptide, or it may be composed of two or three polypeptide chains that are associated via non-covalent linkages, due to proteolytic processing.

In another embodiment of the invention, the amino acids at or near the PACE/Furin cleavage site (Arg1648) are mutated or deleted in order to prevent cleavage by PACE/Furin. This is thought to result in a one-chain FVIII/HLEP fusion molecule with improved half-life.

In one embodiment of the invention, the modified FVIII of the invention exhibits an increased functional half-life compared to the corresponding FVIII form containing no integrated HLEP and/or to the wild-type form FVIII. The functional half-life e.g. can be determined in vivo in animal models of hemophilia A, like FVIII knockout mice, in which one would expect a longer lasting hemostatic effect as compared to wild-type FVIII. The hemostatic effect could be tested for example by determining time to arrest of bleeding after a tail clip.

The functional half-life in one embodiment of the invention is the half-life of the biological activity of the FVIII once it has been administered to a mammal and is measured in vitro. The functional half-life of the modified FVIII according to the invention is greater than that of the FVIII lacking the modification as tested in the same species. The functional half-life is preferably increased by at least 10%, preferably 25%, more preferably by at least 50%, and even more preferably by at least 100% compared to the wild-type form of FVIII.

The functional half-life of a modified FVIII comprising a HLEP modification, can be determined by administering the respective modified FVIII (and in comparison wild-type FVIII) to rats, rabbits or other experimental animal species intravenously or subcutaneously and following the elimination of the biological activity of said modified or respectively non-modified coagulation factor in blood samples drawn at appropriate intervals after application. Suitable test methods are the activity tests described herein.

The functional half-life according to another embodiment of the invention is the half-life of the biological function of the VWF once it has been administered to a mammal and is measured in vitro. The functional half-life of the modified VWF according to the invention is greater than that of the VWF lacking the modification as tested in the same species. The functional half-life is increased by at least 10%, preferably increased by at least 25%, more preferably by at least 50%, and even more preferably by at least 100% compared to the VWF lacking the modification and/or to the wild-type form of VWF.

The functional half-life of a modified VWF comprising a HLEP modification, can be determined by administering the respective modified VWF (and in comparison that of the non-modified VWF) to rats, rabbits or other experimental animal species intravenously or subcutaneously and following the elimination of the biological activity of said modified or respectively non-modified VWF in blood samples drawn at appropriate intervals after application. Suitable test methods are the activity tests described herein.

As a surrogate marker for the half-life of biological activity also the levels of antigen of the modified or respectively wild-type FVIII or the levels of antigen of the modified or respectively wild-type VWF can be measured. Thus also encompassed by the invention are modified FVIII and/or VWF molecules having at the C-terminal part of FVIII and/or VWF a fusion to a HLEP, characterized in that the modified FVIII or the modified VWF or the modified FVIII or the complex of modified FVIII with non-modified VWF, or the complex of the non-modified FVIII with modified VWF or the complex of modified FVIII with modified VWF has a prolonged half-life of the FVIII and/or VWF antigen compared to the half-life of the FVIII and/or VWF antigen lacking said insertion. The "half-life of the FVIII antigen" according to the present invention is the half-life of the antigen of the FVIII once it has been administered to a mammal and is measured in vitro. The "half-life of the VWF antigen" according to the present invention is the half-life of the antigen of the VWF once it has been administered to a mammal and is measured in vitro. Antigen test methods based on specific antibodies in an enzyme immunoassay format as known to the artisan and commercially available (e.g. Dade Behring, Instrumentation Laboratory, Abbott Laboratories, Diagnostica Stago). Functional and antigen half-lives can be calculated using the time points of the beta phase of elimination according to the formula $t_{1/2}=\ln 2/k$, whereas k is the slope of the regression line.

In another embodiment, the functional half-life of the endogenously activated modified FVIII is prolonged compared to that of the activated wild-type FVIII. The increase may be more than 15%, for example at least 20% or at least 50%. Again, such functional half-life values can be measured and calculated as described for functional half-lives supra. Increased half-lives of the endogenously activated modified FVIII molecules may be beneficial in situations were only very low levels of FVIII are available that therefore are not thrombogenic. Such situations may occur e.g. upon gene therapy treatment where often only low expression rates can be achieved. Therefore, such stabilized FVIII molecules might be beneficial in e.g. gene therapy despite a thrombogenic risk connected to such FVIII molecules if administered as proteins in high or physiologic doses.

In another embodiment of the invention, the modified FVIII of the invention exhibits an improved in vivo recovery compared to the wild-type FVIII and the modified VWF of the invention exhibits an improved in vivo recovery compared to the wild-type VWF. The in vivo recovery can be determined in vivo for example in normal animals or in animal models of hemophilia A, like FVIII knockout mice, or in models of VWD, like VWF knockout mice in which one would expect an increased percentage of the modified FVIII or VWF of the invention be found by antigen or activity assays in the circulation shortly (5 to 10 min.) after i.v. administration compared to the corresponding wild-type FVIII or wild-type VWF.

The in vivo recovery is preferably increased by at least 10%, more preferably by at least 20%, and even more preferably by at least 40% compared to wild-type form FVIII or to wild-type VWF.

In yet another embodiment of the invention immunoglobulin constant regions or portions thereof are used as HLEPs. Preferably the Fc region comprised of a CH2 and CH3 domain and a hinge region of an IgG, more preferably of an IgG1 or fragments or variants thereof are used, variants including mutations which enhance binding to the neonatal Fc receptor (FcRn).

It is another objective of the present invention to provide long-lived FVIII molecules, which after proteolytic processing in vivo do have a functional half-life comparable to that of an unmodified FVIII. This can be achieved by maintaining certain cleavage sites in the modified FVIII leading to a proteolytic cleavage for example when in contact with activated coagulation factors, which separates the FVIII from the HLEP. Accordingly, in one embodiment, the functional half-life of the proteolytically processed modified FVIII is substantially the same as that of the non-modified VWF lacking the modification, and/or it is substantially the same as that of the wild-type VWF (e.g. ±15%, preferably ±10%).

Still another embodiment of the invention are modified FVIII polypeptides which are fused to a HLEP for example albumin at the C-terminal part of the FVIII molecule which do have reduced binding to VWF or do not bind VWF at all.

It is another objective of the present invention to provide long-lived VWF molecules, which after proteolytic processing in vivo do have functional properties comparable to that of an unmodified VWF. This can be achieved by maintaining or inserting certain cleavage sites in the modified VWF (see infra) leading to a proteolytic cleavage for example when in contact with activated coagulation factors, which separates the VWF from the HLEP. Accordingly, in one embodiment, the functional half-life of the proteolytically processed modified VWF is substantially the same as that of the non-modified VWF lacking the modification, and/or it is substantially the same as that of the wild-type VWF (e.g. ±15%, preferably ±10%).

Another preferred embodiment of the invention is a coexpression of wild-type VWF and a modified VWF according to the invention resulting in VWF multimers comprising non-modified as well as modified VWF monomers.

Linker Sequences

According to this invention, the therapeutic polypeptide moiety may be coupled to the HLEP moiety by a peptide linker. The linker should be non-immunogenic and may be a non-cleavable or cleavable linker.

Non-cleavable linkers may be comprised of alternating glycine and serine residues as exemplified in WO2007/090584.

In another embodiment of the invention the peptidic linker between the FVIII and/or the VWF moiety and the albumin moiety consists of peptide sequences, which serve as natural interdomain linkers in human proteins. Preferably such peptide sequences in their natural environment are located close to the protein surface and are accessible to the immune system so that one can assume a natural tolerance against this sequence. Examples are given in WO2007/090584.

Cleavable linkers should be flexible enough to allow cleavage by proteases. In a preferred embodiment the cleavage of the linker proceeds comparably fast as the activation of FVIII within the fusion protein, if the fusion protein is a modified FVIII.

The cleavable linker preferably comprises a sequence derived from
a) the therapeutic polypeptide to be administered itself if it contains proteolytic cleavage sites that are proteolytically cleaved during activation of the therapeutic polypeptide,
b) a substrate polypeptide cleaved by a protease which is activated or formed by the involvement of the therapeutic polypeptide.
c) a polypeptide involved in coagulation or fibrinolysis The linker region in a more preferred embodiment comprises a sequence of FVIII and/or VWF, which should result in a decreased risk of neoantigenic properties of the expressed fusion protein. Also in case the therapeutic protein is FVIII which needs to be proteolytically activated, the kinetics of the peptide linker cleavage will more closely reflect the coagulation-related activation kinetics of the zymogen.

In a preferred embodiment, the therapeutic polypeptide is FVIII zymogen and the HLEP is albumin. In this case the linker sequence is either derived from the sequences of the activation regions of FVIII, from the cleavage region of any substrate of FIX like FX or FVII or from the cleavage region of any substrate polypeptide that is cleaved by a protease in whose activation FIXa is involved.

In a highly preferred embodiment the linker peptide is derived from FVIII itself and comprises of sequences encompassing the thrombin cleavage sites at amino acid positions 372, 740 and 1689 of SEQ ID NO. 15, respectively. In another preferred embodiment the linker peptide is derived from FX, FIX, FVII or FXI.

The linker peptides are preferably cleavable by the proteases of the coagulation system, for example FIIa, FIXa, FXa, FXIa, FXIIa and FVIIa.

Said linker sequences can also be used in the modified VWF of the invention.

Exemplary combinations of therapeutic polypeptide, cleavable linker and HLEP include the constructs listed in WO2007/090584 (for example in table 2 and FIG. 4) and WO2007/144173 (for example in table 3a and 3b), but are not limited to these.

Half-Life Enhancing Polypeptides (HLEPs)

A "half-life enhancing polypeptide" as used herein is selected from the group consisting of albumin, a member of the albumin-family, the constant region of immunoglobulin G and fragments thereof region and polypeptides capable of binding under physiological conditions to albumin, to members of the albumin family as well as to portions of an immunoglobulin constant region. It may be a full-length half-life-enhancing protein described herein (e.g. albumin, a member of the albumin-family or the constant region of immunoglobulin G) or one or more fragments thereof that are capable of stabilizing or prolonging the therapeutic activity or the biological activity of the coagulation factor. Such fragments may be of 10 or more amino acids in length or may include at least about 15, at least about 20, at least about 25, at least about 30, at least about 50, at least about 100, or more contiguous amino acids from the HLEP sequence or may include part or all of specific domains of the respective HLEP, as long as the HLEP fragment provides a functional half-life extension of at least 25% compared to a wild-type FVIII or wild-type VWF.

The HLEP portion of the proposed coagulation factor insertion constructs of the invention may be a variant of a normal HLEP. The term "variants" includes insertions, deletions and substitutions, either conservative or non-conservative, where such changes do not substantially alter the active site, or active domain which confers the biological activities of the modified FVIII or modified VWF.

In particular, the proposed FVIII HLEP or VWF HLEP fusion constructs of the invention may include naturally occurring polymorphic variants of HLEPs and fragments of HLEPs. The HLEP may be derived from any vertebrate, especially any mammal, for example human, monkey, cow, sheep, or pig. Non-mammalian HLEPs include, but are not limited to, hen and salmon.

Albumin as HLEP

The terms, "human serum albumin" (HSA) and "human albumin" (HA) and "albumin" (ALB) are used interchangeably in this application. The terms "albumin" and "serum albumin" are broader, and encompass human serum albumin (and fragments and variants thereof) as well as albumin from other species (and fragments and variants thereof).

As used herein, "albumin" refers collectively to albumin polypeptide or amino acid sequence, or an albumin fragment or variant, having one or more functional activities (e.g., biological activities) of albumin. In particular, "albumin" refers to human albumin or fragments thereof, especially the mature form of human albumin as shown in SEQ ID NO:16 herein or albumin from other vertebrates or fragments thereof, or analogs or variants of these molecules or fragments thereof.

In particular, the proposed FVIII fusion and/or VWF fusion constructs of the invention may include naturally occurring polymorphic variants of human albumin and fragments of human albumin. Generally speaking, an albumin fragment or variant will be at least 10, preferably at least 40, most preferably more than 70 amino acids long. The albumin variant may preferentially consist of or alternatively comprise at least one whole domain of albumin or fragments of said domains, for example domains 1 (amino acids 1-194 of SEQ ID NO:16), 2 (amino acids 195-387 of SEQ ID NO: 16), 3 (amino acids 388-585 of SEQ ID NO: 16), 1+2 (1-387 of SEQ ID NO: 16), 2+3 (195-585 of SEQ ID NO: 16) or 1+3 (amino acids 1-194 of SEQ ID NO: 16+amino acids 388-585 of SEQ ID NO: 16). Each domain is itself made up of two homologous subdomains namely 1-105, 120-194, 195-291, 316-387, 388-491 and 512-585, with flexible inter-subdomain linker regions comprising residues Lys106 to Glu119, Glu292 to Val315 and Glu492 to Ala511.

The albumin portion of the proposed FVIII fusion and/or VWF fusion constructs of the invention may comprise at least one subdomain or domain of HA or conservative modifications thereof.

Afamin, Alpha-Fetoprotein and Vitamin D Binding Protein as HLEPs

Besides albumin, alpha-fetoprotein, another member of the albumin family, has been claimed to enhance the half-life of an attached therapeutic polypeptide in vivo (WO 2005/024044). The albumin family of proteins, evolutionarily related serum transport proteins, consists of albumin, alpha-fetoprotein (AFP; Beattie & Dugaiczyk 1982. Gene 20:415-422), afamin (AFM; Lichenstein et al. 1994. J. Biol. Chem. 269:18149-18154) and vitamin D binding protein (DBP; Cooke & David 1985. J_ Clin. Invest. 76:2420-2424). Their genes represent a multigene cluster with structural and functional similarities mapping to the same chromosomal region in humans, mice and rat. The structural similarity of the albumin family members suggest their usability as HLEPs. It is therefore another object of the invention to use such albumin family members, fragments and variants thereof as HLEPs. The term "variants" includes insertions, deletions and substitutions, either conservative or non-conservative as long as the desired function is still present. Albumin family members may comprise the full length of the respective protein AFP, AFM and DBP, or may include one or more fragments thereof that are capable of stabilizing or prolonging the therapeutic activity. Such fragments may be of 10 or more amino acids in length or may include about 15, 20, 25, 30, 50, or more contiguous amino acids of the respective protein sequence or may include part or all of specific domains of the respective protein, as long as the HLEP fragments provide a half-life extension of at least 25%. Albumin family members of the insertion proteins of the invention may include naturally occurring polymorphic variants of AFP, AFM and DBP.
Immunoglobulins as HLEPs Immunoglobulin G (IgG) constant regions (Fc) are known in the art to increase the half-life of therapeutic proteins (Dumont JA et al. 2006. BioDrugs 20:151-160). The IgG constant region of the heavy chain consists of 3 domains (CH1-CH3) and a hinge region. The immunoglobulin sequence may be derived from any mammal, or from subclasses IgG1, IgG2, IgG3 or IgG4, respectively. IgG and IgG fragments without an antigen-binding domain may also be used as HLEPs. The therapeutic polypeptide portion is connected to the IgG or the IgG fragments preferably via the hinge region of the antibody or a peptidic linker, which may even be cleavable. Several patents and patent applications describe the fusion of therapeutic proteins to immunoglobulin constant regions to enhance the therapeutic protein's in vivo half-lifes. US 2004/0087778 and WO 2005/001025 describe fusion proteins of Fc domains or at least portions of immunoglobulin constant regions with biologically active peptides that increase the half-life of the peptide, which otherwise would be quickly eliminated in vivo. Fc-IFN-β fusion proteins were described that achieved enhanced biological activity, prolonged circulating half-life and greater solubility (WO 2006/000448). Fc-EPO proteins with a prolonged serum half-life and increased in vivo potency were disclosed (WO 2005/063808) as well as Fc fusions with G-CSF (WO 2003/076567), glucagon-like peptide-1 (WO 2005/000892), clotting factors (WO 2004/101740) and interleukin-10 (US 6,403,077), all with half-life enhancing properties.
Polynucleotides The invention further relates to a polynucleotide encoding a modified coagulation factor, preferably a modified FVIII and/or modified VWF variant as described in this application. The term "polynucleotide(s)" generally refers to any polyribonucleotide or polydeoxyribonucleotide that may be unmodified RNA or DNA or modified RNA or DNA. The polynucleotide may be single- or double-stranded DNA, single or double-stranded RNA. As used herein, the term "polynucleotide(s)" also includes DNAs or RNAs that comprise one or more modified bases and/or unusual bases, such as inosine. It will be appreciated that a variety of modifications may be made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells.

The skilled person will understand that, due to the degeneracy of the genetic code, a given polypeptide can be encoded by different polynucleotides. These "variants" are encompassed by this invention.

Preferably, the polynucleotide of the invention is an isolated polynucleotide. The term "isolated" polynucleotide refers to a polynucleotide that is substantially free from other nucleic acid sequences, such as and not limited to other chromosomal and extrachromosomal DNA and RNA. Isolated polynucleotides may be purified from a host cell. Conventional nucleic acid purification methods known to skilled artisans may be used to obtain isolated polynucleotides. The term also includes recombinant polynucleotides and chemically synthesized polynucleotides.

The invention further relates to a group of polynucleotides which together encode the modified FVIII and/or the modified VWF of the invention. A first polynucleotide in the group may encode the N-terminal part of the modified FVIII and/or the modified VWF, and a second polynucleotide may encode the C-terminal part of the modified FVIII and/or the modified VWF.

Yet another aspect of the invention is a plasmid or vector comprising a polynucleotide according to the invention. Preferably, the plasmid or vector is an expression vector. In a particular embodiment, the vector is a transfer vector for use in human gene therapy.

The invention also relates to a group of plasmids or vectors that comprise the above group of polynucleotides. A first plasmid or vector may contain said first polynucleotide, and a second plasmid or vector may contain said second polynucleotide. By way of example, and with reference to coagulation factor VIII, the coding sequences of the signal peptide, the A1 and A2 domains, the B domain sequence remainder and the HLEP may be cloned into the first expression vector and the coding sequences of A3, C1 and C2 with an appropriate signal peptide sequence may be cloned into the second expression vector. Both expression vectors are cotransfected into a suitable host cell, which will lead to the expression of the light and heavy chains of the FVIII molecule of the invention and the formation of a functional protein.

Alternatively, the coding sequence of the FVIII signal peptide, the A1 and A2 domains are cloned into the first expression vector and the coding sequences of the HLEP, FVIII A3, C1 and C2 with an appropriate signal peptide sequence are cloned into the second expression vector. Both expression vectors are cotransfected into a suitable host cell, which will lead to the expression of the light and heavy chains of the FVIII molecule of the invention and the formation of a functional protein.

Alternatively, both coding sequences are cloned into one expression vector either using two separate promoter sequences or one promoter and an internal ribosome entry site (IRES) element to direct the expression of both FVIII chains.

Still another aspect of the invention is a host cell comprising a polynucleotide, a plasmid or vector of the invention, or a group of polynucleotides or a group of plasmids or vectors as described herein.

The host cells of the invention may be employed in a method of producing a modified coagulation factor, preferably a modified FVIII molecule, which is part of this invention. The method comprises:
  (a) culturing host cells of the invention under conditions such that the desired insertion protein is expressed; and
  (b) optionally recovering the desired insertion protein from the host cells or from the culture medium.

It is preferred to purify the modified FVIII and/or the modified VWF of the present invention to ≥80% purity, more preferably ≥95% purity, and particularly preferred is a pharmaceutically pure state that is greater than 99.9% pure with respect to contaminating macromolecules, particularly other proteins and nucleic acids, and free of infectious and pyrogenic agents. Preferably, an isolated or purified modified FVIII and/or the modified VWF of the invention is substantially free of other, non-related polypeptides.

The various products of the invention are useful as medicaments. Accordingly, the invention relates to a pharmaceutical composition comprising a modified FVIII and/or the modified VWF as described herein, a polynucleotide of the invention, or a plasmid or vector of the invention.

The invention also concerns a method of treating an individual suffering from a blood coagulation disorder such as hemophilia A or B. The method comprises administering to said individual an efficient amount of the FVIII and/or the modified VWF or the modified VWF or the complex of modified FVIII with non-modified VWF, or the complex of the non-modified FVIII with modified VWF or the complex of modified FVIII with modified VWF as described herein. In another embodiment, the method comprises administering to the individual an efficient amount of a polynucleotide of the invention or of a plasmid or vector of the invention. Alternatively, the method may comprise administering to the individual an efficient amount of the host cells of the invention described herein.

Expression of the Proposed Mutants

The production of recombinant mutant proteins at high levels in suitable host cells requires the assembly of the above-mentioned modified cDNAs into efficient transcriptional units together with suitable regulatory elements in a recombinant expression vector that can be propagated in various expression systems according to methods known to those skilled in the art. Efficient transcriptional regulatory elements could be derived from viruses having animal cells as their natural hosts or from the chromosomal DNA of animal cells. Preferably, promoter-enhancer combinations derived from the Simian Virus 40, adenovirus, BK polyoma virus, human cytomegalovirus, or the long terminal repeat of Rous sarcoma virus, or promoter-enhancer combinations including strongly constitutively transcribed genes in animal cells like beta-actin or GRP78 can be used. In order to achieve stable high levels of mRNA transcribed from the cDNAs, the transcriptional unit should contain in its 3'-proximal part a DNA region encoding a transcriptional termination-polyadenylation sequence. Preferably, this sequence is derived from the Simian Virus 40 early transcriptional region, the rabbit beta-globin gene, or the human tissue plasminogen activator gene.

The cDNAs are then integrated into the genome of a suitable host cell line for expression of the modified FVIII and/or VWF proteins. Preferably this cell line should be an animal cell-line of vertebrate origin in order to ensure correct folding, disulfide bond formation, asparagine-linked glycosylation and other post-translational modifications as well as secretion into the cultivation medium. Examples on other post-translational modifications are tyrosine 0-sulfation and proteolytic processing of the nascent polypeptide chain. Examples of cell lines that can be use are monkey COS-cells, mouse L-cells, mouse C127-cells, hamster BHK-21 cells, human embryonic kidney 293 cells, and hamster CHO-cells.

The recombinant expression vector encoding the corresponding cDNAs can be introduced into an animal cell line in several different ways. For instance, recombinant expression vectors can be created from vectors based on different animal viruses. Examples of these are vectors based on baculovirus, vaccinia virus, adenovirus, and preferably bovine papilloma virus.

The transcription units encoding the corresponding DNA's can also be introduced into animal cells together with another recombinant gene which may function as a dominant selectable marker in these cells in order to facilitate the isolation of specific cell clones which have integrated the recombinant DNA into their genome. Examples of this type of dominant selectable marker genes are Tn5 amino glycoside phosphotransferase, conferring resistance to geneticin (G418), hygromycin phosphotransferase, conferring resistance to hygromycin, and puromycin acetyl transferase, conferring resistance to puromycin. The recombinant expression vector encoding such a selectable marker can reside either on the same vector as the one encoding the cDNA of the desired protein, or it can be encoded on a separate vector which is simultaneously introduced and integrated to the genome of the host cell, frequently resulting in a tight physical linkage between the different transcription units.

Other types of selectable marker genes which can be used together with the cDNA of the desired protein are based on various transcription units encoding dihydrofolate reductase (dhfr). After introduction of this type of gene into cells lacking endogenous dhfr-activity, preferentially CHO-cells (DUKX-B11, DG-44), it will enable these to grow in media lacking nucleosides. An example of such a medium is Ham's F12 without hypoxanthine, thymidin, and glycine. These dhfr-genes can be introduced together with the FVIII cDNA transcriptional units into CHO-cells of the above type, either linked on the same vector or on different vectors, thus creating dhfr-positive cell lines producing recombinant protein.

If the above cell lines are grown in the presence of the cytotoxic dhfr-inhibitor methotrexate, new cell lines resistant to methotrexate will emerge. These cell lines may produce recombinant protein at an increased rate due to the amplified number of linked dhfr and the desired protein's transcriptional units. When propagating these cell lines in increasing concentrations of methotrexate (1-10000 nM), new cell lines can be obtained which produce the desired protein at very high rate.

The above cell lines producing the desired protein can be grown on a large scale, either in suspension culture or on various solid supports. Examples of these supports are micro carriers based on dextran or collagen matrices, or solid supports in the form of hollow fibres or various ceramic materials. When grown in cell suspension culture or on micro carriers the culture of the above cell lines can be performed either as a bath culture or as a perfusion culture with continuous production of conditioned medium over extended periods of time. Thus, according to the present invention, the above cell lines are well suited for the development of an industrial process for the production of the desired recombinant mutant proteins Purification and Formulation The recombinant modified FVIII and/or the recombinant modified VWF protein, which accumulates in the medium of secreting cells of the above types, can be concentrated and purified by a variety of biochemical and chromatographic methods, including methods utilizing differences in size, charge, hydrophobicity, solubility, specific affinity, etc. between the desired protein and other substances in the cell cultivation medium.

An example of such purification is the adsorption of the recombinant mutant protein to a monoclonal antibody, directed to e.g. a HLEP, preferably human albumin, or directed to the respective coagulation factor, which is immobilised on a solid support. After adsorption of the modified FVIII and/or modified VWF to the support, washing and desorption, the protein can be further purified by a variety of chromatographic techniques based on the above properties. The order of the purification steps is chosen e.g. according to capacity and selectivity of the steps, stability of the support or other aspects. Preferred purification steps e.g. are but are not limited to ion exchange chromatography steps, immune affinity chromatography steps, affinity chromatography steps, hydrophobic interaction chromatography steps, dye chromatography steps, hydroxyapatite chromatography steps, multimodal chromatography steps, and size exclusion chromatography steps.

In order to minimize the theoretical risk of virus contaminations, additional steps may be included in the process that allow effective inactivation or elimination of viruses. Such steps e.g. are heat treatment in the liquid or solid state, treatment with solvents and/or detergents, radiation in the visible or UV spectrum, gamma-radiation or nanofiltration.

The modified polynucleotides (e.g. DNA) of this invention may also be integrated into a transfer vector for use in the human gene therapy.

The various embodiments described herein may be combined with each other. The present invention will be further described in more detail in the following examples thereof. This description of specific embodiments of the invention will be made in conjunction with the appended figures.

The modified FVIII and/or modified VWF as described in this invention can be formulated into pharmaceutical preparations for therapeutic use. The purified protein may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", $3^{rd}$ edition, Kibbe et al., Pharmaceutical Press (2000)). In particular, the pharmaceutical composition comprising the polypeptide variant of the invention may be formulated in lyophilized or stable liquid form. The polypeptide variant may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of administration. Various delivery systems are known and can be used to administer the composition by any convenient route. Preferentially, the compositions of the invention are administered systemically. For systemic use, insertion proteins of the invention are formulated for parenteral (e.g. intravenous, subcutaneous, intramuscular, intraperitoneal, intracerebral, intrapulmonar, intranasal or transdermal) or enteral (e.g., oral, vaginal or rectal) delivery according to conventional methods. The most preferential routes of administration are intravenous and subcutaneous administration. The formulations can be administered continuously by infusion or by bolus injection. Some formulations encompass slow release systems.

The insertion proteins of the present invention are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, mode of administration and has to be determined in preclinical and clinical trials for each respective indication.

The pharmaceutical composition of the invention may be administered alone or in conjunction with other therapeutic agents. These agents may be incorporated as part of the same pharmaceutical. One example of such an agent is the combination of modified FVIII with non-modified VWF or the combination of non-modified FVIII with modified VWF or the combination of modified FVIII with modified VWF.

FIGURES

FIG. 1: Antigen and activity levels of wild-type FVIII and FVIII-C-terminal albumin fusion polypeptides FIG. 2: Comparison of human FVIII:Ag pharmacokinetics in VWF ko mice following i.v. injection of 100 U (FVIII:Ag)/kg FVIII wildtype and FVIII-FP 1656 VWF (mean; n=4/timepoint)

FIG. 3: VWF:RCo/VWF:Ag ratios of cell culture supernatants containing wt rVWF (1570/1212), rVWF-FP (1572/1212) containing C-terminally linked albumin, or a mixed expression cell culture containing a mixture of wt rVWF (1570/1212) and rVWF-FP (1572/1212) transfected in a ratio of 5:1. Values of about 0,8 were obtained in every case that are close to 1 which is the theoretical ratio of NHP according to the unit definitions.

FIG. 4: SDS-Agarose gel electrophoresis of wild-type rVWF (1570/1212) expressed in HEK cells (B) and rVWF-FP (1572/1212) expressed also in HEK cells (A). Bands were detected using either antibodies to VWF or to albumin (HSA).

FIG. 5: Comparison of human rWVF wildtype and rVWF-FP pharmacokinetics following i.v. injection of 100 IU VWF:Ag in rats (mean, n=2-3/timepoint)

EXAMPLES

Example 1

Generation of Expression Vectors for FVIII Molecules with C-Terminal Albumin Fusion An expression plasmid based on pIRESpuro3 (BD Biosciences) containing the full length FVIII cDNA sequence in its multiple cloning site (pF8-FL) was first used to create a B domain deleted FVIII. For that oligonucleotides F8-1 and F8-2 (SEQ ID NO 1 and 2) were used in a site-directed mutagenesis experiment according to standard protocols (QuickChange XL Site Directed Mutagenesis Kit, Stratagene, La Jolla, Calif., USA) using pF8-FL as a template to delete the B domain. In a second step a sequence encoding the amino acid sequence RRGR was introduced to connect R740 of the A2 domain with R1648 of the a3 domain. This was performed in another round of site-directed mutagenesis using primers F8-3 and F8-4 (SEQ ID NO 3 and 4). The resulting plasmid was called pF8-457. A FVIII albumin fusion construct was generated stepwise. First, a PinAl cleavage site was introduced at the FVIII 3'terminus. For that a PCR fragment was generated using pF8-457 as template, using PCR primers We2827 and We2828 (SEQ ID NO 5 and 6), which was subsquently gel-purified, cut by restriction endonucleases BspE1 and Notl and ligated into pF8-457 previously digested with BspE1 and Notl. The resulting plasmid (pF8-1433) was then cut with enzymes PinAl and Notl and a fragment obtained by PCR on a human albumin cDNA containing plasmid using primers We 2829 and We 2830 (SEQ ID NO 7 and 8) and subsequently digested with enzymes PinAl and Notl was inserted. The resulting expression plasmid (pF8-1434) contained the coding sequences for a B domain deleted FVIII followed by a PinAl site to insert linkers (encoding the amino acid sequence ThrGly) and the coding sequence for human albumin. The amino acid sequence encoded by pF8-1434 is depicted as SEQ ID NO 9.

Linker sequences separating the FVIII and albumin moieties could then easily be inserted into the newly created PinAI site described above. The insertion of two linker sequences is described in the following. In addition, based on pF8-1434, the TG linker might be deleted in completion and even deletions into the C-terminus of FVIII or the N-terminus of albumin can be performed using site directed mutagenesis. Insertion of a cleavable linker, derived from the FVIII thrombin cleavage site: First a PCR fragment containing the sequence encoding the thrombin cleavage site at position 372 was generated by PCR using primers We2979 and We2980 (SEQ ID NO 10 and 11) and pF8-457 as template. This fragment was purified, digested with PinAI and ligated into PinAI digested pF8-1434. Sequencing verified insertion of correct orientation of the fragment, the resulting plasmid was called pF8-1563.

Insertion of a flexible glycine/serine linker: A PCR fragment containing the coding sequence for a 31 amino acid glycine/serine linker was amplified by PCR from pFVII-937 described in WO2007/090584 using primers We2991 and We2992 (SEQ ID NO 12 and 13). This fragment was then purified, digested by restriction endonuclease PinAI and ligated into PinAI digested pF8-1434. Sequencing verified insertion of correct orientation of the fragment, the resulting plasmid was called pF8-1568.

Using the protocols and plasmids described above and by applying molecular biology techniques known to those skilled in the art (and as described e.g. in Current Protocols in Molecular Biology, Ausubel FM et al. (eds.) John Wiley & Sons, Inc.; http://www.currentprotocols.com/WileyCDA/) other constructs can be made by the artisan to replace albumin by another HLEP or insert any other linker into the described PinAI site. Transfer of the FVIII/albumin cDNA into suitable vectors like pIRESneo3 (Invitrogen) and pEE12.4 (Lonza) permitted expression and selection of clones expressing the respective FVIII albumin fusion protein in CHO cells.

Example 2

Transfection and Expression of FVIII and VWF Proteins

Expression plasmids were grown up in *E.coli* TOP10 (Invitrogen, Carlsbad, Calif., USA) and purified using standard protocols (Qiagen, Hilden, Germany). HEK-293 (Invitrogen) cells were transfected using the Lipofectamine 2000 reagent (Invitrogen) and grown up in serum-free medium (Invitrogen 293 Express) in the presence of 4 µg/ml Puromycin and optionally 0.5 IU/ml VWF. CHO cells (CHO-S, Invitrogen; CHOK1SV, Lonza) were transfected using the Lipofectamine 2000 reagent (Invitrogen) and grown up in serum-free medium (Invitrogen CD CHO, 6 mM glutamine for CHO-S and CD-CHO for CHOK1SV) in the presence of 500-1000 µg/ml Geneticin (CHO-S only). For FVIII expression optionally 0.5 IU/ml VWF were added. For vWF expression an expression plasmid encoding PACE/furin (pFu-797) as described in WO2007/144173 was cotransfected. In another experiment two plasmids encoding VWF wild-type and VWF fused at the C-terminus to albumin were cotransfected with pFu-797 resulting in VWF multimeres with wild-type VWF monomers and albumin-fused VWF monomers (see FIG. 3). Transfected cell populations were spread through T-flasks into roller bottles or small scale fermenters from which supernatants were harvested for purification.

Table 2 lists HEK-293 expression data of the constructs described in example 1.

TABLE 2

| Construct | Activity [U/mL] |
|---|---|
| pF8-457 | 1.54 |
| pF8-457 + 0.5 U/ml VWF | 1.66 |
| pF8-1434 | 1.59 |
| pF8-1434 + 0.5 U/ml VWF | 1.82 |
| pF8-1563 + 0.5 U/ml VWF | 2.04 |
| pF8-1568 + 0.5 U/ml VWF | 1.21 |

Example 3

Increased Expression Rate of FVIII Albumin Fusion Protein

FIG. 1 summarizes the results of an expression study of a FVIII albumin fusion protein in serum-free cell culture. HEK-293 cells were transfected in triplicate with pF8-1434 (FVIII C-terminal albumin fusion) and pF8-457 (FVIII wild-type), respectively, seeded into T80 flasks with equal cell numbers and grown in the absence of stabilizing VWF. Culture supernatant was then harvested after 96, 120 and 144 hours and tested for FVIII activity.

The results demonstrated an expression enhancing effect of the albumin moiety when present as an integral part of the FVIII molecule in cell culture. Consequently, the productivity was clearly improved in the case of the fusion protein compared to wild-type FVIII (FIG. 1).

Example 4

Purification of FVIII Proteins

To the expression supernatant containing the FVIII molecule a sufficient amount of an immune affinity resin was added to bind the FVIII activity almost completely. The immune affinity resin had been prepared by binding an appropriate anti-FVIII MAb covalently to Sephacryl S1000 resin used as a support. After washing of the resin it was filled into a chromatography column and washed again. Elution was done using a buffer containing 250 mM $CaCl_2$ and 50% ethylene glycol.

The immune affinity chromatography (IAC) fractions containing FVIII:C activity were pooled, dialyzed against formulation buffer (excipients: sodium chloride, sucrose, histidine, calcium chloride, and Tween 80), and concentrated. Samples were either stored frozen or freeze-dried using an appropriate freeze-drying cycle.

Alternatively, the FVIII containing cell culture supernatant is concentrated/purified by a first ion exchange chromatography followed by further purification using immune affinity chromatography (IAC). In this case the eluate of the ion exchange chromatography is loaded onto an IAC column using the above mentioned resin.

Example 5

Analysis of FVIII Activity and Antigen

For activity determination of FVIII:C in vitro either a clotting assay (e.g. Pathromtin SL reagent and FVIII deficient plasma delivered by Dade Behring, Germany) or a chromogenic assay (e.g. Coamatic FVIII:C assay delivered by Haemochrom) were used. The assays were performed according to the manufacturers instructions.

FVIII antigen (FVIII:Ag) was determined by an ELISA whose performance is known to those skilled in the art. Briefly, microplates were incubated with 100 μL per well of the capture antibody (sheep anti-human FVIII IgG, Cedarlane CL20035K-C, diluted 1:200 in Buffer A [Sigma C3041]) for 2 hours at ambient temperature. After washing plates three times with buffer B (Sigma P3563), serial dilutions of the test sample in sample diluent buffer (Cedarlane) as well as serial dilutions of a FVIII preparation (CSL Behring; 200-2 mU/mL) in sample diluent buffer (volumes per well: 100 μL) were incubated for two hours at ambient temperature. After three wash steps with buffer B, 100 μL of a 1:2 dilution in buffer B of the detection antibody (sheep anti-human FVIII IgG, Cedarlane CL20035K-D, peroxidase labelled) were added to each well and incubated for another hour at ambient temperature. After three wash steps with buffer B, 100 μL of substrate solution (1:10 (v/v) TMB OUVF : TMB Buffer OUVG, Dade Behring) were added per well and incubated for 30 minutes at ambient temperature in the dark. Addition of 100 μL stop solution (Dade Behring, OSFA) prepared the samples for reading in a suitable microplate reader at 450 nm wavelength. Concentrations of test samples were then calculated using the standard curve with the FVIII preparation as reference.

Example 6

Assessment of Pharmacokinetics of FVIII-FP in VWF ko Mice Following a Single i.v. Injection In order to compare the pharmacokinetics of FVIII wild-type (DNA 457) and a C-terminal FVIII-FP (DNA 1656), both FVIII variants were administered intravenously to mice. A VWF ko mouse strain (Denis C. et al, Proc. Natl. Acad. Sci. USA, 1998, Vol 95, 9524-9529) was chosen because, amongst other functions, VWF serves as a carrier and stabilizing protein for FVIII, thereby protecting FVIII from premature degradation, e.g. by proteases, and from premature elimination from circulation. For unmodified FVIII an undisturbed interaction with VWF is essential as exemplified by hemophilia A cases, caused by mutation in the C terminal region resulting in decreasing binding to VWF. In the case of modified FVIII such binding may, however, be even unwanted, in order to examine or achieve improved pharmacokinetics. Accordingly both products were injected i.v. at a dose of 100 U (FVIII:Ag)/kg as bolus to two groups of mice (Tab. 3). Blood was sampled retroorbitally at appropriate intervals starting at 5 minutes after application of the test substances and up to 24 hours. One blood sample/mouse was taken, processed to plasma and stored frozen at −20° C. until analysis. Human FVIII:Ag concentration was quantified using an ELISA assay specific for human FVIII or by a mixed ELISA specific for human albumin and FVIII, respectively. The mean plasma concentration of the, for each timepoint pooled, samples was used for calculation of pharmacokinetic parameters. Half-live was calculated using the time points of the beta phase of elimination according to the formula $t_{1/2}=\ln2/k$, whereas k is the slope of the regression line. The result is depicted in FIG. 2. Surprisingly, FVIII-FP 1656 ($t_{1/2}$=3.06 h, between 5 and 960 min) had an about 3-4 times longer terminal half-life as compared to FVIII wildtype ($t_{1/2}$=0.8 h, between 5 and 240 min). In addition, the recovery of FVIII-FP 1656 was increased by about 20% as compared to wildtype FVIII (Tab. 4).

TABLE 3

Treatment groups for comparison of pharmacokinetics FVIII in VWF ko mice

| Treatment | Dose (FVIII:C)/volume/schedule/route | N |
|---|---|---|
| FVIII wildtype | 100 U (FVIII:Ag)/kg/ 0.2 mL/20 g b.w./t = 0 h/i.v.. | 24 |
| FVIII-FP 1656 | 100 U(FVIII:Ag)/kg/ 0.2 mL/20 g b.w./t = 0 h/i.v.. | 24 |

TABLE 4

Bioavailability (%) of FVIII wildtype and modified FVIII, FVIII-FP 1656, upon i.v. injection into VWF ko mice

| Treatment | Bioavailability (%) |
|---|---|
| FVIII wildtype | 100 |
| FVIII-FP 1656 | 120.4 |

Example 7

Generation of Expression Vectors for VWF Wild-Type and VWF Albumin Fusion Proteins An expression plasmid containing the full length VWF cDNA sequence in its multiple cloning site was generated first. For that the coding sequence of VWF was amplified by polymerase chain reaction (PCR) using primer set VWF+ and VWF−(SEQ ID NO. 17 and 18) under standard conditions known to those skilled in the art (and as described e.g. in Current Protocols in Molecular Biology, Ausubel F M et al. (eds.) John Wiley & Sons, Inc.; http://www.currentprotocols.com/WileyCDA/) from a plasmid containing VWF cDNA (as obtainable commercially, e.g. pMT2-VWF from ATCC, No. 67122). The resulting PCR fragment was digested by restriction endonuclease EcoRI and ligated into expression vector pIRESpuro3 (BD Biosciences, Franklin Lakes, N.J., USA) which had been linearized by EcoRI. The resulting expression plasmid containing the wild-type cDNA of VWF downstream of the CMV promoter was called pVWF-1570.

A PCR fragment containing the coding sequence for a 31 amino acid glycine/serine linker and the human albumin cDNA was amplified from pFVII-937 described in WO2007/090584 using primers We2994 and We1335 (SEQ ID NO. 19 and 20). This PCR fragment was then digested by restriction endonuclease NotI and ligated into NotI digested pVWF-1570. The resulting plasmid containing the coding sequences of VWF wt, the linker sequence and human albumin was called pVWF-1574.

In order to achieve expression of a fusion protein several bases had to be deleted between VWF and the linker sequence. This was peformed by site directed mutagenesis according to standard protocols (QuickChange XL Site Directed Mutagenesis Kit, Stratagene, La Jolla, Calif., USA) using oligonucleotides We2995 and We2996 (SEQ ID NO 21 and 22). The resulting expression plasmid called pVWF-1572 contained the coding sequences of VWF in frame with that of a 31 amino acid glycin/serine linker and human albumin. The amino acid sequence of the expressed rVWF-FP is outlined as SEQ ID No. 25. The amino acid sequence of the human VWF preproprotein is outlined as SEQ ID NO. 24.

Using the protocols and plasmids described above and by applying molecular biology techniques known to those skilled in the art (and as described e.g. in Current Protocols in Molecular Biology, ibid) other constructs can be made by the artisan for replacement of the albumin sequence by another HLEP sequence or the linker sequence by another linker sequence.

Example 8

Purification of VWF and VWF Albumin Fusion Proteins

Cell culture supernatants containing VWF wild-type (rVWF wt) or VWF albumin fusion protein (rVWF-FP) were sterile-filtered through a 0.2 μm filter and dialysed against equilibration buffer (EB; 10 mM Tris-HCl, 10 mM $CaCl_2$, pH 7.0). This material was then applied to a Heparin Fractogel column equilibrated with EB. The column was washed with EB and VWF proteins were eluated with 500 mM NaCl in EB. The elution peak was concentrated and dialysed against FB buffer (3 g/L sodium chloride, 20 g/L glycine, 5.5 g/L trisodium citrate dihydrate, pH 7.0). Finally the material was sterile filtrated and frozen in aliquots. If needed, further purification steps were applied comprising anion and/or cation exchange chromatography, HIC and SEC.

Example 9

Analysis of VWF Activity and Antigen

Samples were analysed by immunoturbidimetric determination of VWF:Ag (OPAB03, Siemens Healthcare Diagnostics, Marburg, Germany) and for collagen binding (Technozym VWF:CBA ELISA, Ref. 5450301 with calibrator set 5450310 and control set 5450312, Technoclone, Vienna, Austria) as described by the manufacturer.

VWF:RCo testing was done using the BC VWF reagent of Siemens Healthcare Diagnostics, Marburg, Germany according to the manufacturers description. The International Concentrate Standard was used as a primary standard preparation to calibrate an in-house standard preparation for day to day use.

The ratios of VWF:RCo and VWF:Ag assays are calculated in order to compare this parameter for different constructs tested. As is shown in FIG. 3 the VWF:RCo/VWF:Ag ratio was comparable for wt rVWF and the C-terminal rVWF-albumin fusion protein.

For pharmacokinetic analyses VWF antigen was determined by an ELISA whose performance is known to those skilled in the art. Briefly, microplates were incubated with 100 μL per well of the capture antibody (rabbit anti human VWF-IgG, Dako A0082 [Dako, Hamburg, Germany], diluted 1:2000 in buffer A [Sigma C3041, Sigma-Aldrich, Munich, Germany]) overnight at ambient temperature. After washing plates three times with buffer B (Sigma P3563), each well was incubated with 200 μL buffer C (Sigma P3688) for 1.5 hours at ambient temperature (blocking). After another three wash steps with buffer B, serial dilutions of the test sample in buffer B as well as serial dilutions of standard human plasma (ORKL21; 20-0.2 mU/mL; Siemens Healthcare Diagnostics, Marburg, Germany) in buffer B (volumes per well: 100 μL) were incubated for 1.5 hours at ambient temperature. After three wash steps with buffer B, 100 μL of a 1:16000 dilution in buffer B of the detection antibody (rabbit anti human VWF-IgG, Dako P0226, peroxidase labelled) were added to each well and incubated for 1 hour at ambient temperature. After three wash steps with buffer B, 100 μL of substrate solution (OUVF, Siemens Healthcare Diagnostics) were added per well and incubated for 30 minutes at ambient temperature in the dark. Addition of 100 μL undiluted stop dilution (OSFA, Siemens Healthcare Diagnostics) prepared the samples for reading in a suitable microplate reader at 450 nm wavelength. Concentrations of the test samples were then calculated using the standard curve with standard human plasma as reference.

Example 10

Multimer Analysis of VWF and VWF Albumin Fusion Proteins

VWF Multimer analysis was performed by SDS-agarose gel electrophoresis as recently described (Tatewaki et al.,. Thromb. Res. 52: 23-32 (1988), and Metzner et al., Haemophilia 4 (Suppl. 3): 25-32 (1998)) with minor modifications. Briefly, after equilibration in running buffer ready to use 1% agarose mini gels (BioRad) were used to standardize the method as far as possible. Comparable amounts of VWF antigen were subjected to electrophoresis on the SDS-agarose gels. After Western blotting the VWF protein bands were detected using anti-VWF (DAKO, prod. No. 0854) or anti-albumin antibodies followed by alkaline phosphatase labelled anti-IgG antibodies (SIGMA, prod. No. 1305) and colour reaction quantified by densitometry.

Using wild-type rVWF (1570/797) and rVWF-FP (1572/797) it could be demonstrated by Western blotting and detection using anti-albumin or anti VWF antibodies that rVWF-FP forms a regular multimer distribution detected both by anti-albumin and anti-VWF antibodies (FIG. 4). This confirms that although every subunit of the multimeric VWF contains albumin, a regular VWF multimer pattern is formed. The albumin moiety obviously does neither inhibit the N-terminal dimerization nor the C-terminal multimerization of the VWF molecules.

Example 11

Assessment of Pharmacokinetics of VWF and VWF Albumin Fusion Protein in Rats Following a Single i.v. Injection rVWF-FP and rVWF wt were administered intravenously to a total of 4 CD rats each. The dose was 100 U (VWF:Ag)/kg body weight, at an injection volume of 4 mL/kg. Blood samples were drawn retroorbitally at appropriate intervals starting at 5 minutes after application of the test substances, using an alternating sampling scheme, resulting in samples from 2 animals/timepoint (t=0, 5, 30, 90 min, 4 h, 1 d for subset Nr. 1 and 0, 15 min, 1, 2, 8 h and 2 d for subset Nr. 2). The scheme was designed to minimize potential effects of blood sampling on the plasma concentration to be quantified. Blood was processed to plasma and stored deep frozen until analysis. The VWF:Ag level in plasma was subsequently quantified by an ELISA as described in Example 9. The mean plasma concentration was used for calculation of pharmacokinetic parameters. Half-live was calculated using the time points of the beta phase of elimination according to the formula $t_{1/2}=\ln2/k$, whereas k is the slope of the regression line.

The result is depicted in FIG. 5 (n=2/timepoint; mean). The terminal half-lifes were calculated to be 32.4 min. for the rVWF-FP and 2.6 min. for rVWF wt. Recovery was also improved for the rVWF-FP with 42.1% compared to 16.1% for rVWF wt.

The invention claimed is:

1. A modified Factor VIII (FVIII) polypeptide or a complex comprising a modified FVIII polypeptide and a von Willebrand factor (VWF) polypeptide (monomer, dimer, or multimer), wherein the modified FVIII polypeptide comprises a FVIII polypeptide fused at a C-terminal part of its primary translation polypeptide to an N-terminal part of albumin or a fragment thereof, and wherein the fusion of albumin or a fragment thereof to the FVIII polypeptide does not prevent the modified FVIII polypeptide from binding to VWF and to activated platelets.

2. The modified polypeptide or complex according to claim 1, wherein the modified FVIII polypeptide has a prolonged functional half-life compared to the functional half-life of a non-modified FVIII polypeptide.

3. The modified polypeptide or complex according to claim 2, wherein the modified FVIII polypeptide has a functional half-life increased by at least 25% as compared to the functional half-life of the non-modified FVIII polypeptide, or the complex has a functional half-life increased by at least 25% as compared to the corresponding complex of a non-modified FVIII polypeptide and a non-modified VWF polypeptide.

4. The modified polypeptide or complex according to claim 1, wherein the modified FVIII polypeptide has a prolonged antigen half-life after administration to a subject as compared to the antigen half-life of a non-modified FVIII polypeptide, or the complex comprising modified FVIII polypeptide has a prolonged antigen half-life after administration to a subject as compared to the antigen half-life of a corresponding complex of a non-modified FVIII polypeptide and a non-modified VWF polypeptide.

5. The modified polypeptide or complex according to claim 4, wherein the modified FVIII polypeptide has an antigen half-life increased by at least 25% as compared to the antigen half-life of the non-modified FVIII polypeptide, or the complex comprising modified FVIII polypeptide has an antigen half-life increased by at least 25% as compared to the corresponding complex of a non-modified FVIII polypeptide and a non-modified VWF polypeptide.

6. The modified polypeptide or complex according to claim 1, wherein the modified FVIII polypeptide has an increased in vivo recovery after administration to a subject as compared to the in vivo recovery of a non-modified FVIII polypeptide, or the complex comprising modified FVIII polypeptide has an increased in vivo recovery after administration to a subject as compared to the in vivo recovery of a corresponding complex comprising a non-modified FVIII polypeptide and a non-modified VWF polypeptide.

7. The modified polypeptide or complex according to claim 6, wherein the modified FVIII polypeptide has an in vivo recovery increased by at least 10% as compared to the in vivo recovery of the non-modified FVIII polypeptide, or the complex comprising modified FVIII polypeptide has an in vivo recovery increased by at least 10% as compared to the corresponding complex of a non-modified FVIII polypeptide and a non-modified VWF polypeptide.

8. The modified polypeptide or complex according to claim 1, wherein the FVIII polypeptide is fused at the C-terminal amino acid of its primary translation product to an N-terminal part of albumin or a fragment thereof.

9. The modified polypeptide or complex according to claim 1, wherein the FVIII polypeptide is fused at a C-terminal part of its primary translation product to the N-terminal amino acid of albumin or a fragment thereof.

10. The modified polypeptide or complex according to claim 1, wherein the modified FVIII polypeptide has at least 10% of the biological activity of a corresponding non-modified FVIII polypeptide, or the complex comprising modified FVIII polypeptide has at least 10% of the biological activity of a corresponding complex of a non-modified FVIII polypeptide and a non-modified VWF polypeptide.

11. A method of producing a modified Factor VIII (FVIII) polypeptide, comprising:
  (a) culturing host cells comprising a polynucleotide or group of polynucleotides encoding the modified FVIII polypeptide or the complex comprising the modified FVIII polypeptide according to claim 1 under conditions such that the modified FVIII polypeptide is expressed; and
  (b) recovering the modified FVIII polypeptide or the complex comprising the modified FVIII polypeptide from the host cells or from the culture medium.

12. A pharmaceutical composition comprising the modified FVIII polypeptide or complex according to claim 1.

13. A method for treating a blood coagulation disorder comprising administering to a patient in need thereof an effective amount of the pharmaceutical composition of claim 12.

14. The method according to claim 13, wherein the blood coagulation disorder is hemophilia A.

15. The method according to claim 13, wherein the blood coagulation disorder is von Willebrand disease.

16. A method of preparing a modified Factor VIII (FVIII) polypeptide, comprising fusing an N-terminal part of albumin or a fragment thereof to a C-terminal part of the primary translation polypeptide of FVIII such that the fusion of albumin or a fragment thereof to the FVIII polypeptide does not prevent the modified FVIII polypeptide from binding to VWF and to activated platelets.

17. A method of preparing a complex comprising a modified FVIII polypeptide and a von Willebrand factor (VWF) polypeptide (monomer, dimer, or multimer), comprising mixing the VWF polypeptide with the modified FVIII polypeptide,
  wherein the modified FVIII polypeptide comprises a FVIII polypeptide fused at a C-terminal part of its primary translation polypeptide to an N-terminal part of albumin or a fragment thereof, and wherein the fusion of albumin or a fragment thereof to the FVIII polypeptide does not prevent the modified FVIII polypeptide from binding to VWF and to activated platelets.

18. A method of treating a bleeding disorder comprising administering to a patient in need thereof an effective amount of the modified FVIII polypeptide prepared by the method of claim 16 or the complex prepared by the method of claim 17.

19. The method of claim 18, wherein the bleeding disorder is hemophilia A.

20. The method of claim 18, wherein the bleeding disorder is von Willebrand disease.

21. The modified polypeptide or complex according to claim 1, wherein the modified FVIII polypeptide comprises a FVIII polypeptide fused to the N-terminal part of albumin or a fragment thereof,
  wherein the albumin or a fragment thereof is fused to an amino acid of FVIII located at a distance from the C-terminal amino acid of up to 1% of the total length of the FVIII primary translation polypeptide, based on the total number of amino acids in the FVIII primary translation polypeptide.

22. The modified polypeptide or complex according to claim 1, wherein the modified FVIII polypeptide comprises a FVIII polypeptide fused to the N-terminal amino acid of albumin or a fragment thereof,
  wherein the albumin or a fragment thereof is fused to an amino acid of FVIII located at a distance from the C-terminal amino acid of up to 1% of the total length of the FVIII primary translation polypeptide, based on the total number of amino acids in the FVIII primary translation polypeptide.

23. The modified polypeptide or complex according to claim 1, wherein the modified FVIII polypeptide comprises a FVIII polypeptide fused at the C-terminal amino acid of its primary translation polypeptide to the N-terminal amino acid of albumin or a fragment thereof.

24. The modified polypeptide or complex according to claim 1, wherein 1-5 amino acids at the natural C-terminus of the FVIII primary translation polypeptide have been deleted, and wherein the resulting C-terminal amino acid of the FVIII polypeptide is fused to the N-terminal amino acid of albumin or a fragment thereof.

25. The modified polypeptide or complex according to claim 1, wherein the natural C-terminal amino acid of the FVIII primary translation polypeptide has been deleted, and wherein the resulting C-terminal amino acid of the FVIII polypeptide is fused to the N-terminal amino acid of albumin or a fragment thereof.

26. The modified polypeptide or complex according to claim 1, wherein the VWF polypeptide is a modified VWF polypeptide comprising a VWF polypeptide fused at a C-terminal part of its primary translation polypeptide to an N-terminal part of albumin or a fragment thereof, and wherein the fusion of albumin or a fragment thereof to the VWF polypeptide does not prevent dimerization or multimerization of the modified VWF polypeptide.

27. The modified polypeptide or complex according to claim 26, wherein the modified VWF polypeptide comprises a VWF polypeptide fused to the N-terminal part of albumin or a fragment thereof,
  wherein albumin or a fragment thereof is fused to an amino acid of VWF located at a distance from the C-terminal amino acid of up to 1% of the total length of the VWF primary translation polypeptide, based on the total number of amino acids in the VWF primary translation polypeptide.

28. The modified polypeptide or complex according to claim 26, wherein the modified VWF polypeptide comprises a VWF polypeptide fused to the N-terminal amino acid of albumin or a fragment thereof, wherein albumin or a fragment thereof is fused to an amino acid of VWF located at a distance from the C-terminal amino acid of up to 1% of the total length of the VWF primary translation polypeptide, based on the total number of amino acids in the VWF primary translation polypeptide.

29. The modified polypeptide or complex according to claim 26, wherein the modified VWF polypeptide comprises a VWF polypeptide fused at the C-terminal amino acid of its primary translation polypeptide to the N-terminal amino acid of albumin or a fragment thereof.

30. The modified polypeptide or complex according to claim 26, wherein 1-5 amino acids at the natural C-terminus of the VWF primary translation polypeptide have been deleted, and wherein the resulting C-terminal amino acid of the VWF polypeptide is fused to the N-terminal amino acid of albumin or a fragment thereof.

31. The modified polypeptide or complex according to claim 26, wherein the natural C-terminal amino acid of the VWF primary translation polypeptide has been deleted, and wherein the resulting C-terminal amino acid of the VWF polypeptide is fused to the N-terminal amino acid of albumin or a fragment thereof.

* * * * *

SEQUENCE LISTING

<160> NUMBER OF SEQ ID NOS: 25

<210> SEQ ID NO 1
<211> LENGTH: 36
<212> TYPE: DNA
<213> ORGANISM: Artificial
<220> FEATURE:
<223> OTHER INFORMATION: Primer

<400> SEQUENCE: 1
caatgccatt gaaccaagac gagaaataac tcgtac                                    36

<210> SEQ ID NO 2
<211> LENGTH: 36
<212> TYPE: DNA
<213> ORGANISM: Artificial
<220> FEATURE:
<223> OTHER INFORMATION: Primer

<400> SEQUENCE: 2
gtacgagtta tttctcgtct tggttcaatg gcattg                                    36

<210> SEQ ID NO 3
<211> LENGTH: 48
<212> TYPE: DNA
<213> ORGANISM: Artificial
<220> FEATURE:
<223> OTHER INFORMATION: Primer

<400> SEQUENCE: 3
caatgccatt gaaccaagac gtcgtggtcg acgagaaata actcgtac                       48

<210> SEQ ID NO 4
<211> LENGTH: 48
<212> TYPE: DNA
<213> ORGANISM: Artificial
<220> FEATURE:
<223> OTHER INFORMATION: Primer

<400> SEQUENCE: 4
gtacgagtta tttctcgtcg accacgacgt cttggttcaa tggcattg                       48

<210> SEQ ID NO 5
<211> LENGTH: 23
<212> TYPE: DNA
<213> ORGANISM: Artificial
<220> FEATURE:
<223> OTHER INFORMATION: Primer

<400> SEQUENCE: 5
cattattccg gatcaatcaa tgc                                                  23

<210> SEQ ID NO 6
<211> LENGTH: 38
<212> TYPE: DNA
<213> ORGANISM: Artificial
<220> FEATURE:
<223> OTHER INFORMATION: Primer

<400> SEQUENCE: 6
acgcggccgc ggtaccggtg tagaggtcct gtgcctcg                                  38

<210> SEQ ID NO 7
<211> LENGTH: 31
<212> TYPE: DNA
<213> ORGANISM: Artificial

```
<220> FEATURE:
<223> OTHER INFORMATION: Primer

<400> SEQUENCE: 7
gtgaccggtg atgcacacaa gagtgaggtt g                              31

<210> SEQ ID NO 8
<211> LENGTH: 32
<212> TYPE: DNA
<213> ORGANISM: Artificial
<220> FEATURE:
<223> OTHER INFORMATION: Primer

<400> SEQUENCE: 8
cacgcggccg cctataagcc taaggcagct tg                             32

<210> SEQ ID NO 9
<211> LENGTH: 2016
<212> TYPE: PRT
<213> ORGANISM: Homo sapiens

<400> SEQUENCE: 9
```

| Ala | Thr | Arg | Arg | Tyr | Tyr | Leu | Gly | Ala | Val | Glu | Leu | Ser | Trp | Asp | Tyr |
|---|---|---|---|---|---|---|---|---|---|---|---|---|---|---|---|
| 1 | | | | 5 | | | | | 10 | | | | | 15 | |

| Met | Gln | Ser | Asp | Leu | Gly | Glu | Leu | Pro | Val | Asp | Ala | Arg | Phe | Pro | Pro |
|---|---|---|---|---|---|---|---|---|---|---|---|---|---|---|---|
| | | | 20 | | | | | 25 | | | | | 30 | | |

| Arg | Val | Pro | Lys | Ser | Phe | Pro | Phe | Asn | Thr | Ser | Val | Val | Tyr | Lys | Lys |
|---|---|---|---|---|---|---|---|---|---|---|---|---|---|---|---|
| | | 35 | | | | | 40 | | | | | 45 | | | |

| Thr | Leu | Phe | Val | Glu | Phe | Thr | Asp | His | Leu | Phe | Asn | Ile | Ala | Lys | Pro |
|---|---|---|---|---|---|---|---|---|---|---|---|---|---|---|---|
| 50 | | | | | 55 | | | | | 60 | | | | | |

| Arg | Pro | Pro | Trp | Met | Gly | Leu | Leu | Gly | Pro | Thr | Ile | Gln | Ala | Glu | Val |
|---|---|---|---|---|---|---|---|---|---|---|---|---|---|---|---|
| 65 | | | | 70 | | | | | 75 | | | | | 80 | |

| Tyr | Asp | Thr | Val | Val | Ile | Thr | Leu | Lys | Asn | Met | Ala | Ser | His | Pro | Val |
|---|---|---|---|---|---|---|---|---|---|---|---|---|---|---|---|
| | | | | 85 | | | | | 90 | | | | | 95 | |

| Ser | Leu | His | Ala | Val | Gly | Val | Ser | Tyr | Trp | Lys | Ala | Ser | Glu | Gly | Ala |
|---|---|---|---|---|---|---|---|---|---|---|---|---|---|---|---|
| | | | 100 | | | | | 105 | | | | | 110 | | |

| Glu | Tyr | Asp | Asp | Gln | Thr | Ser | Gln | Arg | Glu | Lys | Glu | Asp | Asp | Lys | Val |
|---|---|---|---|---|---|---|---|---|---|---|---|---|---|---|---|
| | | | 115 | | | | | 120 | | | | | 125 | | |

| Phe | Pro | Gly | Gly | Ser | His | Thr | Tyr | Val | Trp | Gln | Val | Leu | Lys | Glu | Asn |
|---|---|---|---|---|---|---|---|---|---|---|---|---|---|---|---|
| | 130 | | | | | 135 | | | | | 140 | | | | |

| Gly | Pro | Met | Ala | Ser | Asp | Pro | Leu | Cys | Leu | Thr | Tyr | Ser | Tyr | Leu | Ser |
|---|---|---|---|---|---|---|---|---|---|---|---|---|---|---|---|
| 145 | | | | | 150 | | | | | 155 | | | | | 160 |

| His | Val | Asp | Leu | Val | Lys | Asp | Leu | Asn | Ser | Gly | Leu | Ile | Gly | Ala | Leu |
|---|---|---|---|---|---|---|---|---|---|---|---|---|---|---|---|
| | | | | 165 | | | | | 170 | | | | | 175 | |

| Leu | Val | Cys | Arg | Glu | Gly | Ser | Leu | Ala | Lys | Glu | Lys | Thr | Gln | Thr | Leu |
|---|---|---|---|---|---|---|---|---|---|---|---|---|---|---|---|
| | | | 180 | | | | | 185 | | | | | 190 | | |

| His | Lys | Phe | Ile | Leu | Leu | Phe | Ala | Val | Phe | Asp | Glu | Gly | Lys | Ser | Trp |
|---|---|---|---|---|---|---|---|---|---|---|---|---|---|---|---|
| | | 195 | | | | | 200 | | | | | 205 | | | |

| His | Ser | Glu | Thr | Lys | Asn | Ser | Leu | Met | Gln | Asp | Arg | Asp | Ala | Ala | Ser |
|---|---|---|---|---|---|---|---|---|---|---|---|---|---|---|---|
| | 210 | | | | | 215 | | | | | 220 | | | | |

| Ala | Arg | Ala | Trp | Pro | Lys | Met | His | Thr | Val | Asn | Gly | Tyr | Val | Asn | Arg |
|---|---|---|---|---|---|---|---|---|---|---|---|---|---|---|---|
| 225 | | | | | 230 | | | | | 235 | | | | | 240 |

| Ser | Leu | Pro | Gly | Leu | Ile | Gly | Cys | His | Arg | Lys | Ser | Val | Tyr | Trp | His |
|---|---|---|---|---|---|---|---|---|---|---|---|---|---|---|---|
| | | | | 245 | | | | | 250 | | | | | 255 | |

| Val | Ile | Gly | Met | Gly | Thr | Thr | Pro | Glu | Val | His | Ser | Ile | Phe | Leu | Glu |
|---|---|---|---|---|---|---|---|---|---|---|---|---|---|---|---|
| | | | 260 | | | | | 265 | | | | | 270 | | |

| Gly | His | Thr | Phe | Leu | Val | Arg | Asn | His | Arg | Gln | Ala | Ser | Leu | Glu | Ile |

```
              275                 280                 285
Ser Pro Ile Thr Phe Leu Thr Ala Gln Thr Leu Leu Met Asp Leu Gly
290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Pro Gln Leu Arg
                325                 330                 335
Met Lys Asn Asn Glu Glu Ala Glu Asp Tyr Asp Asp Leu Thr Asp
                340                 345                 350
Ser Glu Met Asp Val Val Arg Phe Asp Asp Asn Ser Pro Ser Phe
            355                 360                 365
Ile Gln Ile Arg Ser Val Ala Lys Lys His Pro Lys Thr Trp Val His
370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
            515                 520                 525
Leu Thr Arg Tyr Tyr Ser Ser Phe Val Asn Met Glu Arg Asp Leu Ala
530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
                580                 585                 590
Arg Phe Leu Pro Asn Pro Ala Gly Val Gln Leu Glu Asp Pro Glu Phe
            595                 600                 605
Gln Ala Ser Asn Ile Met His Ser Ile Asn Gly Tyr Val Phe Asp Ser
            610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
                660                 665                 670
Phe Ser Gly Glu Thr Val Phe Met Ser Met Glu Asn Pro Gly Leu Trp
            675                 680                 685
Ile Leu Gly Cys His Asn Ser Asp Phe Arg Asn Arg Gly Met Thr Ala
            690                 695                 700
```

```
Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
            725                 730                 735

Ile Glu Pro Arg Arg Gly Arg Arg Glu Ile Thr Arg Thr Thr Leu
        740                 745                 750

Gln Ser Asp Gln Glu Glu Ile Asp Tyr Asp Asp Thr Ile Ser Val Glu
            755                 760                 765

Met Lys Lys Glu Asp Phe Asp Ile Tyr Asp Glu Asp Glu Asn Gln Ser
770                 775                 780

Pro Arg Ser Phe Gln Lys Lys Thr Arg His Tyr Phe Ile Ala Ala Val
785                 790                 795                 800

Glu Arg Leu Trp Asp Tyr Gly Met Ser Ser Pro His Val Leu Arg
            805                 810                 815

Asn Arg Ala Gln Ser Gly Ser Val Pro Gln Phe Lys Lys Val Val Phe
            820                 825                 830

Gln Glu Phe Thr Asp Gly Ser Phe Thr Gln Pro Leu Tyr Arg Gly Glu
        835                 840                 845

Leu Asn Glu His Leu Gly Leu Leu Gly Pro Tyr Ile Arg Ala Glu Val
        850                 855                 860

Glu Asp Asn Ile Met Val Thr Phe Arg Asn Gln Ala Ser Arg Pro Tyr
865                 870                 875                 880

Ser Phe Tyr Ser Ser Leu Ile Ser Tyr Glu Glu Asp Gln Arg Gln Gly
                885                 890                 895

Ala Glu Pro Arg Lys Asn Phe Val Lys Pro Asn Glu Thr Lys Thr Tyr
            900                 905                 910

Phe Trp Lys Val Gln His His Met Ala Pro Thr Lys Asp Glu Phe Asp
        915                 920                 925

Cys Lys Ala Trp Ala Tyr Phe Ser Asp Val Asp Leu Glu Lys Asp Val
    930                 935                 940

His Ser Gly Leu Ile Gly Pro Leu Leu Val Cys His Thr Asn Thr Leu
945                 950                 955                 960

Asn Pro Ala His Gly Arg Gln Val Thr Val Gln Glu Phe Ala Leu Phe
                965                 970                 975

Phe Thr Ile Phe Asp Glu Thr Lys Ser Trp Tyr Phe Thr Glu Asn Met
            980                 985                 990

Glu Arg Asn Cys Arg Ala Pro Cys Asn Ile Gln Met Glu Asp Pro Thr
        995                 1000                1005

Phe Lys Glu Asn Tyr Arg Phe His Ala Ile Asn Gly Tyr Ile Met
    1010                1015                1020

Asp Thr Leu Pro Gly Leu Val Met Ala Gln Asp Gln Arg Ile Arg
    1025                1030                1035

Trp Tyr Leu Leu Ser Met Gly Ser Asn Glu Asn Ile His Ser Ile
    1040                1045                1050

His Phe Ser Gly His Val Phe Thr Val Arg Lys Lys Glu Glu Tyr
    1055                1060                1065

Lys Met Ala Leu Tyr Asn Leu Tyr Pro Gly Val Phe Glu Thr Val
    1070                1075                1080

Glu Met Leu Pro Ser Lys Ala Gly Ile Trp Arg Val Glu Cys Leu
    1085                1090                1095

Ile Gly Glu His Leu His Ala Gly Met Ser Thr Leu Phe Leu Val
    1100                1105                1110
```

```
Tyr Ser Asn Lys Cys Gln Thr Pro Leu Gly Met Ala Ser Gly His
1115                1120                1125

Ile Arg Asp Phe Gln Ile Thr Ala Ser Gly Gln Tyr Gly Gln Trp
1130                1135                1140

Ala Pro Lys Leu Ala Arg Leu His Tyr Ser Gly Ser Ile Asn Ala
1145                1150                1155

Trp Ser Thr Lys Glu Pro Phe Ser Trp Ile Lys Val Asp Leu Leu
1160                1165                1170

Ala Pro Met Ile Ile His Gly Ile Lys Thr Gln Gly Ala Arg Gln
1175                1180                1185

Lys Phe Ser Ser Leu Tyr Ile Ser Gln Phe Ile Ile Met Tyr Ser
1190                1195                1200

Leu Asp Gly Lys Lys Trp Gln Thr Tyr Arg Gly Asn Ser Thr Gly
1205                1210                1215

Thr Leu Met Val Phe Phe Gly Asn Val Asp Ser Ser Gly Ile Lys
1220                1225                1230

His Asn Ile Phe Asn Pro Pro Ile Ile Ala Arg Tyr Ile Arg Leu
1235                1240                1245

His Pro Thr His Tyr Ser Ile Arg Ser Thr Leu Arg Met Glu Leu
1250                1255                1260

Met Gly Cys Asp Leu Asn Ser Cys Ser Met Pro Leu Gly Met Glu
1265                1270                1275

Ser Lys Ala Ile Ser Asp Ala Gln Ile Thr Ala Ser Ser Tyr Phe
1280                1285                1290

Thr Asn Met Phe Ala Thr Trp Ser Pro Ser Lys Ala Arg Leu His
1295                1300                1305

Leu Gln Gly Arg Ser Asn Ala Trp Arg Pro Gln Val Asn Asn Pro
1310                1315                1320

Lys Glu Trp Leu Gln Val Asp Phe Gln Lys Thr Met Lys Val Thr
1325                1330                1335

Gly Val Thr Thr Gln Gly Val Lys Ser Leu Leu Thr Ser Met Tyr
1340                1345                1350

Val Lys Glu Phe Leu Ile Ser Ser Ser Gln Asp Gly His Gln Trp
1355                1360                1365

Thr Leu Phe Phe Gln Asn Gly Lys Val Lys Val Phe Gln Gly Asn
1370                1375                1380

Gln Asp Ser Phe Thr Pro Val Val Asn Ser Leu Asp Pro Pro Leu
1385                1390                1395

Leu Thr Arg Tyr Leu Arg Ile His Pro Gln Ser Trp Val His Gln
1400                1405                1410

Ile Ala Leu Arg Met Glu Val Leu Gly Cys Glu Ala Gln Asp Leu
1415                1420                1425

Tyr Thr Gly Asp Ala His Lys Ser Glu Val Ala His Arg Phe Lys
1430                1435                1440

Asp Leu Gly Glu Glu Asn Phe Lys Ala Leu Val Leu Ile Ala Phe
1445                1450                1455

Ala Gln Tyr Leu Gln Gln Cys Pro Phe Glu Asp His Val Lys Leu
1460                1465                1470

Val Asn Glu Val Thr Glu Phe Ala Lys Thr Cys Val Ala Asp Glu
1475                1480                1485

Ser Ala Glu Asn Cys Asp Lys Ser Leu His Thr Leu Phe Gly Asp
1490                1495                1500

Lys Leu Cys Thr Val Ala Thr Leu Arg Glu Thr Tyr Gly Glu Met
```

```
                1505                1510                1515

Ala Asp Cys Cys Ala Lys Gln Glu Pro Glu Arg Asn Glu Cys Phe
    1520                1525                1530

Leu Gln His Lys Asp Asp Asn Pro Asn Leu Pro Arg Leu Val Arg
    1535                1540                1545

Pro Glu Val Asp Val Met Cys Thr Ala Phe His Asp Asn Glu Glu
    1550                1555                1560

Thr Phe Leu Lys Lys Tyr Leu Tyr Glu Ile Ala Arg Arg His Pro
    1565                1570                1575

Tyr Phe Tyr Ala Pro Glu Leu Leu Phe Phe Ala Lys Arg Tyr Lys
    1580                1585                1590

Ala Ala Phe Thr Glu Cys Cys Gln Ala Ala Asp Lys Ala Ala Cys
    1595                1600                1605

Leu Leu Pro Lys Leu Asp Glu Leu Arg Asp Glu Gly Lys Ala Ser
    1610                1615                1620

Ser Ala Lys Gln Arg Leu Lys Cys Ala Ser Leu Gln Lys Phe Gly
    1625                1630                1635

Glu Arg Ala Phe Lys Ala Trp Ala Val Ala Arg Leu Ser Gln Arg
    1640                1645                1650

Phe Pro Lys Ala Glu Phe Ala Glu Val Ser Lys Leu Val Thr Asp
    1655                1660                1665

Leu Thr Lys Val His Thr Glu Cys Cys His Gly Asp Leu Leu Glu
    1670                1675                1680

Cys Ala Asp Asp Arg Ala Asp Leu Ala Lys Tyr Ile Cys Glu Asn
    1685                1690                1695

Gln Asp Ser Ile Ser Ser Lys Leu Lys Glu Cys Cys Glu Lys Pro
    1700                1705                1710

Leu Leu Glu Lys Ser His Cys Ile Ala Glu Val Glu Asn Asp Glu
    1715                1720                1725

Met Pro Ala Asp Leu Pro Ser Leu Ala Ala Asp Phe Val Glu Ser
    1730                1735                1740

Lys Asp Val Cys Lys Asn Tyr Ala Glu Ala Lys Asp Val Phe Leu
    1745                1750                1755

Gly Met Phe Leu Tyr Glu Tyr Ala Arg Arg His Pro Asp Tyr Ser
    1760                1765                1770

Val Val Leu Leu Leu Arg Leu Ala Lys Thr Tyr Glu Thr Thr Leu
    1775                1780                1785

Glu Lys Cys Cys Ala Ala Ala Asp Pro His Glu Cys Tyr Ala Lys
    1790                1795                1800

Val Phe Asp Glu Phe Lys Pro Leu Val Glu Glu Pro Gln Asn Leu
    1805                1810                1815

Ile Lys Gln Asn Cys Glu Leu Phe Glu Gln Leu Gly Glu Tyr Lys
    1820                1825                1830

Phe Gln Asn Ala Leu Leu Val Arg Tyr Thr Lys Lys Val Pro Gln
    1835                1840                1845

Val Ser Thr Pro Thr Leu Val Glu Val Ser Arg Asn Leu Gly Lys
    1850                1855                1860

Val Gly Ser Lys Cys Cys Lys His Pro Glu Ala Lys Arg Met Pro
    1865                1870                1875

Cys Ala Glu Asp Tyr Leu Ser Val Val Leu Asn Gln Leu Cys Val
    1880                1885                1890

Leu His Glu Lys Thr Pro Val Ser Asp Arg Val Thr Lys Cys Cys
    1895                1900                1905
```

| | | | | | | | | | | |
|---|---|---|---|---|---|---|---|---|---|---|
|Thr|Glu|Ser|Leu|Val|Asn|Arg|Arg|Pro|Cys|Phe|Ser|Ala|Leu|Glu|
| |1910| | | |1915| | | |1920| |

Val Asp Glu Thr Tyr Val Pro Lys Glu Phe Asn Ala Glu Thr Phe
    1925            1930            1935

Thr Phe His Ala Asp Ile Cys Thr Leu Ser Glu Lys Glu Arg Gln
    1940            1945            1950

Ile Lys Lys Gln Thr Ala Leu Val Glu Leu Val Lys His Lys Pro
    1955            1960            1965

Lys Ala Thr Lys Glu Gln Leu Lys Ala Val Met Asp Asp Phe Ala
    1970            1975            1980

Ala Phe Val Glu Lys Cys Cys Lys Ala Asp Asp Lys Glu Thr Cys
    1985            1990            1995

Phe Ala Glu Glu Gly Lys Lys Leu Val Ala Ala Ser Gln Ala Ala
    2000            2005            2010

Leu Gly Leu
    2015

<210> SEQ ID NO 10
<211> LENGTH: 31
<212> TYPE: DNA
<213> ORGANISM: Artificial
<220> FEATURE:
<223> OTHER INFORMATION: Primer

<400> SEQUENCE: 10
gcgaccggtg atgacaactc tccttccttt a                               31

<210> SEQ ID NO 11
<211> LENGTH: 31
<212> TYPE: DNA
<213> ORGANISM: Artificial
<220> FEATURE:
<223> OTHER INFORMATION: Primer

<400> SEQUENCE: 11
gcgaccggtc aagttttag gatgcttctt g                                31

<210> SEQ ID NO 12
<211> LENGTH: 27
<212> TYPE: DNA
<213> ORGANISM: Artificial
<220> FEATURE:
<223> OTHER INFORMATION: Primer

<400> SEQUENCE: 12
gcgaccggtt cgagcggggg atctggc                                    27

<210> SEQ ID NO 13
<211> LENGTH: 28
<212> TYPE: DNA
<213> ORGANISM: Artificial
<220> FEATURE:
<223> OTHER INFORMATION: Primer

<400> SEQUENCE: 13
gcgaccggtg atcccgacc ctccagag                                    28

<210> SEQ ID NO 14
<211> LENGTH: 7020
<212> TYPE: DNA
<213> ORGANISM: Homo Sapiens -continued

<400> SEQUENCE: 14

```
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc caaaatcttt tccattcaac     180
acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaaagactt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggatagggat     720
gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
accactcctg aagtgcactc aatattcctc gaaggtcaca catttcttgt gaggaaccat     900
cgccaggcgt ccttggaaat ctcgccaata actttcctta ctgctcaaac actcttgatg     960
gaccttggac agtttctact gttttgtcat atctcttccc accaacatga tggcatggaa    1020
gcttatgtca agtagacag ctgtccagag aaccccaac tacgaatgaa aaataatgaa      1080
gaagcggaag actatgatga tgatcttact gattctgaaa tggatgtggt caggtttgat    1140
gatgacaact ctccttcctt tatccaaatt cgctcagttg ccaagaagca tcctaaaact    1200
tgggtacatt acattgctgc tgaagaggag gactgggact atgctcccct agtcctcgcc    1260
cccgatgaca gaagttataa aagtcaatat ttgaacaatg gccctcagcg gattggtagg    1320
aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgtttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccct caaacacaaa    2040
atggtctatg aagacacact cacccctattc ccattctcag agaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga attcaagaca ccctagcact aggcaaaagc aatttaatgc caccacaatt    2340
```

```
ccagaaaatg acatagagaa gactgaccct tggtttgcac acagaacacc tatgcctaaa    2400
atacaaaatg tctcctctag tgatttgttg atgctcttgc gacagagtcc tactccacat    2460
gggctatcct tatctgatct ccaagaagcc aaatatgaga cttttctga tgatccatca     2520 cctggagcaa tagacagtaa taacagcctg tctgaaatga cacacttcag gccacagctc    2580
catcacagtg gggacatggt atttaccct gagtcaggcc tccaattaag attaaatgag     2640
aaactgggga caactgcagc aacagagttg aagaaacttg atttcaaagt ttctagtaca    2700
tcaaataatc tgatttcaac aattccatca gacaatttgg cagcaggtac tgataataca    2760
agttccttag gaccccaag tatgccagtt cattatgata gtcaattaga taccactcta     2820
tttggcaaaa agtcatctcc ccttactgag tctggtggac ctctgagctt gagtgaagaa    2880
aataatgatt caaagttgtt agaatcaggt ttaatgaata gccaagaaag ttcatgggga    2940
aaaaatgtat cgtcaacaga gagtggtagg ttatttaaag ggaaagagc tcatggacct      3000 gctttgttga ctaaagataa tgccttattc aaagttagca tctctttgtt aaagacaaac    3060
aaaacttcca ataattcagc aactaataga aagactcaca ttgatggccc atcattatta    3120
attgagaata gtccatcagt ctggcaaaat atattagaaa gtgacactga gtttaaaaaa    3180
gtgacacctt tgattcatga cagaatgctt atggacaaaa atgctacagc tttgaggcta    3240
aatcatatgt caaataaaac tacttcatca aaaaacatgg aaatggtcca acagaaaaaa    3300
gagggcccca ttccaccaga tgcacaaaat ccagatatgt cgttctttaa gatgctattc    3360
ttgccagaat cagcaaggtg gatacaaagg actcatggaa agaactctct gaactctggg    3420
caaggcccca gtccaaagca attagtatcc ttaggaccag aaaaatctgt ggaaggtcag    3480
aatttcttgt ctgagaaaaa caagtggta gtaggaaagg gtgaatttac aaaggacgta      3540
ggactcaaag agatggtttt tccaagcagc agaaacctat ttcttactaa cttggataat    3600
ttacatgaaa ataatacaca caatcaagaa aaaaaattc aggaagaaat agaaagaag      3660 gaaacattaa tccaagagaa tgtagttttg cctcagatac atacagtgac tggcactaag    3720 aattcatga agaaccttt cttactgagc actaggcaaa atgtagaagg ttcatatgac      3780
ggggcatatg ctccagtact tcaagatttt aggtcattaa atgattcaac aaatagaaca    3840
aagaaacaca cagctcattt ctcaaaaaaa gggaggaag aaaacttgga aggcttggga     3900
aatcaaacca agcaaattgt agagaaatat gcatgcacca caaggatatc tcctaataca    3960
agccagcaga atttttgtcac gcaacgtagt aagagagctt tgaaacaatt cagactccca    4020
ctagaagaaa cagaacttga aaaaggata attgtggatg cacctcaac ccagtggtcc      4080 aaaaacatga acatttgac cccgagcacc ctcacacaga tagactacaa tgagaaggag    4140
aaaggggcca ttactcagtc tcccttatca gattgcctta cgaggagtca tagcatccct    4200
caagcaaata gatctccatt acccattgca aaggtatcat catttccatc tattagacct    4260
atatatctga ccaggqtcct attccaagac aactcttctc atcttccagc agcatcttat    4320
agaaagaaag attctggggt ccaagaaagc agtcatttct tacaaggagc caaaaaaaat    4380
aacctttctt tagccattct aaccttggag atgactggtg atcaaagaga ggttggctcc    4440
ctggggacaa gtgccacaaa ttcagtcaca tacaagaaag ttgagaacac tgttctcccg    4500
aaaccagact tgcccaaaac atctggcaaa gttgaattgc ttccaaaagt tcacatttat    4560
cagaaggacc tattccctac ggaaactagc aatgggctct ctggccatct ggatctcgtg    4620
gaagggagcc ttcttcaggg aacagaggga gcgattaagt ggaatgaagc aaacagacct    4680
```

```
ggaaaagttc cctttctgag agtagcaaca gaaagctctg caaagactcc ctccaagcta    4740
ttggatcctc ttgcttggga taaccactat ggtactcaga taccaaaaga agagtggaaa    4800
tcccaagaga agtcaccaga aaaaacagct tttaagaaaa aggataccat tttgtccctg    4860
aacgcttgtg aaagcaatca tgcaatagca gcaataaatg agggacaaaa taagcccgaa    4920
atagaagtca cctgggcaaa gcaaggtagg actgaaaggc tgtgctctca aaacccacca    4980
gtcttgaaac gccatcaacg ggaaataact cgtactactc ttcagtcaga tcaagaggaa    5040
attgactatg atgataccat atcagttgaa atgaagaagg aagattttga catttatgat    5100
gaggatgaaa atcagagccc ccgcagcttt caaaagaaaa cacgacacta ttttattgct    5160
gcagtggaga ggctctggga ttatgggatg agtagctccc cacatgttct aagaaacagg    5220
gctcagagtg gcagtgtccc tcagttcaag aaagttgttt ccaggaatt tactgatggc    5280
tcctttactc agcccttata ccgtggagaa ctaaatgaac atttgggact cctggggcca    5340
tatataagag cagaagttga agataatatc atggtaactt tcagaaatca ggcctctcgt    5400
ccctattcct tctattctag ccttatttct tatgaggaag atcagaggca aggagcagaa    5460
cctagaaaaa actttgtcaa gcctaatgaa accaaaactt acttttggaa agtgcaacat    5520
catatggcac ccactaaaga tgagtttgac tgcaaagcct gggcttattt ctctgatgtt    5580
gacctggaaa aagatgtgca ctcaggcctg attggacccc ttctggtctg ccacactaac    5640
acactgaacc ctgctcatgg gagacaagtg acagtacagg aatttgctct gtttttcacc    5700
atctttgatg agaccaaaag ctggtacttc actgaaaata tggaaagaaa ctgcagggct    5760
ccctgcaata tccagatgga agatcccact tttaaagaga attatcgctt ccatgcaatc    5820
aatggctaca ataatggatac actacctggc ttagtaatgg ctcaggatca aaggattcga    5880
tggtatctgc tcagcatggg cagcaatgaa aacatccatt ctattcattt cagtggacat    5940
gtgttcactg tacgaaaaaa agaggagtat aaaatggcac tgtacaatct ctatccaggt    6000
gttttttgaga cagtggaaat gttaccatcc aaagctggaa tttggcgggt ggaatgcctt    6060
attggcgagc atctacatgc tgggatgagc acacttttttc tggtgtacag caataagtgt    6120
cagactcccc tggaatggc ttctggacac attagagatt ttcagattac agcttcagga    6180
caatatggac agtgggcccc aaagctggcc agacttcatt attccggatc aatcaatgcc    6240
tggagcacca aggagccctt ttcttggatc aaggtggatc tgttggcacc aatgattatt    6300
cacggcatca agacccaggg tgcccgtcag aagttctcca gcctctacat ctctcagttt    6360
atcatcatgt atagtcttga tgggaagaag tggcagactt atcgaggaaa ttccactgga    6420
accttaatgg tcttctttgg caatgtggat tcatctggga taaaacacaa tattttttaac    6480
cctccaatta ttgctcgata catccgttg cacccaactc attatagcat tcgcagcact    6540
cttcgcatgg agttgatggg ctgtgattta aatagttgca gcatgccatt gggaatggag    6600
agtaaagcaa tatcagatgc acagattact gcttcatcct actttaccaa tatgtttgcc    6660
acctggtctc cttcaaaagc tcgacttcac ctccaaggga ggagtaatgc ctggagacct    6720
caggtgaata tccaaaaaga gtggctgcaa gtggacttcc agaagacaat gaaagtcaca    6780
ggagtaacta ctcagggagt aaaatctctg cttaccagca tgtatgtgaa ggagttcctc    6840
atctccagca gtcaagatgg ccatcagtgg actctctttt ttcagaatgg caaagtaaag    6900
gttttttcagg gaaatcaaga ctccttcaca cctgtggtga actctctaga cccaccgtta    6960
ctgactcgct accttcgaat tcaccccag agttgggtgc accagattgc cctgaggatg    7020
```

```
<210> SEQ ID NO 15
<211> LENGTH: 2332
<212> TYPE: PRT
<213> ORGANISM: Homo sapiens

<400> SEQUENCE: 15

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380
```

```
Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
            405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
            485                 490                 495

His Leu Lys Asp Phe Pro Ile Leu Pro Gly Glu Ile Phe Lys Tyr Lys
        500                 505                 510

Trp Thr Val Thr Val Glu Asp Gly Pro Thr Lys Ser Asp Pro Arg Cys
    515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
            565                 570                 575

Ser Val Phe Asp Glu Asn Arg Ser Trp Tyr Leu Thr Glu Asn Ile Gln
        580                 585                 590

Arg Phe Leu Pro Asn Pro Ala Gly Val Gln Leu Glu Asp Pro Glu Phe
    595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
            645                 650                 655

Thr Phe Lys His Lys Met Val Tyr Glu Asp Thr Leu Thr Leu Phe Pro
        660                 665                 670

Phe Ser Gly Glu Thr Val Phe Met Ser Met Glu Asn Pro Gly Leu Trp
    675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
            725                 730                 735

Ile Glu Pro Arg Ser Phe Ser Gln Asn Ser Arg His Arg Ser Thr Arg
        740                 745                 750

Gln Lys Gln Phe Asn Ala Thr Thr Ile Pro Glu Asn Asp Ile Glu Lys
    755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
```

-continued

```
                805                 810                 815
Ser Asp Asp Pro Ser Pro Gly Ala Ile Asp Ser Asn Asn Ser Leu Ser
            820                 825                 830
Glu Met Thr His Phe Arg Pro Gln Leu His His Ser Gly Asp Met Val
            835                 840                 845
Phe Thr Pro Glu Ser Gly Leu Gln Leu Arg Leu Asn Glu Lys Leu Gly
            850                 855                 860
Thr Thr Ala Ala Thr Glu Leu Lys Lys Leu Asp Phe Lys Val Ser Ser
865                 870                 875                 880
Thr Ser Asn Asn Leu Ile Ser Thr Ile Pro Ser Asp Asn Leu Ala Ala
                885                 890                 895
Gly Thr Asp Asn Thr Ser Ser Leu Gly Pro Pro Ser Met Pro Val His
            900                 905                 910
Tyr Asp Ser Gln Leu Asp Thr Thr Leu Phe Gly Lys Lys Ser Ser Pro
            915                 920                 925
Leu Thr Glu Ser Gly Gly Pro Leu Ser Leu Ser Glu Glu Asn Asn Asp
            930                 935                 940
Ser Lys Leu Leu Glu Ser Gly Leu Met Asn Ser Gln Glu Ser Ser Trp
945                 950                 955                 960
Gly Lys Asn Val Ser Ser Thr Glu Ser Gly Arg Leu Phe Lys Gly Lys
                965                 970                 975
Arg Ala His Gly Pro Ala Leu Leu Thr Lys Asp Asn Ala Leu Phe Lys
            980                 985                 990
Val Ser Ile Ser Leu Leu Lys Thr Asn Lys Thr Ser Asn Asn Ser Ala
            995                 1000                1005
Thr Asn Arg Lys Thr His Ile Asp Gly Pro Ser Leu Leu Ile Glu
            1010                1015                1020
Asn Ser Pro Ser Val Trp Gln Asn Ile Leu Glu Ser Asp Thr Glu
            1025                1030                1035
Phe Lys Lys Val Thr Pro Leu Ile His Asp Arg Met Leu Met Asp
            1040                1045                1050
Lys Asn Ala Thr Ala Leu Arg Leu Asn His Met Ser Asn Lys Thr
            1055                1060                1065
Thr Ser Ser Lys Asn Met Glu Met Val Gln Gln Lys Lys Glu Gly
            1070                1075                1080
Pro Ile Pro Pro Asp Ala Gln Asn Pro Asp Met Ser Phe Phe Lys
            1085                1090                1095
Met Leu Phe Leu Pro Glu Ser Ala Arg Trp Ile Gln Arg Thr His
            1100                1105                1110
Gly Lys Asn Ser Leu Asn Ser Gly Gln Gly Pro Ser Pro Lys Gln
            1115                1120                1125
Leu Val Ser Leu Gly Pro Glu Lys Ser Val Glu Gly Gln Asn Phe
            1130                1135                1140
Leu Ser Glu Lys Asn Lys Val Val Val Gly Lys Gly Glu Phe Thr
            1145                1150                1155
Lys Asp Val Gly Leu Lys Glu Met Val Phe Pro Ser Ser Arg Asn
            1160                1165                1170
Leu Phe Leu Thr Asn Leu Asp Asn Leu His Glu Asn Asn Thr His
            1175                1180                1185
Asn Gln Glu Lys Lys Ile Gln Glu Glu Ile Glu Lys Lys Glu Thr
            1190                1195                1200
Leu Ile Gln Glu Asn Val Val Leu Pro Gln Ile His Thr Val Thr
            1205                1210                1215
```

```
Gly Thr Lys Asn Phe Met Lys Asn Leu Phe Leu Leu Ser Thr Arg
1220                1225                1230

Gln Asn Val Glu Gly Ser Tyr Asp Gly Ala Tyr Ala Pro Val Leu
1235                1240                1245

Gln Asp Phe Arg Ser Leu Asn Asp Ser Thr Asn Arg Thr Lys Lys
1250                1255                1260

His Thr Ala His Phe Ser Lys Lys Gly Glu Glu Asn Leu Glu
1265                1270                1275

Gly Leu Gly Asn Gln Thr Lys Gln Ile Val Glu Lys Tyr Ala Cys
1280                1285                1290

Thr Thr Arg Ile Ser Pro Asn Thr Ser Gln Gln Asn Phe Val Thr
1295                1300                1305

Gln Arg Ser Lys Arg Ala Leu Lys Gln Phe Arg Leu Pro Leu Glu
1310                1315                1320

Glu Thr Glu Leu Glu Lys Arg Ile Ile Val Asp Asp Thr Ser Thr
1325                1330                1335

Gln Trp Ser Lys Asn Met Lys His Leu Thr Pro Ser Thr Leu Thr
1340                1345                1350

Gln Ile Asp Tyr Asn Glu Lys Glu Lys Gly Ala Ile Thr Gln Ser
1355                1360                1365

Pro Leu Ser Asp Cys Leu Thr Arg Ser His Ser Ile Pro Gln Ala
1370                1375                1380

Asn Arg Ser Pro Leu Pro Ile Ala Lys Val Ser Phe Pro Ser
1385                1390                1395

Ile Arg Pro Ile Tyr Leu Thr Arg Val Leu Phe Gln Asp Asn Ser
1400                1405                1410

Ser His Leu Pro Ala Ala Ser Tyr Arg Lys Lys Asp Ser Gly Val
1415                1420                1425

Gln Glu Ser Ser His Phe Leu Gln Gly Ala Lys Lys Asn Asn Leu
1430                1435                1440

Ser Leu Ala Ile Leu Thr Leu Glu Met Thr Gly Asp Gln Arg Glu
1445                1450                1455

Val Gly Ser Leu Gly Thr Ser Ala Thr Asn Ser Val Thr Tyr Lys
1460                1465                1470

Lys Val Glu Asn Thr Val Leu Pro Lys Pro Asp Leu Pro Lys Thr
1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
1595                1600                1605
```

```
Ala Ile Ala Ala Ile Asn Glu Gly Gln Asn Lys Pro Glu Ile Glu
    1610            1615                1620

Val Thr Trp Ala Lys Gln Gly Arg Thr Glu Arg Leu Cys Ser Gln
    1625            1630                1635

Asn Pro Pro Val Leu Lys Arg His Gln Arg Glu Ile Thr Arg Thr
    1640            1645                1650

Thr Leu Gln Ser Asp Gln Glu Glu Ile Asp Tyr Asp Asp Thr Ile
    1655            1660                1665

Ser Val Glu Met Lys Lys Glu Asp Phe Asp Ile Tyr Asp Glu Asp
    1670            1675                1680

Glu Asn Gln Ser Pro Arg Ser Phe Gln Lys Lys Thr Arg His Tyr
    1685            1690                1695

Phe Ile Ala Ala Val Glu Arg Leu Trp Asp Tyr Gly Met Ser Ser
    1700            1705                1710

Ser Pro His Val Leu Arg Asn Arg Ala Gln Ser Gly Ser Val Pro
    1715            1720                1725

Gln Phe Lys Lys Val Val Phe Gln Glu Phe Thr Asp Gly Ser Phe
    1730            1735                1740

Thr Gln Pro Leu Tyr Arg Gly Glu Leu Asn Glu His Leu Gly Leu
    1745            1750                1755

Leu Gly Pro Tyr Ile Arg Ala Glu Val Glu Asp Asn Ile Met Val
    1760            1765                1770

Thr Phe Arg Asn Gln Ala Ser Arg Pro Tyr Ser Phe Tyr Ser Ser
    1775            1780                1785

Leu Ile Ser Tyr Glu Glu Asp Gln Arg Gln Gly Ala Glu Pro Arg
    1790            1795                1800

Lys Asn Phe Val Lys Pro Asn Glu Thr Lys Thr Tyr Phe Trp Lys
    1805            1810                1815

Val Gln His His Met Ala Pro Thr Lys Asp Glu Phe Asp Cys Lys
    1820            1825                1830

Ala Trp Ala Tyr Phe Ser Asp Val Asp Leu Glu Lys Asp Val His
    1835            1840                1845

Ser Gly Leu Ile Gly Pro Leu Leu Val Cys His Thr Asn Thr Leu
    1850            1855                1860

Asn Pro Ala His Gly Arg Gln Val Thr Val Gln Glu Phe Ala Leu
    1865            1870                1875

Phe Phe Thr Ile Phe Asp Glu Thr Lys Ser Trp Tyr Phe Thr Glu
    1880            1885                1890

Asn Met Glu Arg Asn Cys Arg Ala Pro Cys Asn Ile Gln Met Glu
    1895            1900                1905

Asp Pro Thr Phe Lys Glu Asn Tyr Arg Phe His Ala Ile Asn Gly
    1910            1915                1920

Tyr Ile Met Asp Thr Leu Pro Gly Leu Val Met Ala Gln Asp Gln
    1925            1930                1935

Arg Ile Arg Trp Tyr Leu Leu Ser Met Gly Ser Asn Glu Asn Ile
    1940            1945                1950

His Ser Ile His Phe Ser Gly His Val Phe Thr Val Arg Lys Lys
    1955            1960                1965

Glu Glu Tyr Lys Met Ala Leu Tyr Asn Leu Tyr Pro Gly Val Phe
    1970            1975                1980

Glu Thr Val Glu Met Leu Pro Ser Lys Ala Gly Ile Trp Arg Val
    1985            1990                1995

Glu Cys Leu Ile Gly Glu His Leu His Ala Gly Met Ser Thr Leu
```

```
                2000                2005                2010
Phe Leu Val Tyr Ser Asn Lys Cys Gln Thr Pro Leu Gly Met Ala
    2015                2020                2025

Ser Gly His Ile Arg Asp Phe Gln Ile Thr Ala Ser Gly Gln Tyr
    2030                2035                2040

Gly Gln Trp Ala Pro Lys Leu Ala Arg Leu His Tyr Ser Gly Ser
    2045                2050                2055

Ile Asn Ala Trp Ser Thr Lys Glu Pro Phe Ser Trp Ile Lys Val
    2060                2065                2070

Asp Leu Leu Ala Pro Met Ile Ile His Gly Ile Lys Thr Gln Gly
    2075                2080                2085

Ala Arg Gln Lys Phe Ser Ser Leu Tyr Ile Ser Gln Phe Ile Ile
    2090                2095                2100

Met Tyr Ser Leu Asp Gly Lys Lys Trp Gln Thr Tyr Arg Gly Asn
    2105                2110                2115

Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Ser Gln Asp Gly
    2255                2260                2265

His Gln Trp Thr Leu Phe Phe Gln Asn Gly Lys Val Lys Val Phe
    2270                2275                2280

Gln Gly Asn Gln Asp Ser Phe Thr Pro Val Val Asn Ser Leu Asp
    2285                2290                2295

Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
    2315                2320                2325

Gln Asp Leu Tyr
    2330

<210> SEQ ID NO 16
<211> LENGTH: 585
<212> TYPE: PRT
<213> ORGANISM: Homo sapiens

<400> SEQUENCE: 16

Asp Ala His Lys Ser Glu Val Ala His Arg Phe Lys Asp Leu Gly Glu
1               5                   10                  15
```

-continued

```
Glu Asn Phe Lys Ala Leu Val Leu Ile Ala Phe Ala Gln Tyr Leu Gln
             20                  25                  30
Gln Cys Pro Phe Glu Asp His Val Lys Leu Val Asn Glu Val Thr Glu
         35                  40                  45
Phe Ala Lys Thr Cys Val Ala Asp Glu Ser Ala Glu Asn Cys Asp Lys
     50                  55                  60
Ser Leu His Thr Leu Phe Gly Asp Lys Leu Cys Thr Val Ala Thr Leu
 65                  70                  75                  80
Arg Glu Thr Tyr Gly Glu Met Ala Asp Cys Cys Ala Lys Gln Glu Pro
                 85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
```

```
                435                 440                 445
Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 17
<211> LENGTH: 30
<212> TYPE: DNA
<213> ORGANISM: Artificial
<220> FEATURE:
<223> OTHER INFORMATION: Primer

<400> SEQUENCE: 17
ttcgaattcc cgcagccctc atttgcaggg                                    30

<210> SEQ ID NO 18
<211> LENGTH: 31
<212> TYPE: DNA
<213> ORGANISM: Artificial
<220> FEATURE:
<223> OTHER INFORMATION: Primer

<400> SEQUENCE: 18
tccgaattcc ggcagcagca ggcacccatg c                                  31

<210> SEQ ID NO 19
<211> LENGTH: 25
<212> TYPE: DNA
<213> ORGANISM: Artificial
<220> FEATURE:
<223> OTHER INFORMATION: Primer

<400> SEQUENCE: 19
gcggcggccg cgagccccat ttccc                                         25

<210> SEQ ID NO 20
<211> LENGTH: 18
<212> TYPE: DNA
<213> ORGANISM: Artificial
<220> FEATURE:
<223> OTHER INFORMATION: Primer

<400> SEQUENCE: 20
gagagggagt actcaccc                                                 18

<210> SEQ ID NO 21
```

<211> LENGTH: 27
<212> TYPE: DNA
<213> ORGANISM: Artificial
<220> FEATURE:
<223> OTHER INFORMATION: Primer

<400> SEQUENCE: 21
ggaagtgcag caagtcgagc gggggat                                                27

<210> SEQ ID NO 22
<211> LENGTH: 27
<212> TYPE: DNA
<213> ORGANISM: Artificial
<220> FEATURE:
<223> OTHER INFORMATION: Primer

<400> SEQUENCE: 22
atcccccgct cgacttgctg cacttcc                                                27

<210> SEQ ID NO 23
<211> LENGTH: 585
<212> TYPE: PRT
<213> ORGANISM: Homo sapiens

<400> SEQUENCE: 23

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
```

```
                260                 265                 270
Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 24
<211> LENGTH: 2813
<212> TYPE: PRT
<213> ORGANISM: homo sapiens

<400> SEQUENCE: 24

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45
```

-continued

```
Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                    85                  90                  95

Phe Val Asn Gly Thr Val Thr Gln Gly Asp Gln Arg Val Ser Met Pro
                100                 105                 110

Tyr Ala Ser Lys Gly Leu Tyr Leu Glu Thr Glu Ala Gly Tyr Tyr Lys
                115                 120                 125

Leu Ser Gly Glu Ala Tyr Gly Phe Val Ala Arg Ile Asp Gly Ser Gly
130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
                180                 185                 190

Leu Ser Ser Gly Glu Gln Trp Cys Glu Arg Ala Ser Pro Pro Ser Ser
                195                 200                 205

Ser Cys Asn Ile Ser Ser Gly Glu Met Gln Lys Gly Leu Trp Glu Gln
210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
                260                 265                 270

Arg Thr Cys Ala Gln Glu Gly Met Val Leu Tyr Gly Trp Thr Asp His
                275                 280                 285

Ser Ala Cys Ser Pro Val Cys Pro Ala Gly Met Glu Tyr Arg Gln Cys
                290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                    325                 330                 335

Leu Asp Glu Gly Leu Cys Val Glu Ser Thr Glu Cys Pro Cys Val His
                340                 345                 350

Ser Gly Lys Arg Tyr Pro Pro Gly Thr Ser Leu Ser Arg Asp Cys Asn
                355                 360                 365

Thr Cys Ile Cys Arg Asn Ser Gln Trp Ile Cys Ser Asn Glu Glu Cys
                370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
                420                 425                 430

Ala Asp Asp Arg Asp Ala Val Cys Thr Arg Ser Val Thr Val Arg Leu
                435                 440                 445

Pro Gly Leu His Asn Ser Leu Val Lys Leu Lys His Gly Ala Gly Val
450                 455                 460

Ala Met Asp Gly Gln Asp Ile Gln Leu Pro Leu Leu Lys Gly Asp Leu
```

```
            465                 470                 475                 480
        Arg Ile Gln His Thr Val Thr Ala Ser Val Arg Leu Ser Tyr Gly Glu
                            485                 490                 495
        Asp Leu Gln Met Asp Trp Asp Gly Arg Gly Arg Leu Leu Val Lys Leu
                        500                 505                 510
        Ser Pro Val Tyr Ala Gly Lys Thr Cys Gly Leu Cys Gly Asn Tyr Asn
                    515                 520                 525
        Gly Asn Gln Gly Asp Asp Phe Leu Thr Pro Ser Gly Leu Ala Glu Pro
                530                 535                 540
        Arg Val Glu Asp Phe Gly Asn Ala Trp Lys Leu His Gly Asp Cys Gln
        545                 550                 555                 560
        Asp Leu Gln Lys Gln His Ser Asp Pro Cys Ala Leu Asn Pro Arg Met
                        565                 570                 575
        Thr Arg Phe Ser Glu Glu Ala Cys Ala Val Leu Thr Ser Pro Thr Phe
                    580                 585                 590
        Glu Ala Cys His Arg Ala Val Ser Pro Leu Pro Tyr Leu Arg Asn Cys
                595                 600                 605
        Arg Tyr Asp Val Cys Ser Cys Ser Asp Gly Arg Glu Cys Leu Cys Gly
        610                 615                 620
        Ala Leu Ala Ser Tyr Ala Ala Ala Cys Ala Gly Arg Gly Val Arg Val
        625                 630                 635                 640
        Ala Trp Arg Glu Pro Gly Arg Cys Glu Leu Asn Cys Pro Lys Gly Gln
                        645                 650                 655
        Val Tyr Leu Gln Cys Gly Thr Pro Cys Asn Leu Thr Cys Arg Ser Leu
                    660                 665                 670
        Ser Tyr Pro Asp Glu Glu Cys Asn Glu Ala Cys Leu Glu Gly Cys Phe
                675                 680                 685
        Cys Pro Pro Gly Leu Tyr Met Asp Glu Arg Gly Asp Cys Val Pro Lys
        690                 695                 700
        Ala Gln Cys Pro Cys Tyr Tyr Asp Gly Glu Ile Phe Gln Pro Glu Asp
        705                 710                 715                 720
        Ile Phe Ser Asp His His Thr Met Cys Tyr Cys Glu Asp Gly Phe Met
                        725                 730                 735
        His Cys Thr Met Ser Gly Val Pro Gly Ser Leu Leu Pro Asp Ala Val
                    740                 745                 750
        Leu Ser Ser Pro Leu Ser His Arg Ser Lys Arg Ser Leu Ser Cys Arg
                755                 760                 765
        Pro Pro Met Val Lys Leu Val Cys Pro Ala Asp Asn Leu Arg Ala Glu
        770                 775                 780
        Gly Leu Glu Cys Thr Lys Thr Cys Gln Asn Tyr Asp Leu Glu Cys Met
        785                 790                 795                 800
        Ser Met Gly Cys Val Ser Gly Cys Leu Cys Pro Pro Gly Met Val Arg
                        805                 810                 815
        His Glu Asn Arg Cys Val Ala Leu Glu Arg Cys Pro Cys Phe His Gln
                    820                 825                 830
        Gly Lys Glu Tyr Ala Pro Gly Glu Thr Val Lys Ile Gly Cys Asn Thr
                835                 840                 845
        Cys Val Cys Arg Asp Arg Lys Trp Asn Cys Thr Asp His Val Cys Asp
        850                 855                 860
        Ala Thr Cys Ser Thr Ile Gly Met Ala His Tyr Leu Thr Phe Asp Gly
        865                 870                 875                 880
        Leu Lys Tyr Leu Phe Pro Gly Glu Cys Gln Tyr Val Leu Val Gln Asp
                        885                 890                 895
```

```
Tyr Cys Gly Ser Asn Pro Gly Thr Phe Arg Ile Leu Val Gly Asn Lys
            900                 905                 910

Gly Cys Ser His Pro Ser Val Lys Cys Lys Arg Val Thr Ile Leu
            915                 920                 925

Val Glu Gly Gly Glu Ile Glu Leu Phe Asp Gly Glu Val Asn Val Lys
            930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp Gly Ile Gln Asn Asn Asp Leu Thr
            995                 1000                1005

Ser Ser Asn Leu Gln Val Glu Glu Asp Pro Val Asp Phe Gly Asn
       1010                 1015                1020

Ser Trp Lys Val Ser Ser Gln Cys Ala Asp Thr Arg Lys Val Pro
       1025                 1030                1035

Leu Asp Ser Ser Pro Ala Thr Cys His Asn Asn Ile Met Lys Gln
       1040                 1045                1050

Thr Met Val Asp Ser Ser Cys Arg Ile Leu Thr Ser Asp Val Phe
       1055                 1060                1065

Gln Asp Cys Asn Lys Leu Val Asp Pro Glu Pro Tyr Leu Asp Val
       1070                 1075                1080

Cys Ile Tyr Asp Thr Cys Ser Cys Glu Ser Ile Gly Asp Cys Ala
       1085                 1090                1095

Cys Phe Cys Asp Thr Ile Ala Ala Tyr Ala His Val Cys Ala Gln
       1100                 1105                1110

His Gly Lys Val Val Thr Trp Arg Thr Ala Thr Leu Cys Pro Gln
       1115                 1120                1125

Ser Cys Glu Glu Arg Asn Leu Arg Glu Asn Gly Tyr Glu Cys Glu
       1130                 1135                1140

Trp Arg Tyr Asn Ser Cys Ala Pro Ala Cys Gln Val Thr Cys Gln
       1145                 1150                1155

His Pro Glu Pro Leu Ala Cys Pro Val Gln Cys Val Glu Gly Cys
       1160                 1165                1170

His Ala His Cys Pro Pro Gly Lys Ile Leu Asp Glu Leu Leu Gln
       1175                 1180                1185

Thr Cys Val Asp Pro Glu Asp Cys Pro Val Cys Glu Val Ala Gly
       1190                 1195                1200

Arg Arg Phe Ala Ser Gly Lys Lys Val Thr Leu Asn Pro Ser Asp
       1205                 1210                1215

Pro Glu His Cys Gln Ile Cys His Cys Asp Val Val Asn Leu Thr
       1220                 1225                1230

Cys Glu Ala Cys Gln Glu Pro Gly Gly Leu Val Val Pro Pro Thr
       1235                 1240                1245

Asp Ala Pro Val Ser Pro Thr Thr Leu Tyr Val Glu Asp Ile Ser
       1250                 1255                1260

Glu Pro Pro Leu His Asp Phe Tyr Cys Ser Arg Leu Leu Asp Leu
       1265                 1270                1275

Val Phe Leu Leu Asp Gly Ser Ser Arg Leu Ser Glu Ala Glu Phe
       1280                 1285                1290
```

```
Glu Val Leu Lys Ala Phe Val Val Asp Met Met Glu Arg Leu Arg
    1295                1300                1305

Ile Ser Gln Lys Trp Val Arg Val Ala Val Val Glu Tyr His Asp
    1310                1315                1320

Gly Ser His Ala Tyr Ile Gly Leu Lys Asp Arg Lys Arg Pro Ser
    1325                1330                1335

Glu Leu Arg Arg Ile Ala Ser Gln Val Lys Tyr Ala Gly Ser Gln
    1340                1345                1350

Val Ala Ser Thr Ser Glu Val Leu Lys Tyr Thr Leu Phe Gln Ile
    1355                1360                1365

Phe Ser Lys Ile Asp Arg Pro Glu Ala Ser Arg Ile Thr Leu Leu
    1370                1375                1380

Leu Met Ala Ser Gln Glu Pro Gln Arg Met Ser Arg Asn Phe Val
    1385                1390                1395

Arg Tyr Val Gln Gly Leu Lys Lys Lys Val Ile Val Ile Pro
    1400                1405                1410

Val Gly Ile Gly Pro His Ala Asn Leu Lys Gln Ile Arg Leu Ile
    1415                1420                1425

Glu Lys Gln Ala Pro Glu Asn Lys Ala Phe Val Leu Ser Ser Val
    1430                1435                1440

Asp Glu Leu Glu Gln Gln Arg Asp Glu Ile Val Ser Tyr Leu Cys
    1445                1450                1455

Asp Leu Ala Pro Glu Ala Pro Pro Pro Thr Leu Pro Pro Asp Met
    1460                1465                1470

Ala Gln Val Thr Val Gly Pro Gly Leu Leu Gly Val Ser Thr Leu
    1475                1480                1485

Gly Pro Lys Arg Asn Ser Met Val Leu Asp Val Ala Phe Val Leu
    1490                1495                1500

Glu Gly Ser Asp Lys Ile Gly Glu Ala Asp Phe Asn Arg Ser Lys
    1505                1510                1515

Glu Phe Met Glu Glu Val Ile Gln Arg Met Asp Val Gly Gln Asp
    1520                1525                1530

Ser Ile His Val Thr Val Leu Gln Tyr Ser Tyr Met Val Thr Val
    1535                1540                1545

Glu Tyr Pro Phe Ser Glu Ala Gln Ser Lys Gly Asp Ile Leu Gln
    1550                1555                1560

Arg Val Arg Glu Ile Arg Tyr Gln Gly Gly Asn Arg Thr Asn Thr
    1565                1570                1575

Gly Leu Ala Leu Arg Tyr Leu Ser Asp His Ser Phe Leu Val Ser
    1580                1585                1590

Gln Gly Asp Arg Glu Gln Ala Pro Asn Leu Val Tyr Met Val Thr
    1595                1600                1605

Gly Asn Pro Ala Ser Asp Glu Ile Lys Arg Leu Pro Gly Asp Ile
    1610                1615                1620

Gln Val Val Pro Ile Gly Val Gly Pro Asn Ala Asn Val Gln Glu
    1625                1630                1635

Leu Glu Arg Ile Gly Trp Pro Asn Ala Pro Ile Leu Ile Gln Asp
    1640                1645                1650

Phe Glu Thr Leu Pro Arg Glu Ala Pro Asp Leu Val Leu Gln Arg
    1655                1660                1665

Cys Cys Ser Gly Glu Gly Leu Gln Ile Pro Thr Leu Ser Pro Ala
    1670                1675                1680

Pro Asp Cys Ser Gln Pro Leu Asp Val Ile Leu Leu Leu Asp Gly
```

```
            1685                1690                1695

Ser  Ser  Ser  Phe  Pro  Ala  Ser  Tyr  Phe  Asp  Glu  Met  Lys  Ser  Phe
     1700                1705                1710

Ala  Lys  Ala  Phe  Ile  Ser  Lys  Ala  Asn  Ile  Gly  Pro  Arg  Leu  Thr
     1715                1720                1725

Gln  Val  Ser  Val  Leu  Gln  Tyr  Gly  Ser  Ile  Thr  Thr  Ile  Asp  Val
     1730                1735                1740

Pro  Trp  Asn  Val  Val  Pro  Glu  Lys  Ala  His  Leu  Leu  Ser  Leu  Val
     1745                1750                1755

Asp  Val  Met  Gln  Arg  Glu  Gly  Gly  Pro  Ser  Gln  Ile  Gly  Asp  Ala
     1760                1765                1770

Leu  Gly  Phe  Ala  Val  Arg  Tyr  Leu  Thr  Ser  Glu  Met  His  Gly  Ala
     1775                1780                1785

Arg  Pro  Gly  Ala  Ser  Lys  Ala  Val  Val  Ile  Leu  Val  Thr  Asp  Val
     1790                1795                1800

Ser  Val  Asp  Ser  Val  Asp  Ala  Ala  Ala  Asp  Ala  Ala  Arg  Ser  Asn
     1805                1810                1815

Arg  Val  Thr  Val  Phe  Pro  Ile  Gly  Ile  Gly  Asp  Arg  Tyr  Asp  Ala
     1820                1825                1830

Ala  Gln  Leu  Arg  Ile  Leu  Ala  Gly  Pro  Ala  Gly  Asp  Ser  Asn  Val
     1835                1840                1845

Val  Lys  Leu  Gln  Arg  Ile  Glu  Asp  Leu  Pro  Thr  Met  Val  Thr  Leu
     1850                1855                1860

Gly  Asn  Ser  Phe  Leu  His  Lys  Leu  Cys  Ser  Gly  Phe  Val  Arg  Ile
     1865                1870                1875

Cys  Met  Asp  Glu  Asp  Gly  Asn  Glu  Lys  Arg  Pro  Gly  Asp  Val  Trp
     1880                1885                1890

Thr  Leu  Pro  Asp  Gln  Cys  His  Thr  Val  Thr  Cys  Gln  Pro  Asp  Gly
     1895                1900                1905

Gln  Thr  Leu  Leu  Lys  Ser  His  Arg  Val  Asn  Cys  Asp  Arg  Gly  Leu
     1910                1915                1920

Arg  Pro  Ser  Cys  Pro  Asn  Ser  Gln  Ser  Pro  Val  Lys  Val  Glu  Glu
     1925                1930                1935

Thr  Cys  Gly  Cys  Arg  Trp  Thr  Cys  Pro  Cys  Val  Cys  Thr  Gly  Ser
     1940                1945                1950

Ser  Thr  Arg  His  Ile  Val  Thr  Phe  Asp  Gly  Gln  Asn  Phe  Lys  Leu
     1955                1960                1965

Thr  Gly  Ser  Cys  Ser  Tyr  Val  Leu  Phe  Gln  Asn  Lys  Glu  Gln  Asp
     1970                1975                1980

Leu  Glu  Val  Ile  Leu  His  Asn  Gly  Ala  Cys  Ser  Pro  Gly  Ala  Arg
     1985                1990                1995

Gln  Gly  Cys  Met  Lys  Ser  Ile  Glu  Val  Lys  His  Ser  Ala  Leu  Ser
     2000                2005                2010

Val  Glu  Leu  His  Ser  Asp  Met  Glu  Val  Thr  Val  Asn  Gly  Arg  Leu
     2015                2020                2025

Val  Ser  Val  Pro  Tyr  Val  Gly  Gly  Asn  Met  Glu  Val  Asn  Val  Tyr
     2030                2035                2040

Gly  Ala  Ile  Met  His  Glu  Val  Arg  Phe  Asn  His  Leu  Gly  His  Ile
     2045                2050                2055

Phe  Thr  Phe  Thr  Pro  Gln  Asn  Asn  Glu  Phe  Gln  Leu  Gln  Leu  Ser
     2060                2065                2070

Pro  Lys  Thr  Phe  Ala  Ser  Lys  Thr  Tyr  Gly  Leu  Cys  Gly  Ile  Cys
     2075                2080                2085
```

-continued

| | | | | | | | | | |
|---|---|---|---|---|---|---|---|---|---|
|Asp|Glu 2090|Asn|Gly|Ala|Asn 2095|Asp|Phe|Met|Leu|Arg 2100|Asp|Gly|Thr|Val|
|Thr|Thr 2105|Asp|Trp|Lys|Thr 2110|Leu|Val|Gln|Glu|Trp 2115|Thr|Val|Gln|Arg|
|Pro|Gly 2120|Gln|Thr|Cys|Gln 2125|Pro|Ile|Leu|Glu|Glu 2130|Gln|Cys|Leu|Val|
|Pro|Asp 2135|Ser|Ser|His|Cys 2140|Gln|Val|Leu|Leu|Pro 2145|Leu|Phe|Ala|
|Glu|Cys 2150|His|Lys|Val|Leu 2155|Ala|Pro|Ala|Thr|Phe 2160|Tyr|Ala|Ile|Cys|
|Gln|Gln 2165|Asp|Ser|Cys|His 2170|Gln|Glu|Gln|Val|Cys 2175|Glu|Val|Ile|Ala|
|Ser|Tyr 2180|Ala|His|Leu|Cys 2185|Arg|Thr|Asn|Gly|Val 2190|Cys|Val|Asp|Trp|
|Arg|Thr 2195|Pro|Asp|Phe|Cys 2200|Ala|Met|Ser|Cys|Pro 2205|Pro|Ser|Leu|Val|
|Tyr|Asn 2210|His|Cys|Glu|His 2215|Gly|Cys|Pro|Arg|His 2220|Cys|Asp|Gly|Asn|
|Val|Ser 2225|Ser|Cys|Gly|Asp 2230|His|Pro|Ser|Glu|Gly 2235|Cys|Phe|Cys|Pro|
|Pro|Asp 2240|Lys|Val|Met|Leu 2245|Glu|Gly|Ser|Cys|Val 2250|Pro|Glu|Glu|Ala|
|Cys|Thr 2255|Gln|Cys|Ile|Gly 2260|Glu|Asp|Gly|Val|Gln 2265|His|Gln|Phe|Leu|
|Glu|Ala 2270|Trp|Val|Pro|Asp 2275|His|Gln|Pro|Cys|Gln 2280|Ile|Cys|Thr|Cys|
|Leu|Ser 2285|Gly|Arg|Lys|Val 2290|Asn|Cys|Thr|Thr|Gln 2295|Pro|Cys|Pro|Thr|
|Ala|Lys 2300|Ala|Pro|Thr|Cys 2305|Gly|Leu|Cys|Glu|Val 2310|Ala|Arg|Leu|Arg|
|Gln|Asn 2315|Ala|Asp|Gln|Cys 2320|Cys|Pro|Glu|Tyr|Glu 2325|Cys|Val|Cys|Asp|
|Pro|Val 2330|Ser|Cys|Asp|Leu 2335|Pro|Pro|Val|Pro|His 2340|Cys|Glu|Arg|Gly|
|Leu|Gln 2345|Pro|Thr|Leu|Thr 2350|Asn|Pro|Gly|Glu|Cys 2355|Arg|Pro|Asn|Phe|
|Thr|Cys 2360|Ala|Cys|Arg|Lys 2365|Glu|Glu|Cys|Lys|Arg 2370|Val|Ser|Pro|Pro|
|Ser|Cys 2375|Pro|Pro|His|Arg 2380|Leu|Pro|Thr|Leu|Arg 2385|Lys|Thr|Gln|Cys|
|Cys|Asp 2390|Glu|Tyr|Glu|Cys 2395|Ala|Cys|Asn|Cys|Val 2400|Asn|Ser|Thr|Val|
|Ser|Cys 2405|Pro|Leu|Gly|Tyr 2410|Leu|Ala|Ser|Thr|Ala 2415|Thr|Asn|Asp|Cys|
|Gly|Cys 2420|Thr|Thr|Thr|Thr 2425|Cys|Leu|Pro|Asp|Lys 2430|Val|Cys|Val|His|
|Arg|Ser 2435|Thr|Ile|Tyr|Pro 2440|Val|Gly|Gln|Phe|Trp 2445|Glu|Glu|Gly|Cys|
|Asp|Val 2450|Cys|Thr|Cys|Thr 2455|Asp|Met|Glu|Asp|Ala 2460|Val|Met|Gly|Leu|
|Arg|Val 2465|Ala|Gln|Cys|Ser 2470|Gln|Lys|Pro|Cys|Glu 2475|Asp|Ser|Cys|Arg|

```
Ser Gly Phe Thr Tyr Val Leu His Glu Gly Glu Cys Cys Gly Arg
2480                2485                2490

Cys Leu Pro Ser Ala Cys Glu Val Val Thr Gly Ser Pro Arg Gly
    2495                2500                2505

Asp Ser Gln Ser Ser Trp Lys Ser Val Gly Ser Gln Trp Ala Ser
    2510                2515                2520

Pro Glu Asn Pro Cys Leu Ile Asn Glu Cys Val Arg Val Lys Glu
    2525                2530                2535

Glu Val Phe Ile Gln Gln Arg Asn Val Ser Cys Pro Gln Leu Glu
    2540                2545                2550

Val Pro Val Cys Pro Ser Gly Phe Gln Leu Ser Cys Lys Thr Ser
    2555                2560                2565

Ala Cys Cys Pro Ser Cys Arg Cys Glu Arg Met Glu Ala Cys Met
    2570                2575                2580

Leu Asn Gly Thr Val Ile Gly Pro Gly Lys Thr Val Met Ile Asp
    2585                2590                2595

Val Cys Thr Thr Cys Arg Cys Met Val Gln Val Gly Val Ile Ser
    2600                2605                2610

Gly Phe Lys Leu Glu Cys Arg Lys Thr Thr Cys Asn Pro Cys Pro
    2615                2620                2625

Leu Gly Tyr Lys Glu Glu Asn Asn Thr Gly Glu Cys Cys Gly Arg
    2630                2635                2640

Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810
```

<210> SEQ ID NO 25
<211> LENGTH: 3429
<212> TYPE: PRT
<213> ORGANISM: Artificial
<220> FEATURE:
<223> OTHER INFORMATION: Amino acid sequence of human VWF albumin fusion preproprotein

<400> SEQUENCE: 25

```
Met Ile Pro Ala Arg Phe Ala Gly Val Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65              70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
            115                 120                 125

Leu Ser Gly Glu Ala Tyr Gly Phe Val Ala Arg Ile Asp Gly Ser Gly
130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
                180                 185                 190

Leu Ser Ser Gly Glu Gln Trp Cys Glu Arg Ala Ser Pro Pro Ser Ser
                195                 200                 205

Ser Cys Asn Ile Ser Ser Gly Glu Met Gln Lys Gly Leu Trp Glu Gln
210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
                260                 265                 270

Arg Thr Cys Ala Gln Glu Gly Met Val Leu Tyr Gly Trp Thr Asp His
            275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
                340                 345                 350

Ser Gly Lys Arg Tyr Pro Pro Gly Thr Ser Leu Ser Arg Asp Cys Asn
            355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415
```

-continued

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
    515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr

-continued

```
            835                 840                 845
Cys Val Cys Arg Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                    885                 890                 895

Tyr Cys Gly Ser Asn Pro Gly Thr Phe Arg Ile Leu Val Gly Asn Lys
                900                 905                 910

Gly Cys Ser His Pro Ser Val Lys Cys Lys Arg Val Thr Ile Leu
                915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
                980                 985                 990

Cys Gly Leu Cys Gly Asn Phe Asp  Gly Ile Gln Asn Asn  Asp Leu Thr
                995                 1000                1005

Ser Ser Asn Leu Gln Val Glu  Glu Asp Pro Val Asp  Phe Gly Asn
1010                1015                1020

Ser Trp Lys Val Ser Ser Gln  Cys Ala Asp Thr Arg  Lys Val Pro
1025                1030                1035

Leu Asp Ser Ser Pro Ala Thr  Cys His Asn Asn Ile  Met Lys Gln
1040                1045                1050

Thr Met Val Asp Ser Ser Cys  Arg Ile Leu Thr Ser  Asp Val Phe
1055                1060                1065

Gln Asp Cys Asn Lys Leu Val  Asp Pro Glu Pro Tyr  Leu Asp Val
1070                1075                1080

Cys Ile Tyr Asp Thr Cys Ser  Cys Glu Ser Ile Gly  Asp Cys Ala
1085                1090                1095

Cys Phe Cys Asp Thr Ile Ala  Ala Tyr Ala His Val  Cys Ala Gln
1100                1105                1110

His Gly Lys Val Val Thr Trp  Arg Thr Ala Thr Leu  Cys Pro Gln
1115                1120                1125

Ser Cys Glu Glu Arg Asn Leu  Arg Glu Asn Gly Tyr  Glu Cys Glu
1130                1135                1140

Trp Arg Tyr Asn Ser Cys Ala  Pro Ala Cys Gln Val  Thr Cys Gln
1145                1150                1155

His Pro Glu Pro Leu Ala Cys  Pro Val Gln Cys Val  Glu Gly Cys
1160                1165                1170

His Ala His Cys Pro Pro Gly  Lys Ile Leu Asp Glu  Leu Leu Gln
1175                1180                1185

Thr Cys Val Asp Pro Glu Asp  Cys Pro Val Cys Glu  Val Ala Gly
1190                1195                1200

Arg Arg Phe Ala Ser Gly Lys  Lys Val Thr Leu Asn  Pro Ser Asp
1205                1210                1215

Pro Glu His Cys Gln Ile Cys  His Cys Asp Val Val  Asn Leu Thr
1220                1225                1230

Cys Glu Ala Cys Gln Glu Pro  Gly Gly Leu Val Val  Pro Pro Thr
1235                1240                1245
```

```
Asp Ala Pro Val Ser Pro Thr Thr Leu Tyr Val Glu Asp Ile Ser
    1250                1255                1260

Glu Pro Pro Leu His Asp Phe Tyr Cys Ser Arg Leu Leu Asp Leu
    1265                1270                1275

Val Phe Leu Leu Asp Gly Ser Ser Arg Leu Ser Glu Ala Glu Phe
    1280                1285                1290

Glu Val Leu Lys Ala Phe Val Val Asp Met Met Glu Arg Leu Arg
    1295                1300                1305

Ile Ser Gln Lys Trp Val Arg Val Ala Val Val Glu Tyr His Asp
    1310                1315                1320

Gly Ser His Ala Tyr Ile Gly Leu Lys Asp Arg Lys Arg Pro Ser
    1325                1330                1335

Glu Leu Arg Arg Ile Ala Ser Gln Val Lys Tyr Ala Gly Ser Gln
    1340                1345                1350

Val Ala Ser Thr Ser Glu Val Leu Lys Tyr Thr Leu Phe Gln Ile
    1355                1360                1365

Phe Ser Lys Ile Asp Arg Pro Glu Ala Ser Arg Ile Thr Leu Leu
    1370                1375                1380

Leu Met Ala Ser Gln Glu Pro Gln Arg Met Ser Arg Asn Phe Val
    1385                1390                1395

Arg Tyr Val Gln Gly Leu Lys Lys Lys Lys Val Ile Val Ile Pro
    1400                1405                1410

Val Gly Ile Gly Pro His Ala Asn Leu Lys Gln Ile Arg Leu Ile
    1415                1420                1425

Glu Lys Gln Ala Pro Glu Asn Lys Ala Phe Val Leu Ser Ser Val
    1430                1435                1440

Asp Glu Leu Glu Gln Gln Arg Asp Glu Ile Val Ser Tyr Leu Cys
    1445                1450                1455

Asp Leu Ala Pro Glu Ala Pro Pro Pro Thr Leu Pro Pro Asp Met
    1460                1465                1470

Ala Gln Val Thr Val Gly Pro Gly Leu Leu Gly Val Ser Thr Leu
    1475                1480                1485

Gly Pro Lys Arg Asn Ser Met Val Leu Asp Val Ala Phe Val Leu
    1490                1495                1500

Glu Gly Ser Asp Lys Ile Gly Glu Ala Asp Phe Asn Arg Ser Lys
    1505                1510                1515

Glu Phe Met Glu Glu Val Ile Gln Arg Met Asp Val Gly Gln Asp
    1520                1525                1530

Ser Ile His Val Thr Val Leu Gln Tyr Ser Tyr Met Val Thr Val
    1535                1540                1545

Glu Tyr Pro Phe Ser Glu Ala Gln Ser Lys Gly Asp Ile Leu Gln
    1550                1555                1560

Arg Val Arg Glu Ile Arg Tyr Gln Gly Gly Asn Arg Thr Asn Thr
    1565                1570                1575

Gly Leu Ala Leu Arg Tyr Leu Ser Asp His Ser Phe Leu Val Ser
    1580                1585                1590

Gln Gly Asp Arg Glu Gln Ala Pro Asn Leu Val Tyr Met Val Thr
    1595                1600                1605

Gly Asn Pro Ala Ser Asp Glu Ile Lys Arg Leu Pro Gly Asp Ile
    1610                1615                1620

Gln Val Val Pro Ile Gly Val Gly Pro Asn Ala Asn Val Gln Glu
    1625                1630                1635
```

```
Leu Glu Arg Ile Gly Trp Pro Asn Ala Pro Ile Leu Ile Gln Asp
    1640                1645                1650

Phe Glu Thr Leu Pro Arg Glu Ala Pro Asp Leu Val Leu Gln Arg
    1655                1660                1665

Cys Cys Ser Gly Glu Gly Leu Gln Ile Pro Thr Leu Ser Pro Ala
    1670                1675                1680

Pro Asp Cys Ser Gln Pro Leu Asp Val Ile Leu Leu Leu Asp Gly
    1685                1690                1695

Ser Ser Ser Phe Pro Ala Ser Tyr Phe Asp Glu Met Lys Ser Phe
    1700                1705                1710

Ala Lys Ala Phe Ile Ser Lys Ala Asn Ile Gly Pro Arg Leu Thr
    1715                1720                1725

Gln Val Ser Val Leu Gln Tyr Gly Ser Ile Thr Thr Ile Asp Val
    1730                1735                1740

Pro Trp Asn Val Val Pro Glu Lys Ala His Leu Leu Ser Leu Val
    1745                1750                1755

Asp Val Met Gln Arg Glu Gly Gly Pro Ser Gln Ile Gly Asp Ala
    1760                1765                1770

Leu Gly Phe Ala Val Arg Tyr Leu Thr Ser Glu Met His Gly Ala
    1775                1780                1785

Arg Pro Gly Ala Ser Lys Ala Val Val Ile Leu Val Thr Asp Val
    1790                1795                1800

Ser Val Asp Ser Val Asp Ala Ala Ala Asp Ala Ala Arg Ser Asn
    1805                1810                1815

Arg Val Thr Val Phe Pro Ile Gly Ile Gly Asp Arg Tyr Asp Ala
    1820                1825                1830

Ala Gln Leu Arg Ile Leu Ala Gly Pro Ala Gly Asp Ser Asn Val
    1835                1840                1845

Val Lys Leu Gln Arg Ile Glu Asp Leu Pro Thr Met Val Thr Leu
    1850                1855                1860

Gly Asn Ser Phe Leu His Lys Leu Cys Ser Gly Phe Val Arg Ile
    1865                1870                1875

Cys Met Asp Glu Asp Gly Asn Glu Lys Arg Pro Gly Asp Val Trp
    1880                1885                1890

Thr Leu Pro Asp Gln Cys His Thr Val Thr Cys Gln Pro Asp Gly
    1895                1900                1905

Gln Thr Leu Leu Lys Ser His Arg Val Asn Cys Asp Arg Gly Leu
    1910                1915                1920

Arg Pro Ser Cys Pro Asn Ser Gln Ser Pro Val Lys Val Glu Glu
    1925                1930                1935

Thr Cys Gly Cys Arg Trp Thr Cys Pro Cys Val Cys Thr Gly Ser
    1940                1945                1950

Ser Thr Arg His Ile Val Thr Phe Asp Gly Gln Asn Phe Lys Leu
    1955                1960                1965

Thr Gly Ser Cys Ser Tyr Val Leu Phe Gln Asn Lys Glu Gln Asp
    1970                1975                1980

Leu Glu Val Ile Leu His Asn Gly Ala Cys Ser Pro Gly Ala Arg
    1985                1990                1995

Gln Gly Cys Met Lys Ser Ile Glu Val Lys His Ser Ala Leu Ser
    2000                2005                2010

Val Glu Leu His Ser Asp Met Glu Val Thr Val Asn Gly Arg Leu
    2015                2020                2025

Val Ser Val Pro Tyr Val Gly Gly Asn Met Glu Val Asn Val Tyr
```

```
                2030                2035                2040

Gly Ala Ile Met His Glu Val Arg Phe Asn His Leu Gly His Ile
    2045                2050                2055

Phe Thr Phe Thr Pro Gln Asn Asn Glu Phe Gln Leu Gln Leu Ser
    2060                2065                2070

Pro Lys Thr Phe Ala Ser Lys Thr Tyr Gly Leu Cys Gly Ile Cys
    2075                2080                2085

Asp Glu Asn Gly Ala Asn Asp Phe Met Leu Arg Asp Gly Thr Val
    2090                2095                2100

Thr Thr Asp Trp Lys Thr Leu Val Gln Glu Trp Thr Val Gln Arg
    2105                2110                2115

Pro Gly Gln Thr Cys Gln Pro Ile Leu Glu Glu Gln Cys Leu Val
    2120                2125                2130

Pro Asp Ser Ser His Cys Gln Val Leu Leu Leu Pro Leu Phe Ala
    2135                2140                2145

Glu Cys His Lys Val Leu Ala Pro Ala Thr Phe Tyr Ala Ile Cys
    2150                2155                2160

Gln Gln Asp Ser Cys His Gln Glu Gln Val Cys Glu Val Ile Ala
    2165                2170                2175

Ser Tyr Ala His Leu Cys Arg Thr Asn Gly Val Cys Val Asp Trp
    2180                2185                2190

Arg Thr Pro Asp Phe Cys Ala Met Ser Cys Pro Pro Ser Leu Val
    2195                2200                2205

Tyr Asn His Cys Glu His Gly Cys Pro Arg His Cys Asp Gly Asn
    2210                2215                2220

Val Ser Ser Cys Gly Asp His Pro Ser Glu Gly Cys Phe Cys Pro
    2225                2230                2235

Pro Asp Lys Val Met Leu Glu Gly Ser Cys Val Pro Glu Glu Ala
    2240                2245                2250

Cys Thr Gln Cys Ile Gly Glu Asp Gly Val Gln His Gln Phe Leu
    2255                2260                2265

Glu Ala Trp Val Pro Asp His Gln Pro Cys Gln Ile Cys Thr Cys
    2270                2275                2280

Leu Ser Gly Arg Lys Val Asn Cys Thr Thr Gln Pro Cys Pro Thr
    2285                2290                2295

Ala Lys Ala Pro Thr Cys Gly Leu Cys Glu Val Ala Arg Leu Arg
    2300                2305                2310

Gln Asn Ala Asp Gln Cys Cys Pro Glu Tyr Glu Cys Val Cys Asp
    2315                2320                2325

Pro Val Ser Cys Asp Leu Pro Pro Val Pro His Cys Glu Arg Gly
    2330                2335                2340

Leu Gln Pro Thr Leu Thr Asn Pro Gly Glu Cys Arg Pro Asn Phe
    2345                2350                2355

Thr Cys Ala Cys Arg Lys Glu Glu Cys Lys Arg Val Ser Pro Pro
    2360                2365                2370

Ser Cys Pro Pro His Arg Leu Pro Thr Leu Arg Lys Thr Gln Cys
    2375                2380                2385

Cys Asp Glu Tyr Glu Cys Ala Cys Asn Cys Val Asn Ser Thr Val
    2390                2395                2400

Ser Cys Pro Leu Gly Tyr Leu Ala Ser Thr Ala Thr Asn Asp Cys
    2405                2410                2415

Gly Cys Thr Thr Thr Thr Cys Leu Pro Asp Lys Val Cys Val His
    2420                2425                2430
```

```
Arg Ser Thr Ile Tyr Pro Val Gly Gln Phe Trp Glu Glu Gly Cys
2435                2440                2445

Asp Val Cys Thr Cys Thr Asp Met Glu Asp Ala Val Met Gly Leu
2450                2455                2460

Arg Val Ala Gln Cys Ser Gln Lys Pro Cys Glu Asp Ser Cys Arg
2465                2470                2475

Ser Gly Phe Thr Tyr Val Leu His Glu Gly Cys Cys Gly Arg
2480                2485                2490

Cys Leu Pro Ser Ala Cys Glu Val Val Thr Gly Ser Pro Arg Gly
2495                2500                2505

Asp Ser Gln Ser Ser Trp Lys Ser Val Gly Ser Gln Trp Ala Ser
2510                2515                2520

Pro Glu Asn Pro Cys Leu Ile Asn Glu Cys Val Arg Val Lys Glu
2525                2530                2535

Glu Val Phe Ile Gln Gln Arg Asn Val Ser Cys Pro Gln Leu Glu
2540                2545                2550

Val Pro Val Cys Pro Ser Gly Phe Gln Leu Ser Cys Lys Thr Ser
2555                2560                2565

Ala Cys Cys Pro Ser Cys Arg Cys Glu Arg Met Glu Ala Cys Met
2570                2575                2580

Leu Asn Gly Thr Val Ile Gly Pro Gly Lys Thr Val Met Ile Asp
2585                2590                2595

Val Cys Thr Thr Cys Arg Cys Met Val Gln Val Gly Val Ile Ser
2600                2605                2610

Gly Phe Lys Leu Glu Cys Arg Lys Thr Thr Cys Asn Pro Cys Pro
2615                2620                2625

Leu Gly Tyr Lys Glu Glu Asn Asn Thr Gly Glu Cys Cys Gly Arg
2630                2635                2640

Cys Leu Pro Thr Ala Cys Thr Ile Gln Leu Arg Gly Gly Gln Ile
2645                2650                2655

Met Thr Leu Lys Arg Asp Glu Thr Leu Gln Asp Gly Cys Asp Thr
2660                2665                2670

His Phe Cys Lys Val Asn Glu Arg Gly Glu Tyr Phe Trp Glu Lys
2675                2680                2685

Arg Val Thr Gly Cys Pro Pro Phe Asp Glu His Lys Cys Leu Ala
2690                2695                2700

Glu Gly Gly Lys Ile Met Lys Ile Pro Gly Thr Cys Cys Asp Thr
2705                2710                2715

Cys Glu Glu Pro Glu Cys Asn Asp Ile Thr Ala Arg Leu Gln Tyr
2720                2725                2730

Val Lys Val Gly Ser Cys Lys Ser Glu Val Glu Val Asp Ile His
2735                2740                2745

Tyr Cys Gln Gly Lys Cys Ala Ser Lys Ala Met Tyr Ser Ile Asp
2750                2755                2760

Ile Asn Asp Val Gln Asp Gln Cys Ser Cys Cys Ser Pro Thr Arg
2765                2770                2775

Thr Glu Pro Met Gln Val Ala Leu His Cys Thr Asn Gly Ser Val
2780                2785                2790

Val Tyr His Glu Val Leu Asn Ala Met Glu Cys Lys Cys Ser Pro
2795                2800                2805

Arg Lys Cys Ser Lys Ser Ser Gly Gly Ser Gly Gly Ser Gly Gly
2810                2815                2820
```

```
Ser Gly Gly Ser Gly Gly Ser Gly Gly Ser Gly Gly
    2825                2830            2835

Ser Gly Gly Ser Gly Ser Asp Ala His Lys Ser Glu Val Ala His
    2840                2845            2850

Arg Phe Lys Asp Leu Gly Glu Glu Asn Phe Lys Ala Leu Val Leu
    2855                2860            2865

Ile Ala Phe Ala Gln Tyr Leu Gln Gln Cys Pro Phe Glu Asp His
    2870                2875            2880

Val Lys Leu Val Asn Glu Val Thr Glu Phe Ala Lys Thr Cys Val
    2885                2890            2895

Ala Asp Glu Ser Ala Glu Asn Cys Asp Lys Ser Leu His Thr Leu
    2900                2905            2910

Phe Gly Asp Lys Leu Cys Thr Val Ala Thr Leu Arg Glu Thr Tyr
    2915                2920            2925

Gly Glu Met Ala Asp Cys Cys Ala Lys Gln Glu Pro Glu Arg Asn
    2930                2935            2940

Glu Cys Phe Leu Gln His Lys Asp Asp Asn Pro Asn Leu Pro Arg
    2945                2950            2955

Leu Val Arg Pro Glu Val Asp Val Met Cys Thr Ala Phe His Asp
    2960                2965            2970

Asn Glu Glu Thr Phe Leu Lys Lys Tyr Leu Tyr Glu Ile Ala Arg
    2975                2980            2985

Arg His Pro Tyr Phe Tyr Ala Pro Glu Leu Leu Phe Phe Ala Lys
    2990                2995            3000

Arg Tyr Lys Ala Ala Phe Thr Glu Cys Cys Gln Ala Ala Asp Lys
    3005                3010            3015

Ala Ala Cys Leu Leu Pro Lys Leu Asp Glu Leu Arg Asp Glu Gly
    3020                3025            3030

Lys Ala Ser Ser Ala Lys Gln Arg Leu Lys Cys Ala Ser Leu Gln
    3035                3040            3045

Lys Phe Gly Glu Arg Ala Phe Lys Ala Trp Ala Val Ala Arg Leu
    3050                3055            3060

Ser Gln Arg Phe Pro Lys Ala Glu Phe Ala Glu Val Ser Lys Leu
    3065                3070            3075

Val Thr Asp Leu Thr Lys Val His Thr Glu Cys Cys His Gly Asp
    3080                3085            3090

Leu Leu Glu Cys Ala Asp Asp Arg Ala Asp Leu Ala Lys Tyr Ile
    3095                3100            3105

Cys Glu Asn Gln Asp Ser Ile Ser Ser Lys Leu Lys Glu Cys Cys
    3110                3115            3120

Glu Lys Pro Leu Leu Glu Lys Ser His Cys Ile Ala Glu Val Glu
    3125                3130            3135

Asn Asp Glu Met Pro Ala Asp Leu Pro Ser Leu Ala Ala Asp Phe
    3140                3145            3150

Val Glu Ser Lys Asp Val Cys Lys Asn Tyr Ala Glu Ala Lys Asp
    3155                3160            3165

Val Phe Leu Gly Met Phe Leu Tyr Glu Tyr Ala Arg Arg His Pro
    3170                3175            3180

Asp Tyr Ser Val Val Leu Leu Leu Arg Leu Ala Lys Thr Tyr Glu
    3185                3190            3195

Thr Thr Leu Glu Lys Cys Cys Ala Ala Ala Asp Pro His Glu Cys
    3200                3205            3210

Tyr Ala Lys Val Phe Asp Glu Phe Lys Pro Leu Val Glu Glu Pro
```

-continued

| | | | | | | | | | | |
|---|---|---|---|---|---|---|---|---|---|---|
| | | | 3215 | | | 3220 | | | 3225 | |
| Gln | Asn | Leu | Ile | Lys | Gln | Asn | Cys | Glu | Leu | Phe | Glu | Gln | Leu | Gly |
| | 3230 | | | | 3235 | | | | 3240 | |
| Glu | Tyr | Lys | Phe | Gln | Asn | Ala | Leu | Leu | Val | Arg | Tyr | Thr | Lys | Lys |
| | 3245 | | | | 3250 | | | | 3255 | |
| Val | Pro | Gln | Val | Ser | Thr | Pro | Thr | Leu | Val | Glu | Val | Ser | Arg | Asn |
| | 3260 | | | | 3265 | | | | 3270 | |
| Leu | Gly | Lys | Val | Gly | Ser | Lys | Cys | Cys | Lys | His | Pro | Glu | Ala | Lys |
| | 3275 | | | | 3280 | | | | 3285 | |
| Arg | Met | Pro | Cys | Ala | Glu | Asp | Tyr | Leu | Ser | Val | Leu | Asn | Gln |
| | 3290 | | | | 3295 | | | | 3300 | |
| Leu | Cys | Val | Leu | His | Glu | Lys | Thr | Pro | Val | Ser | Asp | Arg | Val | Thr |
| | 3305 | | | | 3310 | | | | 3315 | |
| Lys | Cys | Cys | Thr | Glu | Ser | Leu | Val | Asn | Arg | Arg | Pro | Cys | Phe | Ser |
| | 3320 | | | | 3325 | | | | 3330 | |
| Ala | Leu | Glu | Val | Asp | Glu | Thr | Tyr | Val | Pro | Lys | Glu | Phe | Asn | Ala |
| | 3335 | | | | 3340 | | | | 3345 | |
| Glu | Thr | Phe | Thr | Phe | His | Ala | Asp | Ile | Cys | Thr | Leu | Ser | Glu | Lys |
| | 3350 | | | | 3355 | | | | 3360 | |
| Glu | Arg | Gln | Ile | Lys | Lys | Gln | Thr | Ala | Leu | Val | Glu | Leu | Val | Lys |
| | 3365 | | | | 3370 | | | | 3375 | |
| His | Lys | Pro | Lys | Ala | Thr | Lys | Glu | Gln | Leu | Lys | Ala | Val | Met | Asp |
| | 3380 | | | | 3385 | | | | 3390 | |
| Asp | Phe | Ala | Ala | Phe | Val | Glu | Lys | Cys | Cys | Lys | Ala | Asp | Asp | Lys |
| | 3395 | | | | 3400 | | | | 3405 | |
| Glu | Thr | Cys | Phe | Ala | Glu | Glu | Gly | Lys | Lys | Leu | Val | Ala | Ala | Ser |
| | 3410 | | | | 3415 | | | | 3420 | |
| Gln | Ala | Ala | Leu | Gly | Leu |
| | 3425 | |